United States Patent
Sierks et al.

(10) Patent No.: US 10,191,068 B2
(45) Date of Patent: Jan. 29, 2019

(54) ANTIBODY BASED REAGENTS THAT SPECIFICALLY RECOGNIZE NEURODEGENERATIVE DISEASE RELATED FORMS OF THE PROTEIN TDP-43

(71) Applicant: ARIZONA BOARD OF REGENTS ON BEHALF OF ARIZONA STATE UNIVERSITY, Scottsdale, AZ (US)

(72) Inventors: Michael Sierks, Ft. McDowell, AZ (US); Stephanie Williams, Phoenix, AZ (US); Lalitha Venkataraman, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/114,356

(22) PCT Filed: Feb. 2, 2015

(86) PCT No.: PCT/US2015/014121
§ 371 (c)(1),
(2) Date: Jul. 26, 2016

(87) PCT Pub. No.: WO2015/117088
PCT Pub. Date: Aug. 6, 2015

(65) Prior Publication Data
US 2017/0010284 A1    Jan. 12, 2017

Related U.S. Application Data

(60) Provisional application No. 61/934,443, filed on Jan. 31, 2014.

(51) Int. Cl.
*C07K 16/18*      (2006.01)
*G01N 33/68*      (2006.01)

(52) U.S. Cl.
CPC ......... *G01N 33/6896* (2013.01); *C07K 16/18* (2013.01); *C07K 2317/622* (2013.01); *G01N 2800/285* (2013.01); *G01N 2800/2814* (2013.01)

(58) Field of Classification Search
None
See application file for complete search history.

(56) References Cited

U.S. PATENT DOCUMENTS

| 8,617,549 | B2 | 12/2013 | Sierks | |
| 2008/0131423 | A1* | 6/2008 | Mori | C07K 16/2803 424/130.1 |
| 2010/0136573 | A1 | 6/2010 | Petrucelli et al. | |
| 2014/0011691 | A1 | 1/2014 | Sierks et al. | |

OTHER PUBLICATIONS

Amador-Ortiz, et al., "TDP-43 immunoreactivity in hippocampal sclerosis and Alzheimer's disease", Annals of Neurology, 2007, 61(5):435-45.
Barkhordarian, et al., "Isolating recombinant antibodies against specific protein morphologies using atomic force microscopy and phage display technologies", Protein Eng Des Sel 19 (11), 497-502 (2006).
Buratti, et al., "Multiple roles of TDP-43 in gene expression, splicing regulation, and human disease", Frontiers in Bioscience, 2008, 13(3):867-78.
Buratti, et al., "Nuclear factor TDP-43 binds to the polymorphic TG repeats in CFTR intron 8 and causes skipping of exon 9: a functional link with disease penetrance", American Journal of Human Genetics, Jun. 2004, 74(6):1322-5.
Dickson, "TDP-43 Immunoreactivity in Neurodegenerative Disease: Disease versus Mechanism-Specificity", Acta Neuropathologica, 2008, 115(1):147-9.
El-Agnaf, et al., "Detection of oligomeric forms of alpha-synuclein protein in human plasma as a potential biomarker for Parkinson's disease", Faseb J 20, 419-25 (2006).
Emadi, et al., "Detecting morphologically distinct oligomeric forms of alpha-synuclein", J. Biol. Chem. 284 (17), 11048-11058 (2009).
Emadi, et al., "Inhibiting aggregation of alpha-synuclein with human single chain antibody fragments", Biochemistry, vol. 43 (10), 2871-2878 (2004).
Emadi, et al., "Isolation of a human single chain antibody fragment against oligomeric alpha-synuclein that inhibits aggregation and prevents alpha-synuclein-induced toxicity", J Mol Biol 368, 1132-44 (2007).
Farmer, et al., "Coexisting adult polyglucosan body disease with frontotemporal lobar degeneration with transactivation response DNA-binding protein-43 (TDP-43)—positive neuronal inclusions", Neurocase 19.1 (2013): 67-75.
Flood, et al., "Developing predictive CSF biomarkers—A challenge critical to success in Alzheimer's disease and neuropsychiatric translational medicine", Biochem Pharmacol. 81:p. 1422-34.
Georganopoulou, et al., "Nanoparticle-based detection in cerebral spinal fluid of a soluble pathogenic biomarker for Alzheimer's disease", PNAS USA, 2005, 102(7):2273-76.
Geser, et al., "On the development of markers for pathological TDP-43 in amyotrophic lateral sclerosis with and without dementia", Prog Neurobiol, Dec. 2011, vol. 95, No. 4, pp. 649-662.
Graber, et al., "Progressive changes in microglia and macrophages in spinal cord and peripheral nerve in the transgenic rat model of amyotrophic lateral sclerosis", J Neuroinflammation. 7: p. 8.

(Continued)

*Primary Examiner* — Gregory S Emch
*Assistant Examiner* — Aditi Dutt
(74) *Attorney, Agent, or Firm* — Viksnins Harris Padys Malen LLP

(57) ABSTRACT

The invention relates to antibodies, antibody fragments and binding agents that specifically recognize TDP-43 associated with frontotemporal dementia (FTD), but not TDP-43 associated with amyotrophic lateral sclerosis (ALS) or TDP-43 associated with healthy human brain tissue, and antibodies, antibody fragments and binding agents that specifically recognize TDP-43 associated with ALS, but not TDP-43 associated FTD or TDP-43 associated with healthy human brain tissue.

14 Claims, 19 Drawing Sheets
Specification includes a Sequence Listing.

(56) References Cited

OTHER PUBLICATIONS

Graber, et al., "Synthetic triterpenoid CDDO derivatives modulate cytoprotective or immunological properties in astrocytes, neurons, and microglia", J Neuroimmune Pharmacol. 6: p. 107-20 2011.
Herman, et al., "β-amyloid triggers ALS-associated TDP-43 pathology in AD models", Brain Research, 2011, 1386:191-9.
Hu, et al., "Biomarkers in frontotemporal lobar degenerations—progress and challenges", Progress in Neurobiology, 2011, 95(4):636-48.
Hu, et al., "Novel CSF biomarkers for frontotemporal lobar degenerations", Neurology 75.23 (2010): 2079-2086.
Johnson, et al., "TDP-43 is intrinsically aggregation-prone, and amyotrophic lateral sclerosis-linked mutations accelerate aggregation and increase toxicity", Journal of Biological Chemistry, Jul. 2009, 284(30):20329-39.
Kasturirangan, et al., "Isolation and Characterization of Antibody Fragments Selective for Specific Protein Morphologies from Nanogram Antigen Samples", Biotechnology Progress, 2013. 29(2): 463-71.
Kasturirangan, et al., "Nanobody specific for oligomeric β-amyloid stabilizes nontoxic form", Neurobiol Aging 33(7), 1320-1328 (2012).
Liu et al., "Proteolytic antibody light chains alter beta-amyloid aggregation and prevent cytotoxicity", Biochemistry, 2004. 43(31): p. 9999-10007.
Liu et al., "Residues 17-20 and 30-35 of beta-amyloid play critical roles in aggregation", J Neurosci Res, 2004. 75(2): p. 162-71.
Liu et al., "Single chain variable fragments against beta-amyloid (Abeta) can inhibit Abeta aggregation and prevent abeta-induced neurotoxicity", Biochemistry, 2004. 43(22): p. 6959-67.
MacKenzie, et al., "Nomenclature and nosology for neuropathologic subtypes of frontotemporal lobar degeneration: an update", Acta Neuropathol, 2010. 119(1): 1-4.
MacKenzie, "TDP-43 and FUS in amyotrophic lateral sclerosis and frontotemporal dementia", Lancet Neurol. 9(10): p. 995-1007 2010.
Marcus, et al., "Characterization of an antibody scFv that recognizes fibrillar insulin and beta-amyloid using Atomic Force Microscopy", Nanomedicine, Mar. 2008, 4(1):1-7.
Marcus, et al., "Isolation of an scFv targeting BRG 1 using phage display with characterization by AFM", Biochem Biophys Res Commun, 2006. 342(4): p. 1123-9.
Meraz-Rios, et al., "Tau oligomers and aggregation in Alzheimer's disease", J Neurochem, 2010. 112(6): p. 1353-67.
Noto, et al., "Elevated CSF TDP-43 levels in amyotrophic lateral sclerosis: specificity, sensitivity, and a possible prognostic value", Amyotrophic Lateral Sclerosis, 2011, 12(2):140-3.
Patent Cooperation Treaty, International Searching Authority, Search Report and Written Opinion for PCT/US15/14121, 13 pages, dated Aug. 4, 2015.
Shlyakhtenko, et al., "Single-molecule selection and recovery of structure-specific antibodies using atomic force microscopy", Nanomedicine, 2007. 3(3): p. 192-7.
Stommel, et al., "Tumor necrosis factor-alpha induces changes in mitochondrial cellular distribution in motor neurons", Neuroscience, 2007. 146(3): 1013-9.
Swarup, et al., "Pathological hallmarks of amyotrophic lateral sclerosis/frontotemporal lobar degeneration in transgenic mice produced with TDP-43 genomic fragments", Brain. 134: p. 2610-26, 2011.
Ullian, et al., "Schwann cells and astrocytes induce synapse formation by spinal motor neurons in culture", Mol Cell Neurosci, 2004.25: p. 241-51.
Uryu, et al., "Concomitant TAR-DNA-Binding Protein 43 Pathology Is Present in Alzheimer Disease and Corticobasal Degeneration but Not in Other Tauopathies", Journal of Neuropathology & Experimental Neurology, 2008, 67(6):555-64.
Walsh, et al., "A beta oligomers—a decade of discovery", J Neurochem, 2007. 101(5): p. 1172-84.
Walsh, et al., "Naturally secreted oligomers of amyloid beta protein potently inhibit hippocampal long-term potentiation in vivo", Nature, 2002. 416(6880): p. 535-9.
Wang, et al., "Characterizing Antibody Specificity to Different Protein Morphologies by AFM", Langmuir, 2008, 2009.
Wilson, et al., "TDP-43 in aging and Alzheimer's disease—a review", International Journal of Clinical & Experimental Pathology, Feb. 2011, 4(2):147-55.
Yuan, et al., "Intracellular targeting and clearance of oligomeric alpha-synuclein alleviates toxicity in mammalian cells", Neuroscience Letters, Jul. 2009, 459(1):16-8.
Zameer, et al., "Anti-oligomeric Abeta single-chain variable domain antibody blocks Abeta-induced toxicity against human neuroblastoma cells", J Mol Biol 384 (4), 917-928 (2008).
Zameer, et al., "Single chain Fv antibodies against the 25-35 Abeta fragment inhibit aggregation and toxicity of Abeta42", Biochemistry, 2006. 45(38): p. 11532-9.
Zhou, et al., "A human single-chain Fv intrabody blocks aberrant cellular effects of overexpressed alpha-synuclein", Mol Ther, 2004. 10(6): p. 1023-31.

* cited by examiner

BSA ROUND 1:

BINDING TO BSA (ROUND 1) AT 20μm

BINDING TO BSA (ROUND 1) AT 5μm

BSA ROUND 12:

BINDING TO BSA (ROUND 12) AT 20μm

BINDING TO BSA (ROUND 12) AT 5μm

α-SYN ROUND 1:

BINDING TO α-SYN (ROUND 1) AT 20μm		BINDING TO α-SYN (ROUND 1) AT 5μm

α-SYN ROUND 8:

BINDING TO α-SYN (ROUND 8) AT 20μm		BINDING TO α-SYN (ROUND 8) AT 5μm

HEALTHY TISSUE ROUND 1:

BINDING TO HEALTHY TISSUE (ROUND 1) AT 5μm

HEALTHY TISSUE ROUND 10:

BINDING TO HEALTHY TISSUE (ROUND 10) AT 5μm

HEALTHY TDP-43 ROUND 1:

BINDING TO HEALTHY TDP-43 (ROUND 1) AT 5μm

HEALTHY TDP-43 ROUND 8:

BINDING TO HEALTHY TDP-43 (ROUND 8) AT 5μm

ALS TDP-43 CLONE 1:

BINDING TO ALS TDP-43 –              BINDING TO ALS TDP-43 –

BINDING TO HEALTHY TISSUE HOMOGENATE –      BINDING TO FTD TDP-43 – 20um

BINDING TO HEALTHY PROTEIN TDP-43 – 20um

ALS TDP-43 CLONE 2:

BINDING TO ALS TDP-43 –

BINDING TO ALS TDP-43 –

BINDING TO HEALTHY TISSUE HOMOGENATE –

BINDING TO FTD TDP-43 – 20um

BINDING TO HEALTHY PROTEIN TDP-43 – 20um

ALS TDP-43 CLONE 3:

BINDING TO ALS TDP-43 –

BINDING TO ALS TDP-43 –

BINDING TO HEALTHY TISSUE HOMOGENATE –

BINDING TO FTD TDP-43 – 20um

BINDING TO HEALTHY PROTEIN TDP-43 – 20um

FTD TDP-43 CLONE 1:

BINDING TO FTD TDP-43 AT 20μm

BINDING TO FTD TDP-43 AT 5μm

BINDING TO HEALTHY TISSUE AT 20μm

BINDING TO ALS TDP-43 AT 20μm

ANTIBODY BASED REAGENTS THAT SPECIFICALLY RECOGNIZE NEURODEGENERATIVE DISEASE RELATED FORMS OF THE PROTEIN TDP-43

RELATED APPLICATION

This application claims the benefit under 35 U.S.C. § 119(e) of U.S. Provisional Application No. 61/934,443, filed Jan. 31, 2014, the entire contents of which is hereby incorporated by reference.

FEDERALLY SPONSORED RESEARCH OR DEVELOPMENT

This invention was made with government support under AG042066 awarded by The National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 11, 2015, is named 17555.025WO1_SL.txt and is 38,778 bytes in size.

BACKGROUND OF THE INVENTION

Protein misfolding and aggregation is a common thread behind many neurodegenerative diseases, including AD, Parkinson's disease (PD), Frontal Temporal Dementia (FTD), Lewy Body Dementia (LBD), and Huntington's disease (HD) among others. While each disease has been primarily associated with aggregation of a specific protein; beta-amyloid (Aβ) with AD, alpha-synuclein (a-syn) with PD and LBD, tau with various tauopathies including AD and FTD, TDP-43 with amyotrophic lateral sclerosis (ALS) and FTD, and huntingtin with HD, more than one protein is likely to misfold and aggregate in brain tissue complicating diagnosis and treatment strategies. While all these proteins can form fibrillar aggregates, they can also form a variety of different smaller soluble aggregate structures as well, and increasing evidence implicates small soluble oligomeric forms of these different proteins as the relevant toxic species in the various diseases rather than the fibrillar aggregates that serve as diagnostic hallmarks. Since cellular stress induced by misfolding and aggregation of one protein such as Aβ may well lead to misfolding and aggregation of other proteins such as tau and a-syn, the presence of multiple misfolded proteins in different diseases should be expected. Therefore characterizing which aggregated protein species are present at different stages of each disease would greatly facilitate identification of suitable biomarkers and development of better diagnostic and treatment strategies for these neurodegenerative diseases.

Accordingly, there exists the need for new therapies and reagents for the diagnosis and treatment of frontotemporal dementia (FTD) and amyotrophic lateral sclerosis (ALS).

SUMMARY OF THE INVENTION

Variants of TDP-43 have been correlated with neurodegenerative diseases including Alzheimer's, Frontotemporal dementia and ALS (Lou Gehrig's disease). Reagents that can selectively recognize disease related variants have potential application as diagnostic and therapeutics for these diseases. The reagents also have potential value as imaging agents for specific diseases.

Antibody fragments or nanobodies have been isolates that selectively recognize variants of the protein TDP-43, a DNA binding protein that is involved in neurodegenerative disease. We have isolated nanobodies that selectively recognize TDP-43 variants that occur in cases of Frontotemporal Dementia and other nanobodies that selectively recognize TDP-43 variants that occur in cases of amyotrophic lateral sclerosis (ALS or Lou Gehrig's disease). Variants of TDP-43 have also been implicated in Alzheimer's disease.

The present invention provides in certain embodiments an antibody or antibody fragment that specifically recognizes TDP-43 associated with frontotemporal dementia (FTD), but not TDP-43 associated with amyotrophic lateral sclerosis (ALS) or TDP-43 associated with healthy human brain tissue.

The present invention provides in certain embodiments an antibody or antibody fragment that specifically recognizes TDP-43 associated with amyotrophic lateral sclerosis (ALS), but not TDP-43 associated with frontotemporal dementia (FTD) or TDP-43 associated with healthy human brain tissue.

The present invention provides in certain embodiments an antibody or antibody fragment isolated according to a method comprising the steps of:
  (a) negative panning a scFV phage library comprising serially contacting phage with:
    (i) a generic protein and/or α-synuclein (α-syn); and
    (ii) TDP-43 from healthy human brain tissue;
  until less than 5% of the phage is observed binding to antigen, which produces an aliquot of phage;
  (b) positive panning of the aliquot from step (a) comprising contacting the aliquot of phage from step (a) with TDP-43 associated with ALS or FTD, and incubating for time sufficient to allow binding of phage to the brain derived TDP-43 associated with ALS or FTD; and
  (c) eluting the bound phage particles from step (b). In certain embodiments, the step of observing of the binding of the phage to the antigen is by using Atomic Force Microscope (AFM) Imaging.

In certain embodiments, the antibody fragment is isolated according to a method comprising the steps of:
  (a) a negative panning of a scFV phage library wherein the negative panning eliminates phage that bind to non-desired antigens wherein the negative panning comprises serially contacting phage with:
    (i) a generic protein and/or α-synuclein (α-syn); and
    (ii) TDP-43 from healthy human brain tissue;
  and monitoring the binding of the phage to the generic protein and the TDP-43 from healthy human brain tissue using Atomic Force Microscope (AFM) Imaging and repeating steps (i) and (ii) until no phage is observed binding to antigen by the AFM imaging to produce an aliquot of phage;
  (b) contacting the aliquot of phage with TDP-43 associated with ALS or FTD and incubating for time sufficient to allow binding of phage to the oligomers; and
  (c) eluting the bound phage particles from step (b).

In certain embodiments, the TDP-43 associated with ALS or FTD is TDP-43 associated with ALS. In certain embodiments, the TDP-43 associated with ALS or FTD is TDP-43 associated with FTD.

In certain embodiments, generic protein is bovine serum albumin (BSA).

In certain embodiments, the negative panning is repeated until less than 0-10% phage was observed by AFM imaging as binding to antigen in step (a).

In certain embodiments, the antibody fragment does not contain the constant domain region of an antibody.

The present invention provides in certain embodiments an antibody fragment comprising an amino acid sequence encoded by a nucleic acid, wherein the nucleic acid has at least 80% identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, or SEQ ID NO:23.

The present invention provides in certain embodiments a binding molecule that binds to TDP-43 associated with ALS and does not bind TDP-43 from healthy human brain tissue or TDP-43 associated with FTD, wherein the binding molecule comprises an amino acid sequence encoded by a nucleic acid, wherein the nucleic acid has at least 80% identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, or SEQ ID NO:23.

The present invention provides in certain embodiments a method of binding TDP-43 associated with ALS comprising contacting a composition that comprises TDP-43 associated with ALS with an antibody, antibody fragment or binding molecule described above.

In certain embodiments, the TDP-43 associated with ALS is in a cell. In certain embodiments, the TDP-43 associated with ALS is in brain tissue.

The present invention provides in certain embodiments a method of binding TDP-43 associated with FTD comprising contacting a composition that comprises TDP-43 associated with FTD with an antibody, antibody fragment or binding molecule described above.

In certain embodiments, the TDP-43 associated with FTD is in a cell. In certain embodiments, the TDP-43 associated with FTD is in brain tissue.

The present invention provides in certain embodiments a method of detecting the presence of TDP-43 associated with FTD in a physiological sample comprising contacting a sample with an antibody, antibody fragment or a binding molecule of any one of claims 1 to 10 and determining the binding of the composition with the tissue sample wherein binding of the composition to the tissue sample is indicative of the presence of TDP-43 associated with FTD in the tissue sample wherein the presence of the TDP-43 associated with FTD is indicative of frontotemporal dementia.

The present invention provides in certain embodiments a method of detecting the presence of TDP-43 associated with ALS in a physiological sample comprising contacting a sample with an antibody, antibody fragment or a binding molecule of any one of claims 1 to 12 and determining the binding of the composition with the tissue sample wherein binding of the composition to the tissue sample is indicative of the presence of TDP-43 associated with ALS in the tissue sample wherein the presence of the TDP-43 associated with ALS is indicative of amyotrophic lateral sclerosis.

In embodiments, the physiological sample is brain tissue, serum, cerebrospinal fluid (CSF), blood, urine or saliva.

The present invention provides in certain embodiments a method of treating FTD or ALS in the brain of a mammal comprising administering to the mammal a composition comprising an antibody fragment or a binding molecule described above.

The present invention provides in certain embodiments an imaging composition specific for TDP-43 associated with ALS or FTD comprising an antibody fragment or a binding molecule described above conjugated to an imaging agent.

As used herein, the phrase "specifically recognizes TDP-43" indicates that it does not bind to or recognize non-specific proteins.

As used herein, the term "antibody" includes scFv (also called a "nanobody"), humanized, fully human or chimeric antibodies, single-chain antibodies, diabodies, and antigen-binding fragments of antibodies (e.g., Fab fragments). In certain embodiments, the antibody fragment does not contain the constant domain region of an antibody. In certain embodiments, the antibody fragment is less than 500 amino acids in length, such as between 200-450 amino acids in length, or less than 400 amino acids in length.

DETAILED DESCRIPTION OF THE INVENTION

Protein misfolding and aggregation is a common thread behind many neurodegenerative diseases including Frontotemporal Degeneration (FTD; also classified as frontotemporal lobar degeneration (FTLD)), Alzheimer's disease (AD), Lewy Body Dementia (LBD), Parkinson's disease (PD), Amyotrophic Lateral Sclerosis (ALS), and Huntington's disease (HD) among others. Numerous studies have implicated small soluble misfolded oligomeric aggregates of beta-amyloid (Aβ) in the progression of AD and similar aggregates of alpha-synuclein (a-syn) in the progression of PD and LBD. Increasing evidence also implicates similar misfolded oligomeric forms of tau in AD and other tauopathies such as FTD. Misfolding of other proteins including superoxide dismutase and huntingtin has also been correlated with different neurodegenerative diseases.

Recent evidence has suggested that cytoplasmic misfolding and aggregation of two additional proteins, TAR DNA binding protein 43 (TDP-43) and fused in sarcoma protein (FUS) associate with the pathology observed in a high percentage of FTD and ALS cases [8]. Therefore protein misfolding and aggregation is a key factor behind many neurodegenerative diseases and reagents which can recognize specific protein aggregate forms are needed to study the role of these proteins in disease onset and progression and to facilitate diagnoses. For example, as the focus on the role of Aβ in AD slowly shifted toward soluble Aβ aggregate species instead of insoluble fibrillar aggregates, reagents were needed that could specifically identify the variety of different aggregate species present. Because of the lack of reagents that could distinguish between different Aβ forms, many contradictory studies on the role of Aβ aggregation in AD were reported and progress on the role of Aβ in AD was significantly impeded. Increasing evidence indicates that aggregates of TDP-43 play a role in FTD, ALS and other neurodegenerative diseases including traumatic brain injury. Similar to other neuronal proteins including Aβ, a-syn and tau, TDP-43 is prone to form aggregate species, where TDP-43 mutations linked to increased risk of sporadic ALS aggregate more readily [9]. In order to facilitate identification of the role of TDP-43 in neurodegenerative disease, well characterized reagents that can specifically recognize the diversity of TDP-43 morphologies present in the human brain are critically needed to facilitate studies to identify the most promising TDP-43 forms for use as biomarkers of disease and to study pathogenic/pathophysiologic mechanisms.

Figure 1A:
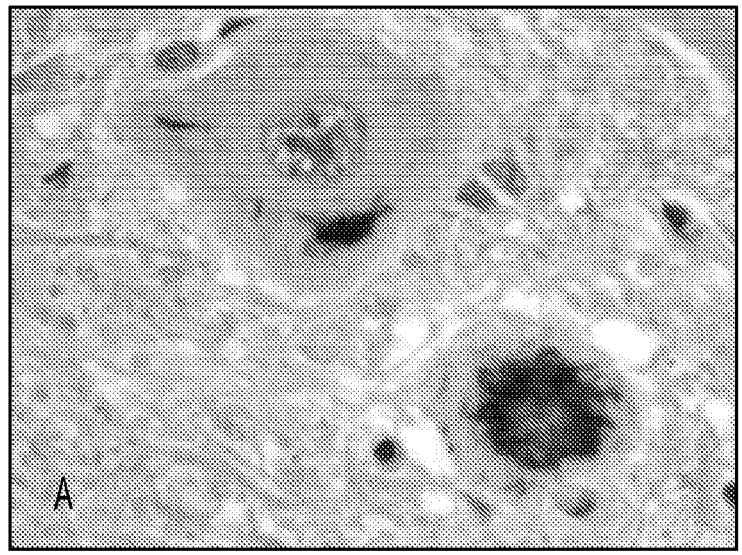
FIGS. 1A-1B. TDP-43 inclusion morphologies. A) Spinal cord motor neurons with cytoplasmic skein-like inclusions from patient with sporadic ALS (orig. mag. 400×, anti-TDP43 immunohistochemistry). B) Frontal cortex neuron with nuclear "cat-eye" inclusion from patient with FTD (orig. mag. 1000×).
Figure 1B:
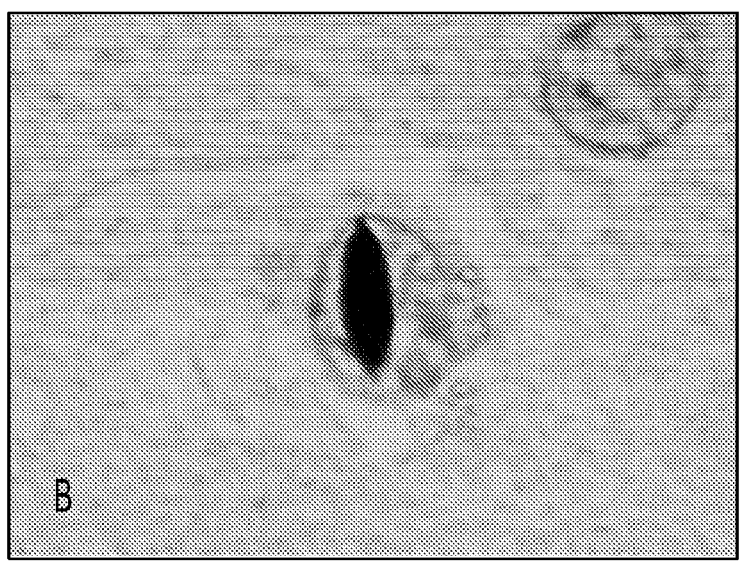

While misfolding of certain proteins has been associated with specific diseases, more than one protein is likely to misfold and aggregate in brain tissue complicating diagnosis and treatment strategies. Since cellular stress induced by misfolding and aggregation of one protein may well lead to misfolding and aggregation of other proteins, the presence of multiple misfolded proteins in different diseases should be expected. Therefore, there is likely a spectrum of diseases containing various different aggregated species targeting different cells and regions. Since the various neurodegenerative diseases may have overlapping features, characterizing which aggregated protein species are present at different stages of each disease would greatly facilitate identification of suitable biomarkers and development of better diagnostic and treatment strategies. While a number of biomarkers have shown promise for diagnosing different neurodegenerative diseases (reviewed in [10]), selected aggregate species of Aβ, a-syn and tau have been correlated with AD or PD (see for example ([11] [12, 13]) and may have value as selective biomarkers for neurodegenerative disease. It is likely that different species of TDP-43 can also serve as biomarkers for FTD [14] and other neurodegenerative diseases. TDP-43 is a DNA binding protein which has a number of different alternatively spliced forms [15]. TDP-43 binds to a variety of RNA and DNA sequences, particularly to poly-UG RNA sequences [16] accounting for its location in the nucleus, but can shuttle back and forth from the cytoplasm. In FTD and ALS cases, affected neurons and glial cells show a variety of different TDP-43 forms accumulate in inclusion bodies in the cytoplasm and/or nucleus with loss of the normal diffuse nuclear distribution (FIG. 1). TDP-43 accumulation occurs in different regions with different types of FTD [17], suggesting that TDP-43 aggregation can be a useful diagnostic biomarker for these diseases.

Presence of TDP-43 inclusions is also evident in a subset of AD cases, primarily in limbic regions [18, 19] where it can overlap with tau pathology [20]. FTD-43 pathology can be induced by increased expression of Aβ [21] providing additional evidence of the link between key aggregation prone proteins in the brain including Aβ, tau, a-syn, and TDP-43. There is therefore substantial evidence that aggregation of TDP-43 is an important factor in FTD, ALS and other neurodegenerative diseases. Aggregation of different protein species, including TDP-43, Aβ, a-syn and tau are important factors in many neurodegenerative diseases and detection of specific aggregate forms of TDP-43 in CSF or serum samples facilitate diagnosis of FTD and provide a means to monitor the effectiveness of therapeutic strategies. The present inventors developed novel technology that enables the isolation of single chain antibody fragments, or nanobodies, that selectively bind specific morphologies of a target protein. Nanobodies have been isolated that selectively recognize several different oligomeric forms of Aβ and others against different oligomeric forms of a-syn. The nanobodies can recognize the various target aggregates in human brain tissue and can readily distinguish between AD, PD and healthy tissue [1-7].

The present inventors have now developed reagents for detecting specific forms of TDP-43 that are present in FTD and ALS. The nanobodies specifically and selectively recognize the most relevant TDP-43 aggregate species associated with FTD. The reagents recognizing specific aggregate morphologies of TDP-43 are used in conjunction with other reagents recognizing specific morphologies of Aβ, a-syn, tau and FUS to distinguish FTD from other neurodegenerative diseases using CSF and/or serum samples.

A vast number of studies have correlated protein aggregation with neurodegenerative diseases including AD, Parkinson's and Dementia with Lewy Bodies. Numerous recent studies suggest that specific oligomeric forms of these proteins are involved in neuronal toxicity and can interfere with important functions including long term potentiation. Various soluble oligomeric species of Aβ and a-syn occur early during the course of AD and PD, and increasing evidence implicates oligomeric forms of tau in AD and other tauopathies.

Figure 2:
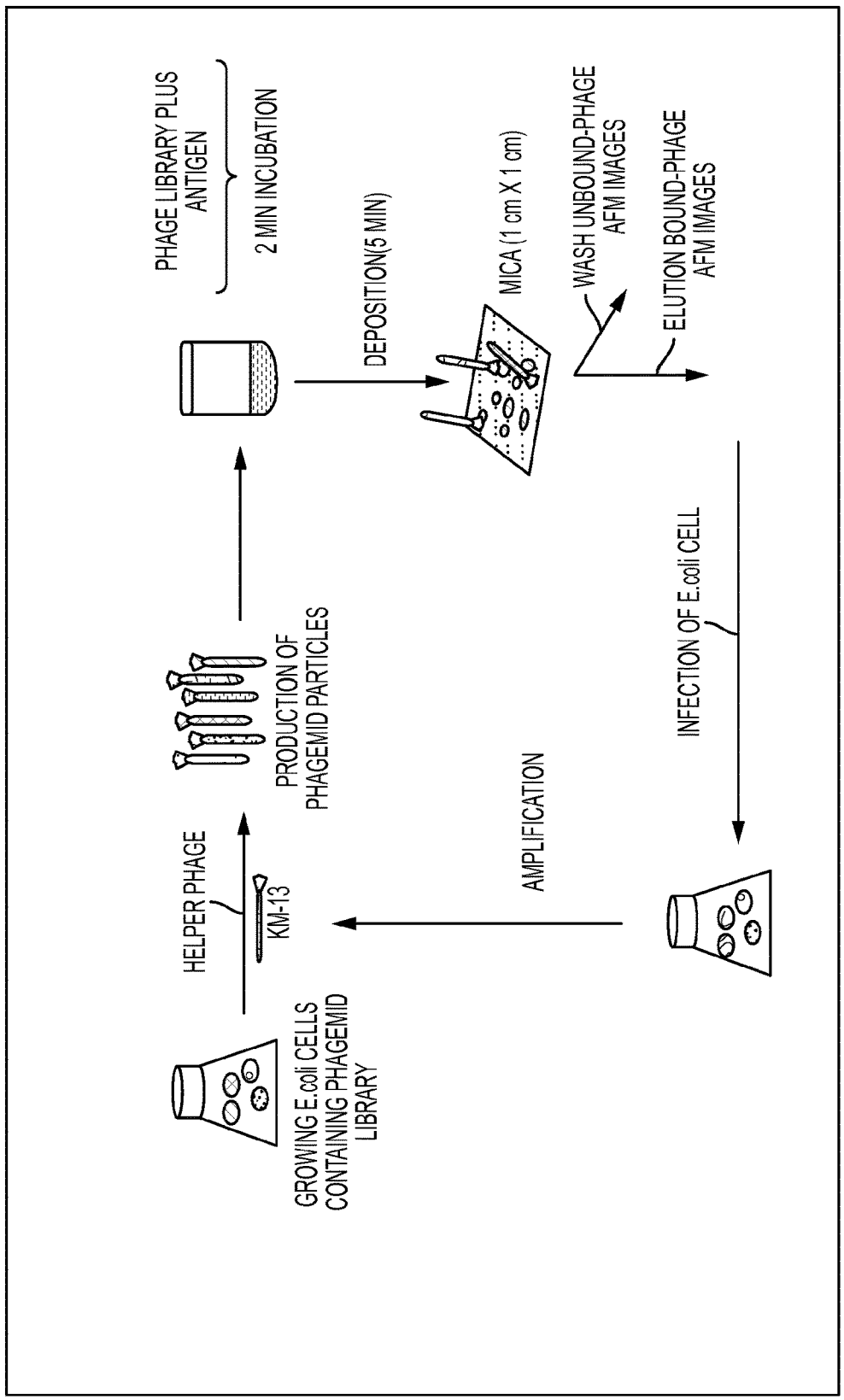
FIG. 2. Schematic of biopanning protocol. Phage are mixed with target antigen, deposited on mica, bound phage are attached to target antigen via antibody binding domain. Unbound phage are removed and bound phage recovered.

The inventors developed a novel biopanning technology that combines the imaging capability of Atomic Force Microscopy (AFM) with the diversity of antibody libraries (See FIG. 2). This unique combination of antibody diversity and imaging capability has enabled the isolation of single chain antibody variable domain fragment (scFv or nanobody) reagents to an array of morphologies of key proteins involved in neurodegenerative diseases including Aβ and alpha-synuclein (a-syn). Nanobodies were isolated that specifically recognize monomeric [4], fibrillar [1], and two different oligomeric a-syn morphologies [2, 3]. The anti-oligomeric a-syn nanobodies do not cross react with oligomeric Aβ, and specifically label PD brain tissue but not AD or healthy tissue [3]. In addition, nanobodies were isolated to different regions of full length Aβ [22] and to three distinct naturally occurring oligomeric Aβ morphologies [6, 23].

One, A4, specifically recognizes a larger oligomeric Aβ species, inhibits aggregation and extracellular toxicity of Aβ, does not cross react with oligomeric a-syn, and specifically labels Aβ aggregates in human AD brain samples, but not PD or healthy brain tissue [6]. A second nanobody, E1, recognizes a smaller trimeric or tetrameric Aβ species, and similar to A4 inhibits aggregation and extracellular toxicity of Aβ, does not cross react with oligomeric a-syn, and labels Aβ aggregates in human AD but not healthy brain tissue [23]. Utilizing an AD brain derived oligomeric Aβ preparation [24, 25], a third nanobody was isolated, C6, that specifically recognizes oligomeric Aβ species derived from human AD brain tissue, but does not recognize Aβ aggregates generated in vitro. The different specificities of each nanobody can be readily observed when each nanobody is expressed on the surface of a filamentous bacteriophage and antibody/antigen complexes are imaged by AFM [23]. Therefore, the combination of antibody libraries and AFM imaging technologies enabled the isolation and characterization of reagents that recognize specific protein variants including four different naturally occurring aggregated forms of a-syn and four different naturally occurring aggregated forms of Aβ.

Another powerful advantage of the present AFM panning protocol is that not only can reagents be isolated and characterized to specific protein morphologies, but this can be done using only picograms or less of material. In addition the sample does not need to be purified, and the protein does not need to be chemically modified in any way. Nanobodies were actually isolated against a single molecule of the target antigen [26]. This unique combination of capabilities to isolate different TDP-43 isoforms and to generate and characterize reagents that specifically recognize individual protein variants provides the means to generate reagents that specifically recognize an array of different TDP-43 variants present in human FTD and ALS brain tissue.

While reagents already exist that can recognize TDP-43, these reagents cannot distinguish between different aggregated states of the protein. Reagents that can detect specific forms of TDP-43 can provide very powerful tools to facilitate diagnosis of ALS, FTD and other neurodegenerative diseases, and to follow progression of these diseases or to evaluate therapeutic strategies. While many neurodegenerative diseases have overlapping clinical symptoms and cellular and biochemical mechanisms such as an increase in inflammatory markers, and aggregation of similar proteins, the reagents developed by the inventors have well defined specificities and selectivities for selected TDP-43 forms and facilitate specific diagnoses of ALS, and FTD and other neurodegenerative diseases. In combination with other protein and morphology specific reagents against Aβ and a-syn aggregate species [1-3, 6], these reagents are used to identify disease specific biomarkers which can readily detect and distinguish many related neurodegenerative diseases including ALS, FTD, AD, PD, and LBD.

The present inventors have developed novel technology that enables the isolation of single chain antibody fragments, or nanobodies, that selectively bind specific morphologies of a target protein. Nanobodies have been isolated that selectively recognize several different oligomeric forms of Aβ or a-syn and showed that the nanobodies recognize aggregates present in diseased but not healthy tissue [1-7].

The inventors have developed selective reagents that can identify which aggregate morphologies of TDP-43 are specific for diseased human FTD and ALS brain issue/biofluids, and which of these TDP-43 species represent the best diagnostic targets. In this proposal we will separate different aggregate TDP-43 species present in human FTD and ALS brain tissue, generate antibody based reagents (nanobodies) that selectively bind the different TDP-43 aggregate species, and then use the nanobodies to identify which TDP-43 forms can distinguish between human FTD, ALS and healthy brain tissue. We will generate nanobodies that recognize human brain derived aggregate forms of TDP-43, and utilize these nanobodies to identify which TDP-43 forms are present in diseased human CSF and brain tissue. The hypothesis is that aggregation of TDP-43 is an early event in FTD and ALS, and that this process can be detected using well characterized nanobodies that selectively recognize specific TDP-43 aggregate forms.

To achieve the goal of developing nanobodies that specifically and selectively recognize the most relevant TDP-43 aggregate species associated with FTD and ALS, the inventors isolated different size oligomeric TDP-43 species from human FTD and ALS brain tissue, generated and characterized nanobodies against specific brain derived TDP-43 forms isolated from FTD and ALS brain tissue, and identified TDP-43 morphology specific nanobodies that distinguish between brain tissue from FTD, ALS and healthy human post-mortem cases.

The inventors generated nanobody reagents that selectively recognized variants of TDP-43 that are associated with FTD or ALS. Identification of TDP-43 forms that can be used for diagnosis and staging of FTD and ALS and potentially other neurodegenerative diseases provide valuable biomarkers for disease diagnosis and progression, and identify potential therapeutic targets. The morphology specific nanobodies developed here serve as valuable reagents in various biosensor formats to detect specific TDP-43 morphologies for diagnostic tests or to follow disease progression or as reagents to specifically target toxic TDP-43 species for intracellular and extracellular therapeutic applications. While reagents already exist that can recognize TDP-43, the prior reagents cannot distinguish between different aggregated states of the protein. The nanobody reagents presently developed are used either extra- or intracellularly to identify or target specific TDP-43 morphologies involved in the onset and progression of ALS and FTD. The reagents are also used in conjunction with other reagents recognizing specific morphologies of Aβ, a-syn and tau to characterize the concentration profiles of these markers in CSF and/or serum samples from patients with various neurodegenerative diseases and to monitor the progression of these diseases.

In the present invention, using a bio-panning protocol to identify single chain antibody fragments (scFv, also called nanobodies) against low (pico-molar) quantities of specific TDP-43 morphologies, the inventors identified binding reagents with therapeutic and diagnostic properties. Specifically, the inventors have generated single chain antibody fragments (scFvs or nanobodies) that selectively recognize specific morphologies of the protein TDP-43. These isolated scFvs that have potential value as diagnostics, therapeutics and imaging agents for neurodegeneration. As diagnostics, these antibody fragments can be used to detect the presence of specific morphologies of the protein TDP-43 in serum, CSF or other fluid samples as a presymptomatic indication of neurodegeneration. Specific morphologies of the protein TDP-43 may be an indicator of particular neurodegenerative diseases. The antibody fragments can also be used as therapeutics to selectively target the specific morphologies of the protein TDP-43. Finally, the reagents can also be used as imaging agents to detect the presence of specific morphologies of the protein TDP-43 in vivo. The antibody fragments can be readily labeled for PET scans or other imaging techniques.

The biopanning studies were performed to isolate single chain variable fragments (nanobodies) against the different TDP-43 species. The biopanning protocol that was used combines the imaging capabilities of AFM with the binding diversity of phage-displayed antibody technology.

In a broad sense the scFv compositions of the present invention may be described as compounds that are binding compounds specific for target morphologies of TDP-43. These compounds may therefore be used in diagnostic as well therapeutic applications and may be either administered to patients or used on patient tissue samples. In some embodiments, the compositions of the present invention may be used for in vivo imaging of target morphologies of TDP-43, and distinguish between neurological tissue with forms of TDP-43 associated with ALS or FTD, and TDP-43 associated with normal neurological tissue. As such the nanobody compositions of the invention may be used to detect and quantitate TDP-43 in diseases including, for example, ALS and frontotemporal dementia. In another embodiment, the compounds may be used in the treatment or prophylaxis of neurodegenerative disorders. Also provided herein are methods of allowing the compound to distribute into the brain tissue, and imaging the brain tissue, wherein an increase in binding of the compound to the brain tissue compared to a normal control level of binding indicates that the mammal is suffering from or is at risk of developing a neurodegenerative disease, such as ALS or frontotemporal dementia.

The methods of the present invention are conducted to provide early stage diagnosis of ALS and FTD. As explained herein the nanobodies of the invention are ones that specifically recognize TDP-43 associated with ALS or FTD. Thus, compositions comprising these antibodies and antibody fragments may be used to identify the presence of TDP-43 associated with ALS or FTD in a biological sample from a patient to be tested for a neurodegenerative disease, wherein the presence of TDP-43 associated with ALS or FTD in the sample is indicative that the patient has or is likely to develop ALS or FTD. In certain embodiments, the assay format that is used may be any assay format that typically employs antibody compositions. Thus, for example, the biological sample may be examined using immunohistology techniques, ELISA, Western Blotting, and the like.

For purposes of the diagnostic methods of the invention, the compositions of the invention may be conjugated to a detecting reagent that facilitates detection of the scFv. For example, example, the detecting reagent may be a direct label or an indirect label. The labels can be directly attached to or incorporated into the detection reagent by chemical or recombinant methods.

In one embodiment, a label is coupled to the scFv through a chemical linker. Linker domains are typically polypeptide sequences, such as poly gly sequences of between about 5 and 200 amino acids. In some embodiments, proline residues are incorporated into the linker to prevent the formation of significant secondary structural elements by the linker. In certain embodiments, linkers are flexible amino acid subsequences that are synthesized as part of a recombinant fusion protein comprising the RNA recognition domain. In one embodiment, the flexible linker is an amino acid subsequence that includes a proline, such as Gly(x)-Pro-Gly(x) where x is a number between about 3 and about 100 (SEQ ID NO: 29). In other embodiments, a chemical linker is used to connect synthetically or recombinantly produced recognition and labeling domain subsequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

The detectable labels can be used in the assays of the present invention to diagnose a neurodegenerative disease, such as ALS or FTD, these labels are attached to the scFvs of the invention, can be primary labels (where the label comprises an element that is detected directly or that produces a directly detectable element) or secondary labels (where the detected label binds to a primary label, e.g., as is common in immunological labeling). An introduction to labels, labeling procedures and detection of labels is found in Polak and Van Noorden (1997) Introduction to Immunocytochemistry, 2nd ed., Springer Verlag, N.Y. and in Haugland (1996) Handbook of Fluorescent Probes and Research Chemicals, a combined handbook and catalogue Published by Molecular Probes, Inc., Eugene, Oreg. Patents that described the use of such labels include U.S. Pat. Nos. 3,817,837; 3,850,752; 3,939,350; 3,996,345; 4,277,437; 4,275,149; and 4,366,241.

Primary and secondary labels can include undetected elements as well as detected elements. Useful primary and secondary labels in the present invention can include spectral labels such as green fluorescent protein, fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., $^{3}$H, $^{125}$I, $^{35}$S, $^{14}$C, $^{32}$P, $^{33}$P, etc.), enzymes (e.g., horse radish peroxidase, alkaline phosphatase etc.), spectral calorimetric labels such as colloidal gold or colored glass or plastic (e.g. polystyrene, polypropylene, latex, etc.) beads. The label can be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions.

Exemplary labels that can be used include those that use: 1) chemiluminescence (using horseradish peroxidase and/or alkaline phosphatase with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate (kits available from Life Technologies/Gibco BRL, and Boehringer-Mannheim)); 3) fluorescence using, e.g., an enzyme such as alkaline phosphatase, together with the substrate AttoPhos (Amersham) or other substrates that produce fluorescent products, 4) fluorescence (e.g., using Cy-5 (Amersham), fluorescein, and other fluorescent tags); 5) radioactivity. Other methods for labeling and detection will be readily apparent to one skilled in the art.

Where the scFv-based compositions of the invention are contemplated to be used in a clinical setting, the labels are preferably non-radioactive and readily detected without the necessity of sophisticated instrumentation. In certain embodiments, detection of the labels will yield a visible signal that is immediately discernable upon visual inspection. One example of detectable secondary labeling strategies uses an antibody that recognizes TDP-43 associated with ALS or FTD in which the antibody is linked to an enzyme (typically by recombinant or covalent chemical bonding). The antibody is detected when the enzyme reacts with its substrate, producing a detectable product. In certain embodiments, enzymes that can be conjugated to detection reagents of the invention include, e.g., β-galactosidase, luciferase, horse radish peroxidase, and alkaline phosphatase. The chemiluminescent substrate for luciferase is luciferin. One embodiment of a fluorescent substrate for β-galactosidase is 4-methylumbelliferyl-β-D-galactoside. Embodiments of alkaline phosphatase substrates include p-nitrophenyl phosphate (pNPP), which is detected with a spectrophotometer; 5-bromo-4-chloro-3-indolyl phosphate/ nitro blue tetrazolium (BCIP/NBT) and fast red/napthol AS-TR phosphate, which are detected visually; and 4-methoxy-4-(3-phosphonophenyl) spiro[1,2-dioxetane-3, 2'-adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer, and 3,3,5,5'-tetramethylbenzidine (TMB), 3,3' diaminobenzidine (DAB), 3-amino-9-ethylcarbazole (AEC), and 4-chloro-1-naphthol (4C1N), which are detected visually. Other suitable substrates are known to those skilled in the art. The enzyme-substrate reaction and product detection are performed according to standard procedures known to those skilled in the art and kits for performing enzyme immunoassays are available as described above.

The presence of a label can be detected by inspection, or a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

As noted herein throughout the scFvs of the invention are targeted specifically to TDP-43 associated with ALS or FTD. As such, the scFvs of the invention also may be used to specifically target therapeutic compositions to the sites of aggregation of TDP-43 associated with ALS or FTD. In this embodiment, any therapeutic agent typically used for the treatment of these diseases, may be conjugated to scFvs in order to achieve a targeted delivery of that therapeutic agent.

The scFv compositions of the invention can be used in any diagnostic assay format to determine the presence of TDP-43 associated with ALS or FTD. A variety of immunodetection methods are contemplated for this embodiment. Such immunodetection methods include enzyme linked immunosorbent assay (ELISA), radioimmunoassay (RIA), immunoradiometric assay, fluoroimmunoassay, chemiluminescent assay, bioluminescent assay, and Western blot, though several others are well known to those of ordinary skill. The steps of various useful immunodetection methods have been described in the scientific literature.

In general, the immunobinding methods include obtaining a sample suspected of containing a protein, polypeptide and/or peptide (in this case TDP-43 associated with ALS or FTD), and contacting the sample with a first antibody, monoclonal or polyclonal, in accordance with the present invention, as the case may be, under conditions effective to allow the formation of immunocomplexes.

The immunobinding methods include methods for detecting and quantifying the amount of the TDP-43 associated with ALS or FTD in a sample and the detection and quantification of any immune complexes formed during the binding process. Here, one would obtain a sample suspected of containing TDP-43 associated with ALS or FTD, and contact the sample with an antibody fragment of the invention, and then detect and quantify the amount of immune complexes formed under the specific conditions.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those scFv molecules specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939, 350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

As noted above, an scFv of the invention may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the scFV is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first step biotinylated, monoclonal or polyclonal antibody (in the present example a scFv of the invention) is used to detect the target antigen(s), and a second step antibody is then used to detect the biotin attached to the complexed nanobody. In this method the sample to be tested is first incubated in a solution containing the first step nanobody. If the target antigen is present, some of the nanobody binds to the antigen to form a biotinylated nanobody/antigen complex. The nanobody/antigen complex is then amplified by incubation in successive solutions of streptavidin (or avidin), biotinylated DNA, and/or complementary biotinylated DNA, with each step adding additional biotin sites to the nanobody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the method described above up to the incubation with biotinylated DNA. However, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

The diagnostic assay format that may be used in the present invention could take any conventional format such as ELISA or other platforms such as luminex or biosensors.

The present invention shows the sequence of certain exemplary DNA sequences for binding agents specific for TDP-43 associated with ALS or FTD. These sequences can readily be modified to facilitate diagnostic assays, for example a tag (such as GFP) can be added to these scFvs to increase sensitivity. In one exemplary ELISA, antibodies are immobilized onto a selected surface exhibiting protein affinity, such as a well in a polystyrene microtiter plate. Then, a test composition suspected of containing TDP-43 associated with ALS or FTD, such as a clinical sample (e.g., a biological sample obtained from the subject), is added to the wells. After binding and/or washing to remove non-specifically bound immune complexes, the bound antigen may be detected. Detection is generally achieved by the addition of another antibody that is linked to a detectable label. This type of ELISA is a simple "sandwich ELISA." Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and/or then contacted with binding agents (e.g., scFvs of the invention). After binding and/or washing to remove non-specifically bound immune complexes, the bound anti-binding agents are detected. Where the initial binding agents are linked to a detectable label, the immune complexes may be detected directly. Again, the immune complexes may be detected using a second antibody that has binding affinity for the first binding agents, with the second antibody being linked to a detectable label.

Another ELISA in which the antigens are immobilized, involves the use of antibody competition in the detection. In this ELISA, labeled antibodies (or nanobodies) against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes.

In coating a plate with either TDP-43 associated with ALS or FTD or an scFv of the invention, one will generally incubate the wells of the plate with a solution of the antigen or scFvs, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the TDP-43 associated with ALS or FTD and/or scFv composition with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. An example of a washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. This may be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In various aspects of the invention, it will be desirable to further subject patients to more traditional diagnostic approaches for ALS or FTD.

As noted above, there are various drugs that are presently in use or under development for the treatment of ALS and frontotemporal dementia. The present invention contemplates the use of scFvs of the invention, based "diagnostic" methods to further assess the efficacy of treatments. Given the role of TDP-43 associated with ALS or FTD in these diseases, the ability of a particular therapy to reduce the amount of TDP-43 associated with ALS or FTD will be indicative of an effective treatment.

The present invention may involve the use of pharmaceutical compositions which comprise an agent conjugated to a scFv of the invention for delivery into a subject having ALS or frontotemporal dementia. Such an agent will ideally be formulated into a pharmaceutically acceptable carrier. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. Except insofar as any conventional carrier is incompatible with the active ingredient, its use in the therapeutic or pharmaceutical compositions is contemplated.

An amino acid sequence of an antibody or antibody fragment or variant thereof described herein or a nucleic acid sequence or variant thereof encoding such an amino acid sequence, is a sequence that is substantially similar to SEQ ID NO:1, SEQ ID NO:2, SEQ ID NO:3, SEQ ID NO:4, SEQ ID NO:5, or SEQ ID NO:6. Variant amino acid and nucleic acid sequences include synthetically derived amino acid and nucleic acid sequences, or recombinantly derived amino acid or nucleic acid sequences. Generally, nucleic acid or amino acid sequences of the invention will have at least 40 to 100% sequence identity to SEQ ID NO:1, SEQ ID NO:2, SEQ ID NO:3, SEQ ID NO:4, SEQ ID NO:5, or SEQ ID NO:6. In certain embodiments, the nucleic acid or amino acid sequences of the invention will have at least 50, 60, 70%, 71%, 72%, 73%, 74%, 75%, 76%, 77%, 78% 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO:1, SEQ ID NO:2, SEQ ID NO:3, SEQ ID NO:4, SEQ ID NO:5, or SEQ ID NO:6.

"Variants" are intended to include sequences derived by deletion (so-called truncation) or addition of one or more amino acids to the N-terminal and/or C-terminal end, and/or addition of one or more bases to the 5' or 3' end of the nucleic acid sequence; deletion or addition of one or more amino acids/nucleic acids at one or more sites in the sequence; or substitution of one or more amino acids/nucleic acids at one or more sites in the sequence. The antibodies and antibody fragments described herein may be altered in various ways including amino acid substitutions, deletions, truncations, and insertions. Methods for such manipulations are generally known in the art. For example, amino acid sequence variants of the enzyme can be prepared by mutations in the DNA. Methods for mutagenesis and nucleotide sequence alterations are well known in the art. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall enzyme retains its spatial conformation but has altered biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains.

As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

EXAMPLES

Example 1

Preparation of Brain Derived TDP-43 Aggregates

TDP-43's role in normal cell biology and in neuropathological processes in not well understood. Aberrant localization in the cytoplasm or in nuclear aggregates is seen in regionally specific glia and neurons in both sporadic and some familial forms of ALS and FTDs [8, 31]. Several reports have looked at TDP-43 as a biomarker and measured elevated CSF and plasma levels in some subsets of patients with FTD and ALS, though sensitivity and specificity has been a problem (reviewed in [32, 33]). Appropriate normal and disease cases were identified and TDP-43 aggregates were purified by immunoprecipitation. Next, nanobodies were generated against the different TDP-43 variants. Third, the nanobodies were used to identify which forms of TDP-43 best distinguished ALS, FTD and healthy brain tissue.

Purification and Characterization of Oligomeric TDP-43.

The different monomeric and aggregated species of TDP-43 were purified from normal brain, FTLD-TDP [34], sporadic ALS, and ALS-FTD brain specimens. Samples were chosen from affected regions of frontal or temporal cortex and confirmed to have abundant numbers of TDP-43 aggregates by standard immunohistochemistry in adjacent FFPE tissues. A simple semiquantitative scoring scheme for TDP-43 aggregate burden in tissue has recently been reported in an interesting case report [31] and was recorded for each sample. Recording of types of inclusions and cells affected was also be done (i.e., cytoplasmic, nuclear, neuronal, glial). Post-mortem samples have been deidentified for all personal patient information and have confirmed neuropathological diagnoses and reports available. Samples were chosen for post-mortem intervals less than 24 hours (optimally less than 12 hours). Brain tissue was maintained at −80° C. until use.

Three to five cases for each group were selected, and immunoprecipitation for TDP-43 samples from each group was prepared using standard methods as described recently [35]. Briefly, frozen cortical samples were homogenized in cold lysis buffer: 25 mM HEPES-NaOH (pH 7.9), 150 mM NaCl, 1.5 mM $MgCl_2$, 0.2 mM EDTA, 0.5% Triton-X-100, 1 mM dithiothreitol, protease inhibitor cocktail. The lysate was incubated with 50 µl of Dynabeads (Protein-G beads, Invitrogen) according to manufacturer protocol. In the first stage, beads were coated with anti-TDP-43 polyclonal (ProteinTech, Chicago, Ill., USA). After subsequent washing, the beads were incubated overnight at 4° C. with 400 mg of cell lysate. The beads were rinsed twice with PBS and antibody-bound complexes are eluted by boiling in SDS loading buffer (0.5 mM Tris-HCl pH: 6.8; 10% SDS; 5% Glycerol). Samples were frozen down. Proteins were also resolved by 10% SDS-PAGE and transferred on nitrocellulose membrane (Biorad, Hercules, Calif., USA). The membrane was incubated with anti-TDP-43 antibody, and immunoreactive proteins were visualized by chemilluminescence (Perkin and Elmer, Santa Clara, Calif., USA).

Generation and Characterization of Nanobodies Against Specific Brain Derived TDP-43 Forms Isolated from FTD and ALS Brain Tissue.

Protocols have been developed that enable the ready isolation of individual clones from phage display libraries that recognize specific protein morphologies. Panning protocols have continued to be refined to facilitate isolation of reagents against targets that are available in limited amounts, that cannot be purified or that are unstable. Results have been reported for the isolation of nanobodies against monomeric, fibrillar and two different oligomeric forms of a-syn, and monomeric, fibrillar and two different oligomeric β-amyloid species using the basic protocol illustrated in FIG. 2 [1-4, 6, 7, 22, 23, 36]. The isolation of a nanobody against a third distinct oligomeric beta-amyloid morphology has also been accomplished. The inventors have now included additional negative panning steps to remove non-specific and undesired binding activities, so virtually all clones isolated after only a single round of panning specifically recognize the target antigen. Using this technique, the inventors were able to isolate various morphology specific ligands using only nanograms of target. The inventors have also developed AFM based protocols to characterize ligand binding [37], so not only were they able to isolate morphology specific ligands with only minimal material, but they were able to characterize binding specificity with limited material as well. This unique capability is ideally suited to isolating ligands against specific protein morphologies.

AFM Panning Against TDP-43 Aggregates.

Similar protocols were used to isolate nanobodies to the brain derived TDP-43 aggregate morphologies as described previously [1-3, 6]. Only nanogram amounts of material was needed for the panning protocols, so minimal amounts of material were needed for the panning process. To ensure that the nanobodies isolated from the panning protocol selectively recognized FTD or ALS brain derived TDP-43 aggregate species, a series of negative panning steps were performed prior to the positive selection on the brain derived samples. First, a negative panning step was utilized on the control protein BSA to remove all non-specific sticky nanobodies. Next, a negative panning step using control non-diseased brain sample that was prepared similarly to the disease brain samples was used to remove nanobodies binding to non-disease associated forms of TDP-43 and any brain proteins that may purify with TDP-43. Finally, a third negative panning step using synthetic monomeric TDP-43 (Proteintech) was used to remove all nanobodies against monomeric TDP-43. AFM was utilized to verify that all phage binding to the non-target samples have been removed for each negative panning step. An aliquot of the remaining phage was added to mica containing an aliquot of the non-target sample and unbound phage were removed. If any phage were observed still binding to the off target samples, a second round of negative panning was performed. The process was repeated until no remaining phage bind the off target sample. After the negative panning steps, the remaining phage were added to an aliquot of either the positive FTD or ALS brain derived TDP-43 aggregate sample and positive clones recovered as described [1-3, 6, 23, 38, 39].

Nanobody Characterization.

There are numerous techniques that can be used to determine binding specificity of each of the nanobodies isolated against the different target TDP-43 morphologies depending on the availability and stability of the target antigen. In characterizing binding specificity, many of the same problems that were encountered in biopanning arise again, the primary one being that it is difficult to determine nanobody binding specificity to aggregate morphologies that are present in small amounts, that may be difficult to purify or that are not amenable to standard immobilization protocols. To address these problems, the inventors utilized the capabilities of AFM to develop new techniques that enabled the characterization of binding specificity of nanobodies to different target protein morphologies using minimal material and without the need for any modification. Therefore it was possible to employ a variety of different binding assays depending on how much of the target protein morphology can be purified, whether it can be purified to homogeneity or not, and how stable the particular target morphology was. The results we have obtained with the various assays are described.

Specificity Using Biacore, ELISA, Western Blot or Dot Blot.

For those TDP-43 morphologies that were obtained in reasonable quantity, it was possible to determine accurate binding kinetics by surface plasmon resonance using a BIAcore X biosensor. Since chemical immobilization may affect various aggregated protein morphologies, it is possible to determine binding specificity by ELISA, western or dot blot, depending on how easy it is to purify the target aggregate morphology. The protocols for each of these assays are routinely used [2, 4, 7, 22, 36, 40, 41].

Specificity Using AFM.

For certain of the aggregated TDP-43 samples, it is not possible to determine nanobody specificity by conventional means such as western blot as described above. Several different AFM based methods have been developed and used to determine antibody specificity for antigen targets that are not suitable for analysis as described above, or that are available in only limited amounts.

Figure 3:
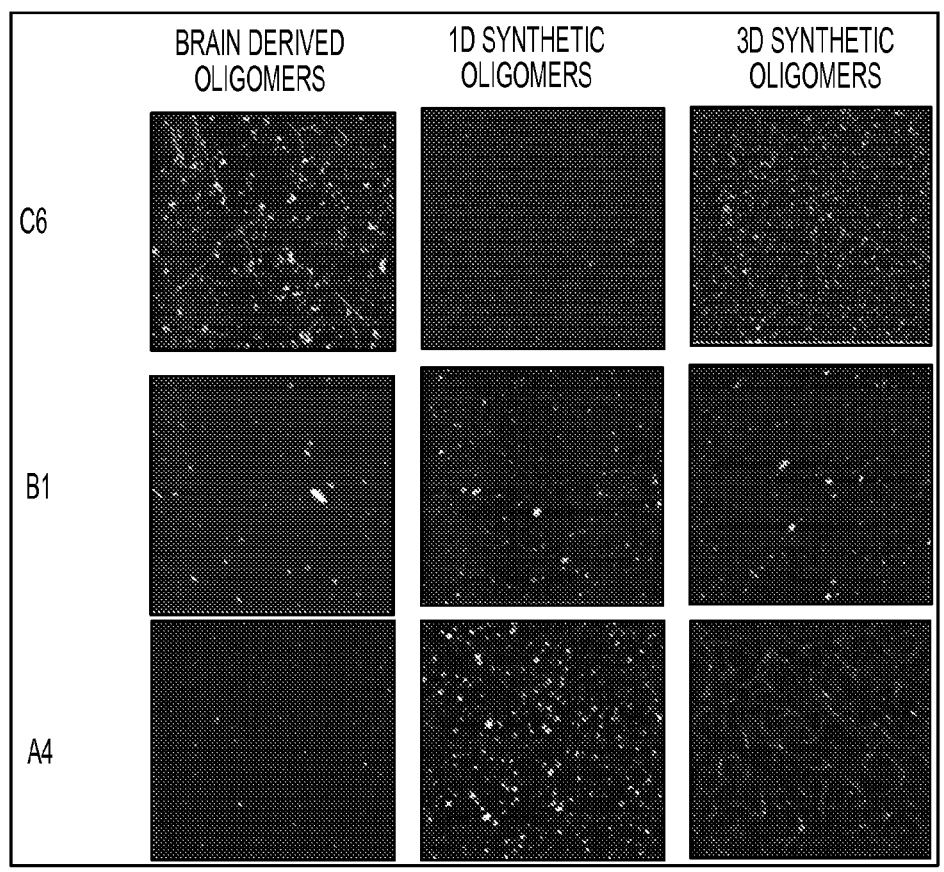
FIG. 3. AFM images of different anti-oligomeric Aβ phage displayed nanobodies. C6 binds only to brain derived oligomers, E1 to 1 day synthetic oligomers and A4 to 3 day synthetic oligomers. Phage appear as filaments, oligomeric Aβ as small white dots.
Figure 4A:
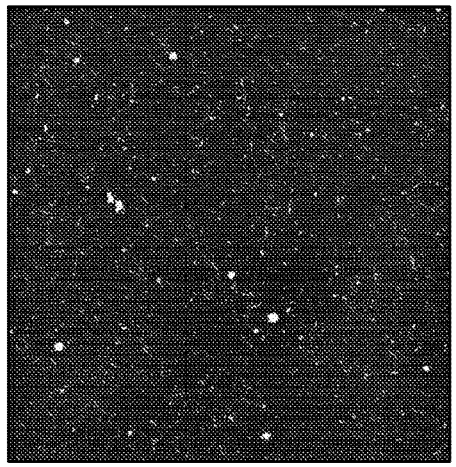
FIGS. 4A-4D. 4A. Negative Panning Against Bovine Serum Albumin. 4B. Negative Panning Against Alpha-Synuclein. 4C. Negative Panning Against Healthy Homogenized Human Brain Tissue. 4D. Negative Panning Against Healthy TDP-43.
Figure 4A:
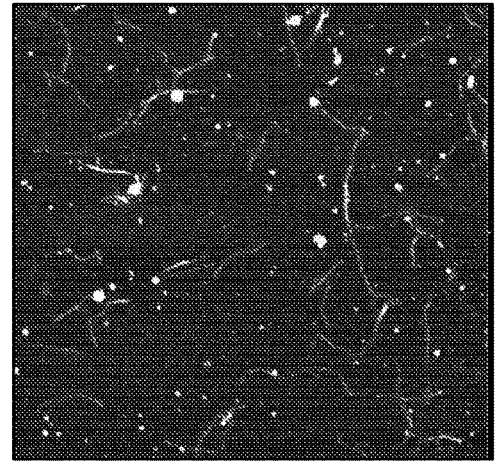
Figure 4A:
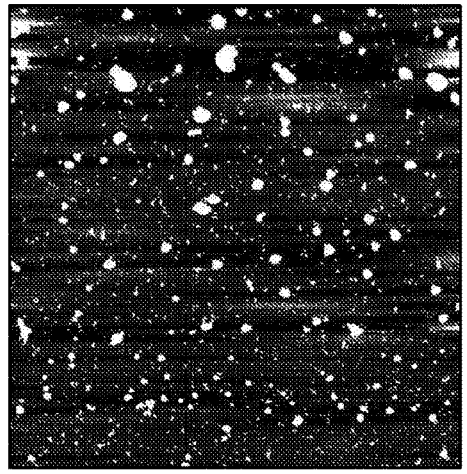
Figure 4A:
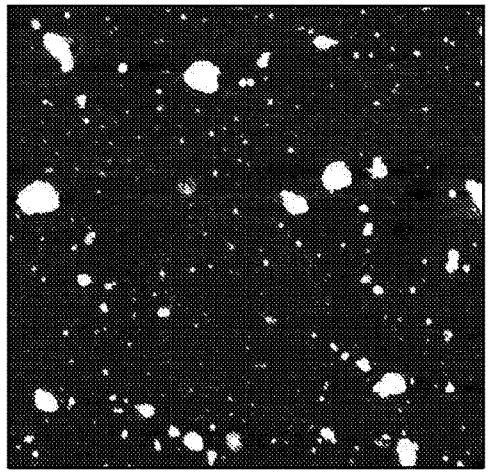
Figure 4B:
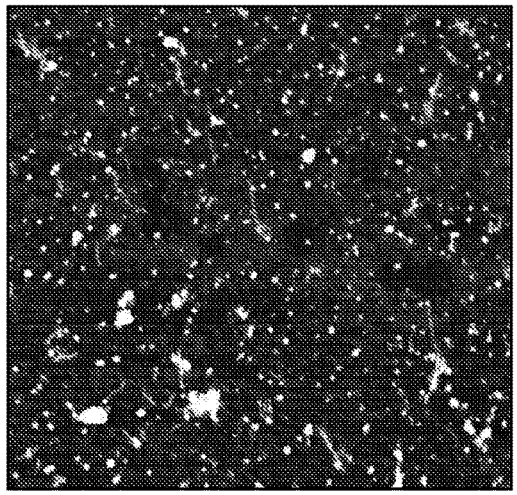
Figure 4B:
Figure 4B:
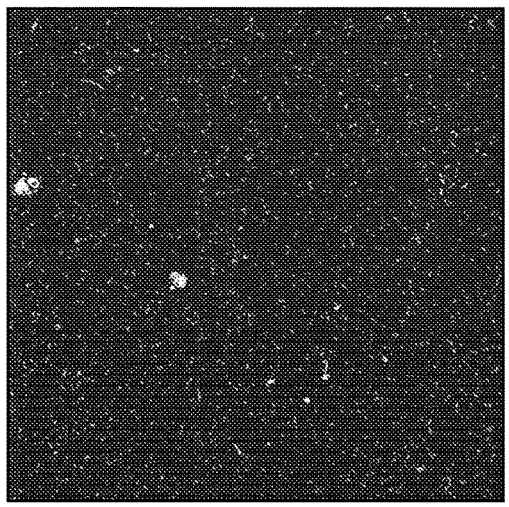
Figure 4B:
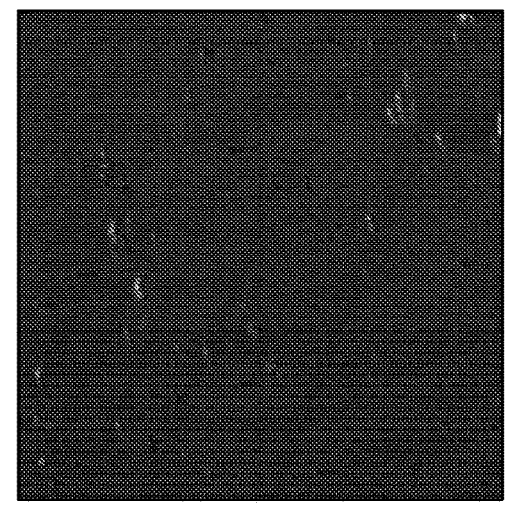
Figure 4C:
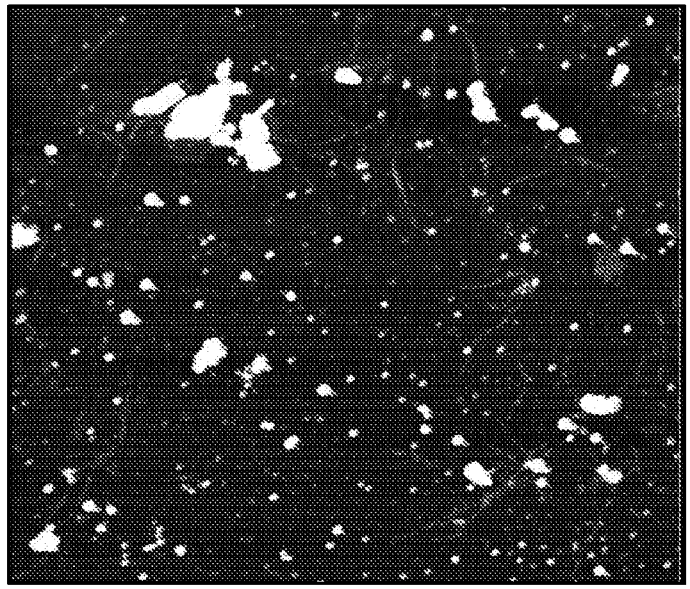
Figure 4C:
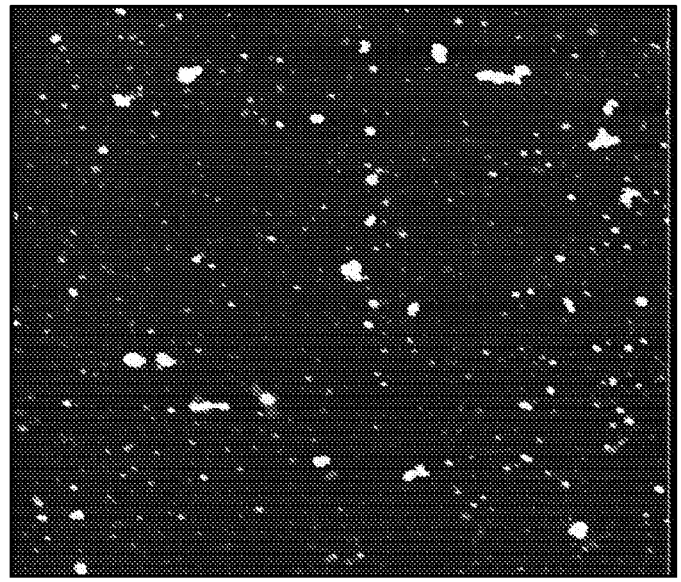
Figure 4D:
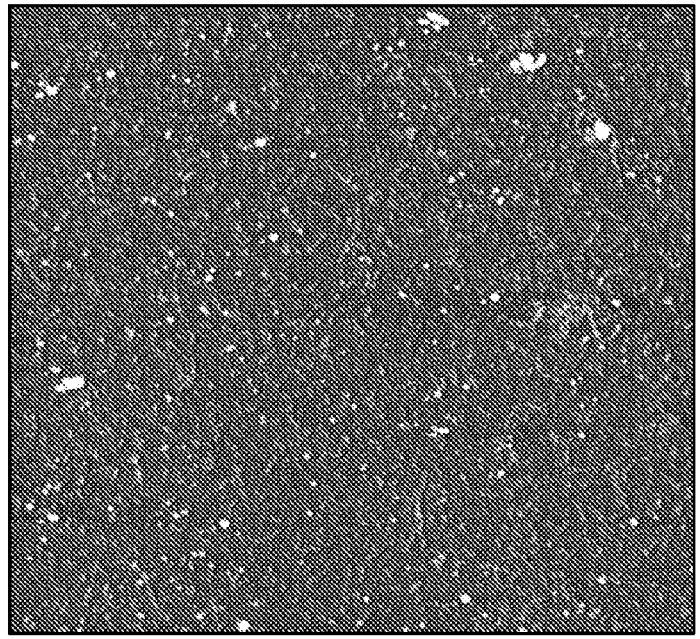
Figure 4D:
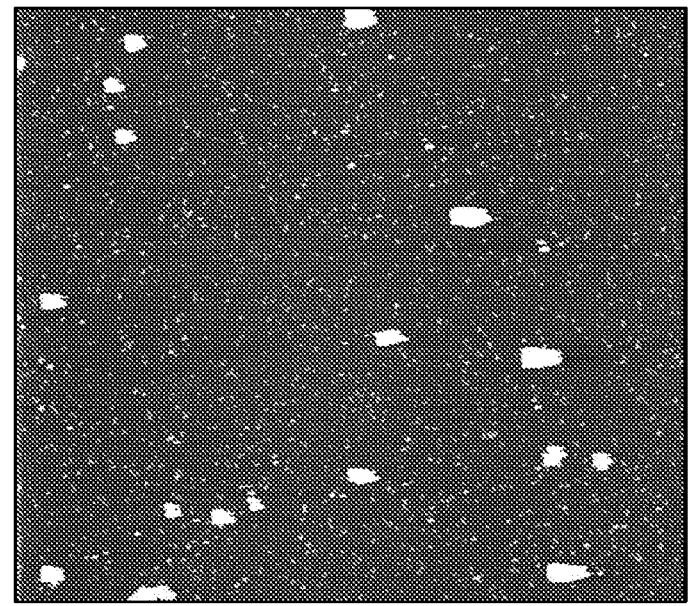

In certain situations nanobody specificity can be identified by height distribution analysis as described [37]. In this AFM based assay, the antigen is deposited on the AFM substrate and the height distribution of the sample is analyzed. The nanobody is then added to the immobilized target antigen and the height distribution reanalyzed. If the nanobody binds to the target antigen, the particle height changes, if not it remains constant. It can be determined which specific particle heights are interacting with each different nanobody using this technique as described [37]. It can also be determined the extent of nanobody binding as a function of nanobody concentration, generating a Langmuir isotherm plot from which we can calculate a KD value for the nanobody. It can also be determined using a technique termed recognition imaging [42], where the nanobody is chemically fixed to a short tether on the AFM tip. The antigen sample is added to the AFM substrate and imaged using the tethered AFM tip. The resulting scan provides the standard AFM image along with an overlay showing specific locations where the nanobody has deflected the tether because it is binding to antigen on the scanned surface. Using this technique it was possible to show that a nanobody against fibrillar Aβ binds at fixed repetitive intervals to fibrillar Aβ indicative of the helical structure of the fibrils [42]. Finally it is possible to directly image whether a phage displayed version of the nanobody binds to a given target. The nanobodies are displayed on the surface of bacteriophage for easy visualization by AFM. Using this technique the inventors showed that three different nanobodies against oligomeric Aβ recognize three distinctly different oligomeric Aβ species (see FIG. 3). All positive nanobodies were screened for selectivity towards FTD, ALS and healthy brain samples.

Identification of TDP-43 Morphology Specific Nanobodies that Distinguish Between Brain Tissue from FTD, ALS and Healthy Human Post-Mortem Cases.

Individual nanobodies were screened against normal, FTLD-TDP and sporadic ALS brain tissue specimens using ELISA, dot blot and immunohistochemistry to identify those nanobody reagents that have the most potential to distinguish between healthy and disease cases.

Western- and Dot-Blot Assays:

All assays were performed essentially as described [2, 3].

Immunohistochemistry of Brain Tissue.

Formalin-fixed paraffin-embedded brain tissue sections from well characterized normal and neurodegenerative cases are pre-treated with 0.1% triton X-100 for 30 minutes. Nanobody is then added (0.2 mg/ml) to the brain sections and incubated for 1 hour at room temperature. Primary antibodies (mouse anti-c-Myc to label nanobodies containing a c-myc tag, and neuronal markers such as anti-Synaptophysin (Santa Cruz) 1/500 dilution in BSA 3%) are then applied and incubated for 1 hour at room temperature. The brain sections are washed 3 times with PBS and incubated with 1/1000 dilution of secondary antibody in BSA 3% (goat anti-mouse IgG Alexa Fluor 488 and goat anti-rabbit Alexa Fluor 594, Invitrogen) for 45 min at room temperature. Images are taken with a confocal microscope at 60× magnification.

Example 2

Potential Morphology Specific Reagents to TDP-43 that could Distinguish Between Amyotrophic Lateral Sclerosis and Frontotemporal Dementia In order to isolate therapeutic agents against brain-derived TDP-43 (found in FTD and ALS patients), a combination of phage display technology and AFM was used. A mixture of Tomlinson I and J and Sheets phage libraries were used for the initial screening ($10^{12}$ pfu/mL). A series of negative panning steps were executed to eliminate phage particles that were reactive with bovine serum albumin (BSA), α-synuclein (α-syn), healthy tissue and TDP-43 isolated from healthy patients. 20 µm and 5 µm AFM images were taken before and after the panning process. (FIGS. 4A-4D)

Twelve rounds of negative panning against 1 mg/mL of Bovine Serum Albumin (BSA) were carried out using immunotubes. Once BSA specific binders was excluded, eight rounds of negative panning were performed against 500 µg/mL and 100 µg/mL of α-syn in immunotubes. Subsequently, binders to healthy tissue were removed using 50 µg/mL and 10 µg/mL of homogenized healthy human brain tissue samples. Lastly, eight rounds of negative panning were carried out against 5 μg/mL of TDP-43 immunoprecipitated from healthy human brain tissue.

After the negative panning steps, simultaneously, but separately, two rounds of positive panning were completed with 10 μg/mL of TDP-43 isolated from the brains of ALS patients and two rounds using FTD isolated TDP-43. The unbound phage after the second round of panning against ALS TDP-43 was collected and used for positive panning against FTD TDP-43 and vice versa. This allowed for the isolation of FTD and ALS TDP-43 specific clones.

Example 3

Characterization of ALS Clones

Figure 5A:
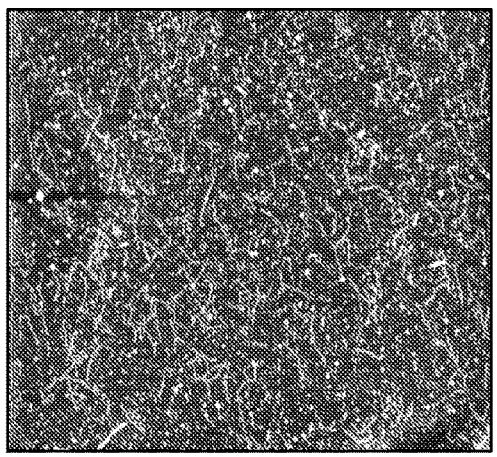
FIGS. 5A-5C. Characterization of ALS Clones.
Figure 5A:
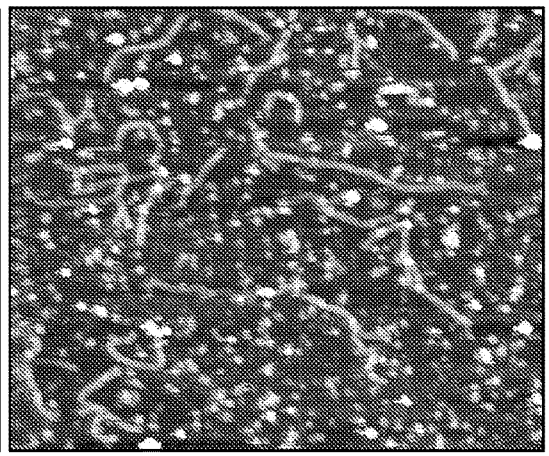
Figure 5A:
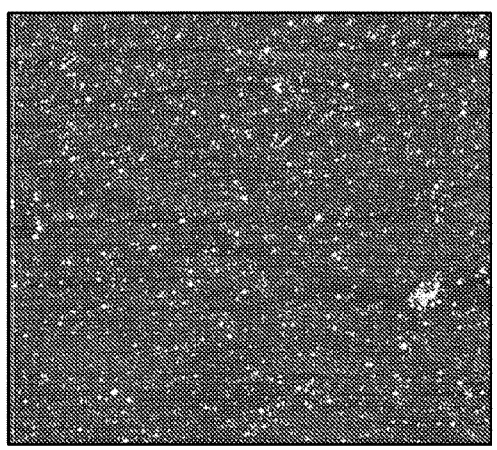
Figure 5A:
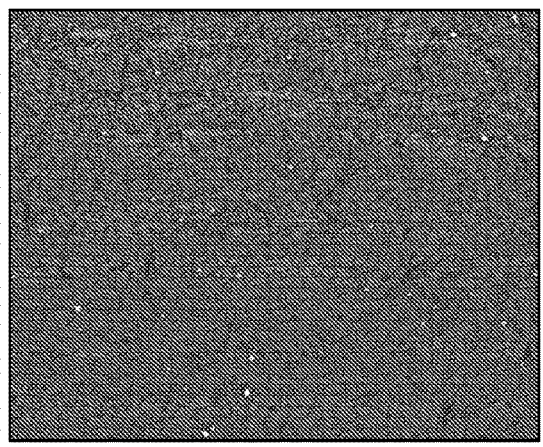
Figure 5A:
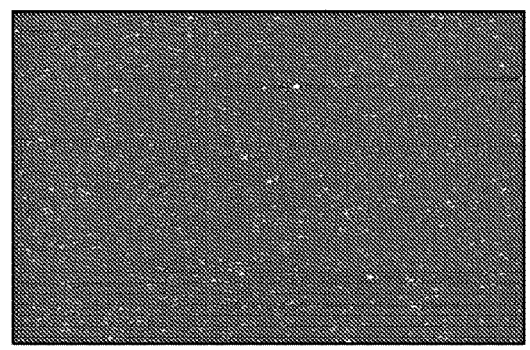
Figure 5B:
Figure 5B:
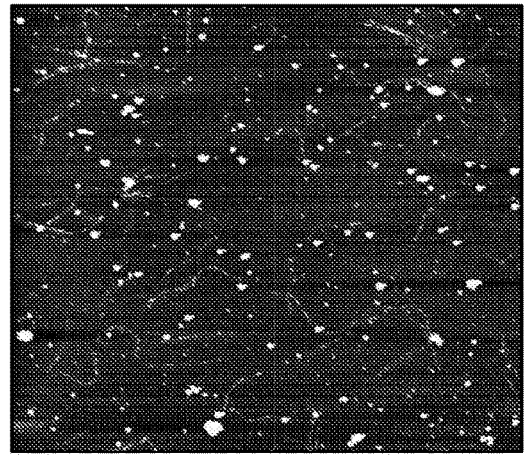
Figure 5B:
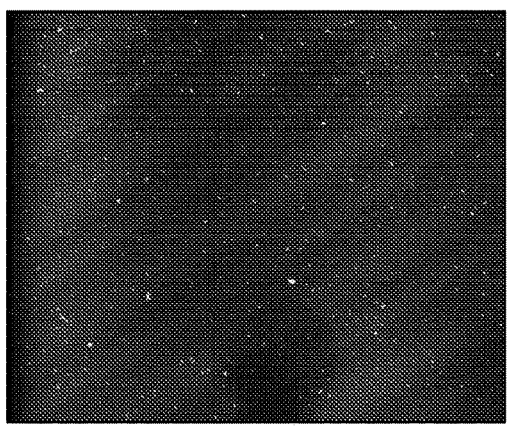
Figure 5B:
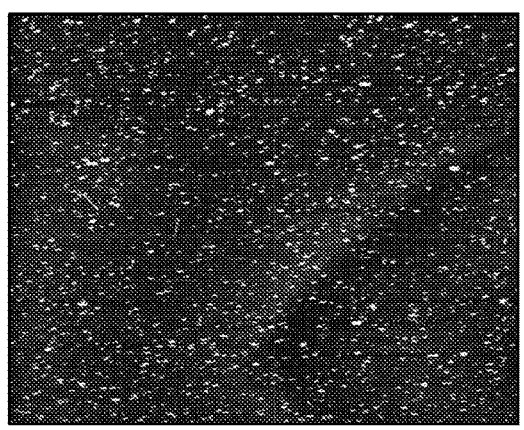
Figure 5B:
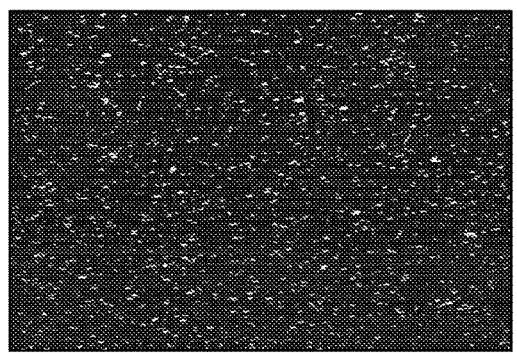
Figure 5C:
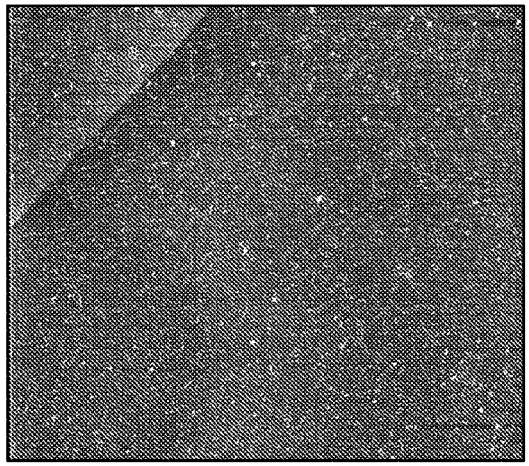
Figure 5C:
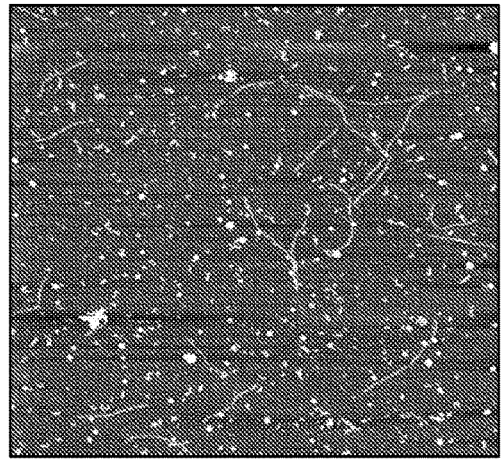
Figure 5C:
Figure 5C:
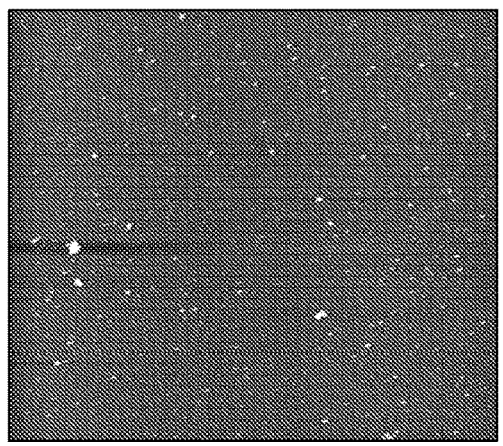
Figure 5C:
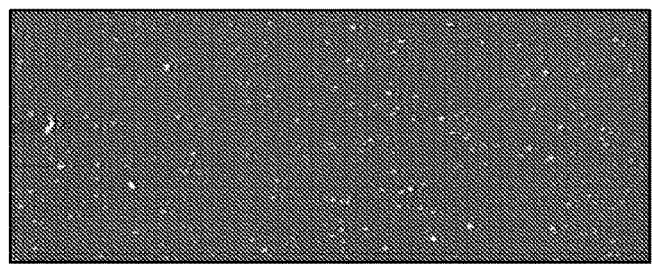

Forty-five clones that may react specifically to the TDP-43 protein immunoprecipitated from the brains of ALS patients were isolated using the AFM biopanning process. DNA sequencing results reduced the number of potential clones to 40. In the initial characterization, the TDP-43 protein immunoprecipitated from ALS, FTD and healthy individuals, as well as healthy brain tissue homogenate were immobilized on mica. These targets were then incubated with phage particles produced using each individual clone and imaged using AFM. The AFM generated images further suggested which clones may be ALS specific. Some of the potential clones from the screening process are presented in FIGS. 5A-5C. Significant phage reactivity to TDP-43 from ALS patients is expected while little to no binding should be detected with the TDP-43 from FTD and healthy individuals and the healthy brain tissue homogenate. Both 5 μm and 20 μm images are illustrated in some cases to clearly exhibit phage binding. Further characterization of the clones using techniques such as ELISA, Western blotting, etc., is necessary to verify ALS TDP-43 reactive clones.

Exemplary DNA Sequences of ALS TDP-43 reactive clones are provided below:

Sequence 1 (Clone 1B):
(SEQ ID NO: 1)
5'-CCATGGCCGAGGTGCAGCTGTTGGAGTCTGGGGGAGGCTTGGTAC

AGCCTGGGGGGTCCCCGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCAACTATTTCTGCTTCTGGTACTTATACAAATTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAAACTTCTTCTTATTTTGACTACTGGGGCCAGG

GAACCCTGGTCACCGTCTCGAGCGGTGGAGGCGGTTCAGGCGGAGGTG

GCAGCGGCGGTGGCGGGTCGACGGACATCCAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATGCTGCATCCAATTTGCAAAGTG

GGGTCCCATCAAGGTTCAGTGGCAGTGGATCTGGGACAGATTTCACTC

TCACCATCAGCAGTCTGCAACCTGAAGATTTTGCAACTTACTACTGTC

AACAGGATAATTATGCTCCTTATACGTTCGGCCAAGGGACCAAGGTGG

AAATCAAACGGGCGGCCGC-3'

Sequence 2 (Clone 3B):
(SEQ ID NO: 2)
5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCAACTATTCGCCATGCTGGTCAGTCGACGGACATCC

AGATGACCCAGTCTCCATCCTCCCTGTCTGCATCTGTAGGAGACAGAG

TCACCATCACTTGCCGGGCAAGTCAGAGCATTAGCAGCTATTTAAATT

GGTATCAGCAGAAACCAGGGAAAGCCCCTAAGCTCCTGATCTATATGG

CATCCCGTTTGCAAAGTGGGGTCCCATCAAGGTTCAGTGGCAGTGGAT

CTGGGACAGATTTCACTCTCACCATCAGCAGTCTGCAACCTGAAGATT

TTGCAACTTACTACTGTCAACAGCAGCGTACGAAGCCTCCTACGTTCG

GCCAAGGGACCAAGGTGGAAATCAAACGGGCGGCCGC-3'

Sequence 3 (Clone 3H):
(SEQ ID NO: 3)
5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCAACTATTGCTTCTGCTGGTACTGATACAGCTTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAAGATACTACTGCTTTTGACTACTGGGGCCAGG

GAACCCTGGTCACCGTCTCGAGCGGTGGAGGCGGTTCAGGCGGAGGTG

GCAGCGGCGGTGGCGGGTCGACGGACATCAAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATGATGCATCCACTTTGCAAAGTG

GGGTCCCATCAAGGTTCAGTGGCAGTGGATCTGGGACAGATTTCACTC

TCACCATCAGCAGTCTGCAACCTGAAGATTTTGCAACTTACTACTGTC

AACAGTCTACTTATGCTCCTGCTACGTTCGGCCAAGGGACCAAGGTGG

AAATCAAACGGGCGGCCGC-3'

Sequence 4 (Clone 4F):
(SEQ ID NO: 4)
5'-CCATGGCCGAGGTGTTTGACTACTGGGGCCAGGGAACCCTGGTCA

CCGTCTCGAGCGGTGGAGGCGGTTCAGGCGGAGGTGGCAGCGGCGGTG

GCGGGTCGACGGACATCCAGATGACCCAGTCTCCATCCTCCCTGTCTG

CATCTGTAGGAGACAGAGTCACCATCACTTGCCGGGCAAGTCAGAGCA

TTAGCAGCTATTTAAATTGGTATCAGCAGAAACCAGGGAAAGCCCCTA

AGCTCCTGATCTATTCTGCATCCAATTTGCAAAGTGGGGTCCCATCAA

GGTTCAGTGGCAGTGGATCTGGGACAGATTTCACTCTCACCATCAGCA

GTCTGCAACCTGAAGATTTTGCAACTTACTACTGTCAACAGAGTTATT

CTAGTCCTTCTACGTTCGGCCAAGGGACCAAGGTGGAAATCAAACGGG

CGGCCGC-3'

-continued

Sequence 5 (Clone 5E):
(SEQ ID NO: 5)
5'-CCATGGCCGAGGTGCAGCTGTTGGAGTCTGGGGGAGGCTTGGTAC

AGCCTGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCATCTATTAATAATGCTGGTATGATACAAATTACGC

AGACTCCGTGAAGGGCAGGTTCACCATCTCCAGAGACAATTCCAAGAA

CACGCTGTATCTGCAAATGAACAGCCTGAGAGCCGAGGACACGGCCGT

ATATTACTGTGCGAAAAATAATGCTTATTTTGACTACTGGGGCCAGGG

AACCCTGGTCACCGTCTCGAGCGGTGGAGGCGGTTCAGGCGGAGGTGG

CAGCGGCGGTGGCGGGTCGACGGACATCCAGATGACCCAGTCTCCATC

CTCCCTGTCTGCATCTGTAGGAGACAGAGTCACCATCACTTGCCGGGC

AAGTCAGAGCATTAGCAGCTATTTAAATTGGTATCAGCAGAAACCAGG

GAAAGCCCCTAAGCTCCTGATCTATGGTGCATCCAGTTTGCAAAGTGG

GGTCCCATCAAGGTTCAGTGGCAGTGGATCTGGGACAGATTTCACTCT

CACCATCAGCAGTCTGCAACCTGAAGATTTTGCAACTTACTACTGTCA

ACAGTATGATTCTGCTCCTGGTACGTTCGGCCAAGGGACCAAGGTGGA

AATCAAACGGGCGGCCGC-3'

Sequence 6 (Clone 8D):
(SEQ ID NO: 6)
5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCAACTATTAATAATAGTGGTACTTCTACAAATTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAAAGTACTAATTATTTTGACTACTGGGGCCAGG

GAACCCTGGTCACCGTCTCGAGCGGTGGAGGCGGTTCAGGCGGAGGTG

GCAGCGGCGGTGGCGGGTCGACGGACATCCAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATGCTGCATCCAGTTTGCAAAGTG

GGGTCCCATCAAGGTTCAGTGGCAGTGGATCTGGGACAGATTTCACTC

TCACCATCAGCAGTCTGCAACCTGAAGATTTTGCAACTTACTACTGTC

AACAGAATGCTGCTGATCCTACTACGTTCGGCCAAGGGACCAAGGTGG

AAATCAAACGGGCGGCCGC-3'

Example 4

Characterization of Potential FTD Clones

Figure 6:
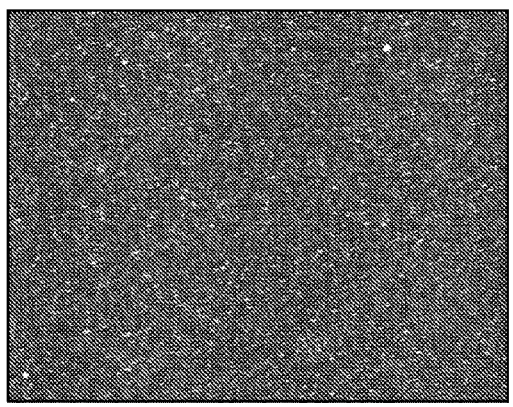
FIG. 6. Characterization of FTD Clones.
Figure 6:
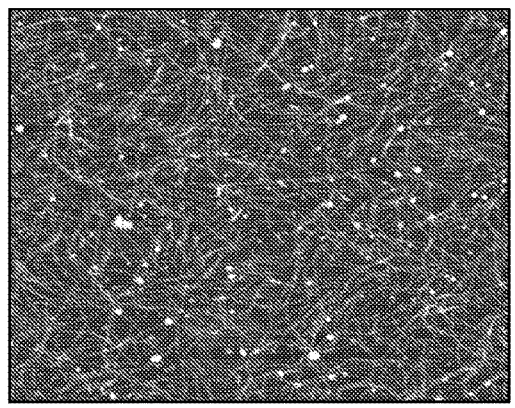
Figure 6:
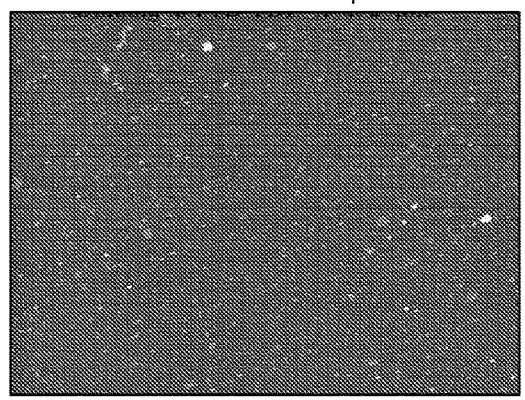
Figure 6:
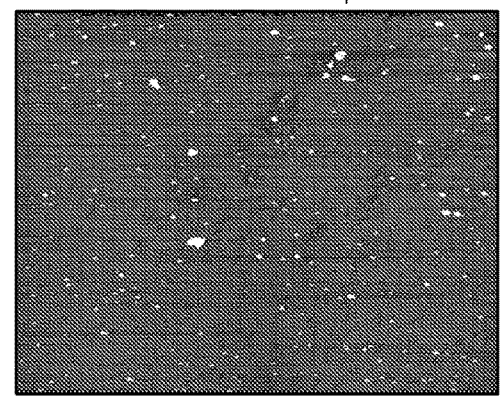

About 100 clones were obtained after the three rounds of panning using the FTD TDP-43. Sequence verified clones were further screened using AFM against 5 µg/mL each of FTD TDP-43, ALS TDP-43 and healthy tissue. We expect to see little to no binding of these clones to the healthy tissue, healthy protein and ALS TDP-43 against which negative panning was performed. Potential clones are also expected to show a great deal of binding to the FTD TDP-43 target. AFM images of a representative clone are provided in FIG. 6.

Example 5

Single Chain Variable Fragments Isolated Utilizing ALS TDP-43

Single chain variable fragments (scFvs) against ALS immunoprecipitated (IP) TDP-43 were previously isolated using a novel AFM based biopanning technology (Example 3 above). Protein translation of the DNA sequences of the 40 ALS TDP-43 clones revealed 23 clones with no stop codons or mutations, which were then used in further studies.

1B
(SEQ ID NO: 1)
5'-CCATGGCCGAGGTGCAGCTGTTGGAGTCTGGGGGAGGCTTGGTAC

AGCCTGGGGGGTCCCCGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCAACTATTTCTGCTTCTGGTACTTATACAAATTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAAACTTCTTCTTATTTTGACTACTGGGGCCAGG

GAACCCTGGTCACCGTCTCGAGCGGTGGAGGCGGTTCAGGCGGAGGTG

GCAGCGGCGGTGGCGGGTCGACGGACATCCAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATGCTGCATCCAATTTGCAAAGTG

GGGTCCCATCAAGGTTCAGTGGCAGTGGATCTGGGACAGATTTCACTC

TCACCATCAGCAGTCTGCAACCTGAAGATTTTGCAACTTACTACTGTC

AACAGGATAATTATGCTCCTTATACGTTCGGCCAAGGGACCAAGGTGG

AAATCAAACGGGCGGCCGC-3'

1D
(SEQ ID NO: 7)
5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCAGGTATTTCTAGTTCTGGTAATACTACAACTTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAAGATGGTGCTACTTTTGACTACTGGGGCCAGG

GAACCCTGGTCACCGTCTCGAGCGGTGGAGGCGGTTCAGGCGGAGGTG

GCAGCGGCGGTGGCGGGTCGACGGACATCCAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATTCTGCATCCTCTTTGCAAAGTG

GGGTCCCATCAAGGTTCAGTGGCAGTGGATCTGGGACAGATTTCACTC

TCACCATCAGCAGTCTGCAACCTGAAGATTTTGCAACTTACTACTGTC

AACAGTATGATGGTTCTCCTGATACGTTCGGCCAAGGGACCAAGGTGG

AAATCAAACGGGCGGCCGC-3'

1E (SEQ ID NO: 8)
5'-CCATGGCCGAGGTGTTTGACTACTGGGGCCAGGGAACCCTGGTCA

CCGTCTCGAGCGGTGGAGGCGGTTCAGGCGGAGGTGGCAGCGGCGGTG

GCGGGTCGACGGACATCCAGATGACCCAGTCTCCATCCTCCCTGTCTG

CATCTGTAGGAGACAGAGTCACCATCACTTGCCGGGCAAGTCAGAGCA

TTAGCAGCTATTTAAATTGGTATCAGCAGAAACCAGGGAAAGCCCCTA

AGCTCCTGATCTATTCTGCATCCACTTTGCAAAGTGGGGTCCCATCAA

GGTTCAGTGGCAGTGGATCTGGGACAGATTTCACTCTCACCATCAGCA

GTCTGCAACCTGAAGATTTTGCAACTTACTACTGTCAACAGGGTGATA

CTAATCCTAGTACGTTCGGCCAAGGGACCAAGGTGGAAATCAAACGGG

CGGCCGC-3'

1F (SEQ ID NO: 9)
5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTTCGCCAGGCTCCAGGGAAGGGGC

TGGAGTGGGTCTCAAGTATTGCTAGTTCTGGTGATGATACAAATTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAAACTGCTAGTAGTTTTGACTACTGGGGCCAGG

GAACCCTGGTCACCGTCTCGAGCGGTGGAGGCGGTTCAGGCGGAGGTG

GCAGCGGCGGTGGCGGGTCGACGGACATCCAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATTCTGCATCCTCTTTGCAAAGTG

GGGTCCCATCAAGGTTCAGTGGCAGTGGATCTGGGACAGATTTCACTC

TCACCATCAGCAGTCTGCAACCTGAAGATTTTGCAACTTACTACTGTC

AACAGACTAATGGTAATCCTAATACGTTCGGCCAAGGGACCAAGGTGG

AAATCAAACGGGCGGCCGC-3'

1G (SEQ ID NO: 10)
5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCAGCTATTTCTAATGATGGTAATAATACAGATTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAAACTGATTCTACTTTTGACTACTGGGGCCAGG

GAACCCTGGTCACCGTCTCGAGCGGTGGAGGCGGTTCAGGCGGAGGTG

GCAGCGGCGGTGGCGGGTCGACGGACATCCAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATTCTGCATCCAATTTGCAAAGTG

GGGTCCCATCAAGGTTCAGTGGCAGTGGATCTGGGACAGATTTCACTC

TCACCATCAGCAGTCTGCAACCTGAAGATTTTGCAACTTACTACTGTC

AACAGAGTGCTGATAGTCCTACTACGTTTGGCCAAGGGACCAAGGTGG

AAATCAAACGGGCGGCCGC-3'

2A (SEQ ID NO: 11)
5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCAGATATTGGTGGTGATGGTTATAATACATCTTACG

CAGACTCCGTGAAGGGCCGGTTCACCATCTCCAGAGACAACTCCAAGA

ACACGCTGTATCTGCAAATGAACAGCCTGAGAGCCGAGGACACGGCCG

TATATTACTGTGCGAAAAGTTATACTGCTTTTGACTACTGGGGCCAGG

GAACCCTGGTCACCGTCTCGAGCGGTGGAGGCGGTTCAGGCGGAGGTG

GCAGCGGCGGTGGCGGGTCGACGGACATCCAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATTCTGCATCCGGTTTGCAAAGTG

GGGTCCCATCAAGGTTCAGTGGCAGTGGATCTGGGACAGATTTCACTC

TCACCATCAGCAGTCTGCAACCTGAAGATTTTGCAACTTACTACTGTC

AACAGGATACTAATGGTCCTTCTACGTTCGGCCAAGGGACCAAGGTGG

AAATCAAACGGGCGGCCGC-3'

2C (SEQ ID NO: 12)
5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCAAGTATTTATTCTGATGGTGGTGCTACATCTTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAAGCTACTGCTACTTTTGACTACTGGGGCCAGG

GAACCCTGGTCACCGTCTCGAGCGGTGGAGGCGGTTCAGGCGGAGGTG

GCAGCGGCGGTGGCGGGTCGACGGACATCCAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATTCTGCATCCGTTTGCAAAGTG

GGGTCCCATCAAGGTTCAGTGGCAGTGGATCTGGGACAGATTTCACTC

TCACCATCAGCAGTCTGCAACCTGAAGATTTTGCAACTTACTACTGTC

AACAGTCTTCTACTAGTCCTAGTACGTTCGGCCAAGGGACCAAGGTGG

AAATCAAACGGGCGGCCGC-3'

2D (SEQ ID NO: 13)
5'-CCATGGCCGAGGTGTTTGACTACTGGGGCCAGGGAACCCTGGTCA

CCGTCTCGAGCGGTGGAGGCGGTTCAGGCGGAGGTGGCAGCGGCGGTG

GCGGGTCGACGGACATCCAGATGACCCAGTCTCCATCCTCCCTGTCTG

CATCTGTAGGAGACAGAGTCACCATCACTTGCCGGGCAAGTCAGAGCA

TTAGCAGCTATTTAAATTGGTATCAGCAGAAACCAGGGAAAGCCCCTA

AGCTCCTGATCTATACTGCATCCTCTTTGCAAAGTGGGGTCCCATCAA

GGTTCAGTGGCAGTGGATCTGGGACAGATTTCACTCTCACCATCAGCA

GTCTGCAACCTGAAGATTTTGCAACTTACTACTGTCAACAGAGTGCTA

ATGCTCCTAATACGTTCGGCCAAGGGACCAAGGTGGAAATCAAACGGG

CGGCCGC-3'

2F (SEQ ID NO: 14)
5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCAAATATTGCTGGTAATGGTTCTTATACATATTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAAGATGATGCTGCTTTTGACTACTGGGGCCAGG

GAACCCTGGTCACCGTCTCGAGCGGTGGAGGCGGTTCAGGCGGAGGTG

GCAGCGGCGGTGGCGGGTCGACGGACATCCAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATTCTGCATCCTATTTGCAAAGTG

GGGTCCCATCAAGGTTCAGTGGCAGTGGATCTGGGACAGATTTCACTC

TCACCATCAGCAGTCTGCAACCTGAAGATTTTGCAACTTACTACTGTC

AACAGAGTGCTACTACTCCTAATACGTTCGGCCAAGGGACCAAGGTGG

AAATCAAACGGGCGGCCGC-3'

3A (SEQ ID NO: 15)
5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TAGAGTGGGTCTCAACTATTAATACTGCTGGTAATGGTACAAATTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAAGGTACTGCTGCTTTTGACTACTGGGGCCAGG

GAACCCTGGTCACCGTCTCGAGCGGTGGAGGCGGTTCAGGCGGAGGTG

GCAGCGGCGGTGGCGGGTCGACGGACATCCAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGGTCTATTCTGCATCCGCTTTGCAAAGTG

GGGTCCCATCAAGGTTCAGTGGCAGTGGATCTGGGACAGATTTCACTC

TCACCATCAGCAGTCTGCAACCTGAAGATTTTGCAACTTACTACTGTC

AACAGGCTGGTGATAGTCCTGCTACGTTCGGCCAAGGGACCAAGGTGG

AAATCAAACGGGCGGCCGC-3'

3B (SEQ ID NO: 2)
5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCAACTATTCGCCATGCTGGTCAGTCGACGGACATCC

AGATGACCCAGTCTCCATCCTCCCTGTCTGCATCTGTAGGAGACAGAG

TCACCATCACTTGCCGGGCAAGTCAGAGCATTAGCAGCTATTTAAATT

GGTATCAGCAGAAACCAGGGAAAGCCCCTAAGCTCCTGATCTATATGG

CATCCCGTTTGCAAAGTGGGGTCCCATCAAGGTTCAGTGGCAGTGGAT

CTGGGACAGATTTCACTCTCACCATCAGCAGTCTGCAACCTGAAGATT

TTGCAACTTACTACTGTCAACAGCAGCGTACGAAGCCTCCTACGTTCG

GCCAAGGGACCAAGGTGGAAATCAAACGGGCGGCCGC-3'

3C (SEQ ID NO: 16)
5'-CCATGGCCGAGGTGTTTGACTACTGGGGCCAGGGAACCCTGGTCA

CCGTCTCGAGCGGTGGAGGCGGTTCAGGCGGAGGTGGCAGCGGCGGTG

GCGGGTCGACGGACATCCAGATGACCCAGTCTCCATCCTCCCTGTCTG

CATCTGTAGGAGACAGAGTCACCATCACTTGCCGGGCAAGTCAGAGCA

TTAGCAGCTATTTAAATTGGTATCAGCAGAAACCAGGGAAAGCCCCTA

AGCTCCTGATCTATTATGCATCCACTTTGCAAAGTGGGGTCCCATCAA

GGTTCAGTGGCAGTGGATCTGGGACAGATTTCACTCTCACCATCAGCA

GTCTGCAACCTGAAGATTTTGCAACTTACTACTGTCAACAGAATTATA

ATTCTCCTTATACGTTCGGCCAAGGGACCAAGGTGGAAATCAAACGGG

CGGCCGC-3'

3D (SEQ ID NO: 17)
5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCAGATATTGATGGTGCTGGTAGTGATACAGGTTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAATCTACTAGTACTTTTGACTACTGGGGCCAGG

GAACCCTGGTCACCGTCTCGAGCGGTGGAGGCGGTTCAGGCGGAGGTG

GCAGCGGCGGTGGCGGGTCGACGGACATCCAGATGACCCAGTCTCCAT

-continued

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATGGTGCATCCAATTTGCAAAGTG

GGGTCCCATCAAGGTTCAGTGGCAGTGGATCTGGGACAGATTTCACTC

TCACCATCAGCAGTCTGCAACCTGAAGATTTTGCAACTTACTACTGTC

AACAGTCTACTACTAATCCTGCTACGTTCGGCCAAGGGACCAAGGTGG

AAATCAAACGGGCGGCCGC-3'

3H (SEQ ID NO: 3)

5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCAACTATTGCTTCTGCTGGTACTGATACAGCTTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAAGATACTACTGCTTTTGACTACTGGGGCCAGG

GAACCCTGGTCACCGTCTCGAGCGGTGGAGGCGGTTCAGGCGGAGGTG

GCAGCGGCGGTGGCGGGTCGACGGACATCAAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATGATGCATCCACTTTGCAAAGTG

GGGTCCCATCAAGGTTCAGTGGCAGTGGATCTGGGACAGATTTCACTC

TCACCATCAGCAGTCTGCAACCTGAAGATTTTGCAACTTACTACTGTC

AACAGTCTACTTATGCTCCTGCTACGTTCGGCCAAGGGACCAAGGTGG

AAATCAAACGGGCGGCCGC-3'

4A (SEQ ID NO: 18)

5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCATATATTAATGGTGATGGTGATAGTACAACTTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAATCTAATACTGCTTTTGACTACTGGGGCCAGG

GAACCCTGGTCACCGTCTCGAGCGGTGGAGGCGGTTCAGGCGGAGGTG

GCAGCGGCGGTGGCGGGTCGACGGACATCCAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATTATGCATCCACTTTGCAAAGTG

GGGTCCCATCAAGGTTCAGTGGCAGTGGATCTGGGACAGATTTCACTC

TCACCATCAGCAGTCTGCAACCTGAAGATTTTGCAACTTACTACTGTC

AACAGTCTTCTGCTACTCCTGCTACGTTCGGCCAAGGGACCAAGGTGG

AAATCAAACGGGCGGCCGC-3'

4B (SEQ ID NO: 19)

5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCAGCTATTGGTGCTTCTGGTAATGCTACAGCTTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAATCTACTACTGATTTTGACTACTGGGGCCAGG

GAACCCTGGTCACCGTCTCGAGCGGTGGAGGCGGTTCAGGCGGAGGTG

GCAGCGGCGGTGGCGGGTCGACGGACATCCAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATAATGCATCCGGTTTGCAAAGTG

GGGTCCCATCAAGGTTCAGTGGCAGTGGATCTGGGACAGATTTCACTC

TCACCATCAGCAGTCTGCAACCTGAAGATTTTGCAACTTACTACTGTC

AACAGGCAGCTAATTATCCTACTACGTTCGGCCAAGGGACCAAGGTGG

AAATCAAACGGGCGGCCGC-3'

4F (SEQ ID NO: 4)

5'-CCATGGCCGAGGTGTTTGACTACTGGGGCCAGGGAACCCTGGTCA

CCGTCTCGAGCGGTGGAGGCGGTTCAGGCGGAGGTGGCAGCGGCGGTG

GCGGGTCGACGGACATCCAGATGACCCAGTCTCCATCCTCCCTGTCTG

CATCTGTAGGAGACAGAGTCACCATCACTTGCCGGGCAAGTCAGAGCA

TTAGCAGCTATTTAAATTGGTATCAGCAGAAACCAGGGAAAGCCCCTA

AGCTCCTGATCTATTCTGCATCCAATTTGCAAAGTGGGGTCCCATCAA

GGTTCAGTGGCAGTGGATCTGGGACAGATTTCACTCTCACCATCAGCA

GTCTGCAACCTGAAGATTTTGCAACTTACTACTGTCAACAGAGTTATT

CTAGTCCTTCTACGTTCGGCCAAGGGACCAAGGTGGAAATCAAACGGG

CGGCCGC-3'

4G (SEQ ID NO: 20)

5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCAGCTATTGCTTCTGATGGTACTAATACATCTTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAAACTGATGGTGATTTTGACTATTGGGGCCAGG

GAACCCTGGTCACCGTCTCGAGCGGTGGAGGCGGTTCAGGCGGAGGTG

GCAGCGGCGGTGGCGGGTCGACGGCCATCCAGATGACCCAGTCTCCAT

```
CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATACTGCATCCTATTTGCAAAGTG

GGGTCCCATCAAGGTTCAGTGGCAGTGGATCTGGGACAGATTTCACTC

TCACCATCAGCAGTCTGCAACCTGAAGATTTTGCAACTTACTACTGTC

AACAGACTGCTGCTAGTCCTAATACGTTCGGCCAAGGGACCAAGGTGG

AAATCAAACGGGCGGCCGC-3'

5C
                                          (SEQ ID NO: 21)
5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCAACTATTGCTGCTGGTGGTGATAATACAACTTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAAGATTCTTATACTTTTGACTACTGGGGCCAGG

GAACCCTGGTCACCGTCTCGAGCGGTGGAGGCGGTTCAGGCGGAGGTG

GCAGCGGCGGTGGCGGGTCGACGGACATCCAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCACCTAAGCTCCTGATCTATTCTGCATCCACTTTGCAAAGTG

GGGTCCCATCAAGGTTCAGTGGCAGTGGATCTGGGACAGATTTCACTC

TCACCATCAGCAGTCTGCAACCTGAAGATTTTGCAACTTACTACTGTC

AACAGAGTACTACTACTCCTGCTACGTTCGGCCAAGGGACCAAGGTGG

AAATCAAACGGGCGGCCGC-3'

5E
                                          (SEQ ID NO: 5)
5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCATCTATTAATAATGCTGGTATGATACAAATTACGC

AGACTCCGTGAAGGGCAGGTTCACCATCTCCAGAGACAATTCCAAGAA

CACGCTGTATCTGCAAATGAACAGCCTGAGAGCCGAGGACACGGCCGT

ATATTACTGTGCGAAAAATAATGCTTATTTTGACTACTGGGGCCAGGG

AACCCTGGTCACCGTCTCGAGCGGTGGAGGCGGTTCAGGCGGAGGTGG

CAGCGGCGGTGGCGGGTCGACGGACATCCAGATGACCCAGTCTCCATC

CTCCCTGTCTGCATCTGTAGGAGACAGAGTCACCATCACTTGCCGGGC

AAGTCAGAGCATTAGCAGCTATTTAAATTGGTATCAGCAGAAACCAGG

GAAAGCCCCTAAGCTCCTGATCTATGTGCATCCAGTTTGCAAAGTGG

GGTCCCATCAAGGTTCAGTGGCAGTGGATCTGGGACAGATTTCACTCT

CACCATCAGCAGTCTGCAACCTGAAGATTTTGCAACTTACTACTGTCA

ACAGTATGATTCTGCTCCTGGTACGTTCGGCCAAGGGACCAAGGTGGA

AATCAAACGGGCGGCCGC-3'

5H
                                          (SEQ ID NO: 22)
5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGAC

TGGAGTGGGTCTCATCTATTTCTTCTACTGGTTCTGATACAACTTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAAGCTGGTTCTTCTTTTGACTACTGGGGCCAGG

GAACCCTGGTCACCGTCTCGAGCGGTGGAGGCGGTTCAGGCGGAGGTG

GCAGCGGCGGTGGCGGGTCGACGGACATCCAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATGCTGCATCCAATTTGCAAAGTG

GGGTCCCATCAAGGTTCAGTGGCAGTGGATCTGGGACAGATTTCACTC

TCACCATCAGCAGTCTGCAACCTGAAGATTTTGCAACTTACTACTGTC

AACAGAGTTCTTATTCTCCTTCTACGTTCGGCCAAGGGACCAAGGTGG

AAATCAAACGGGCGGCCGC-3'

8D
                                          (SEQ ID NO: 6)
5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCAACTATTAATAATAGTGGTACTTCTACAAATTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAAAGTACTAATTATTTTGACTACTGGGGCCAGG

GAACCCTGGTCACCGTCTCGAGCGGTGGAGGCGGTTCAGGCGGAGGTG

GCAGCGGCGGTGGCGGGTCGACGGACATCCAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATGCTGCATCCAGTTTGCAAAGTG

GGGTCCCATCAAGGTTCAGTGGCAGTGGATCTGGGACAGATTTCACTC

TCACCATCAGCAGTCTGCAACCTGAAGATTTTGCAACTTACTACTGTC

AACAGAATGCTGCTGATCCTACTACGTTCGGCCAAGGGACCAAGGTGG

AAATCAAACGGGCGGCCGC-3'

8E
                                          (SEQ ID NO: 23)
5'-CCATGGCCGAGGTGCAGCTGTTGGAGTCTGGGGGAGGCTTGGTAC

AGCCTGGGGGGNCCCTGAGACTCTCCTGTGCAGCCTCTGGATTCACCT

TTAGCAGCTATGCCATGAGCTGGGTCCGCCAGGCTCCAGGGAAGGGGC
```

-continued

```
TGGAGTGGGTCTCAAGTATTGCTAGTTCTGGTACTAGTACATCTTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAAGCTACTAATTCTTTTGACTATTGGGGCCAGG

GAACCCTGGTCACCGTCTCGAGCGGTGGAGGCGGTTCAGGCGGAGGTG

GCAGCGGCGGTGGCGGGTCGACGGACATCCAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATAATGCATCCACTTTGCAAAGTG

GGGTCCCATCAAGGTTCAGTGGCAGTGGATCTGGGACAGATTTCACTC

TCACCATCAGCAGTCTGCANCNNNAAGATTTTGCAACTTACTACTGTC

AACAGACTGATGCTTCTCCTTGTACGTTCGGCCAAGGGANCAAGGTGG

AAATCAAACGGGCGGCCGC-3'
```

Figure 7:
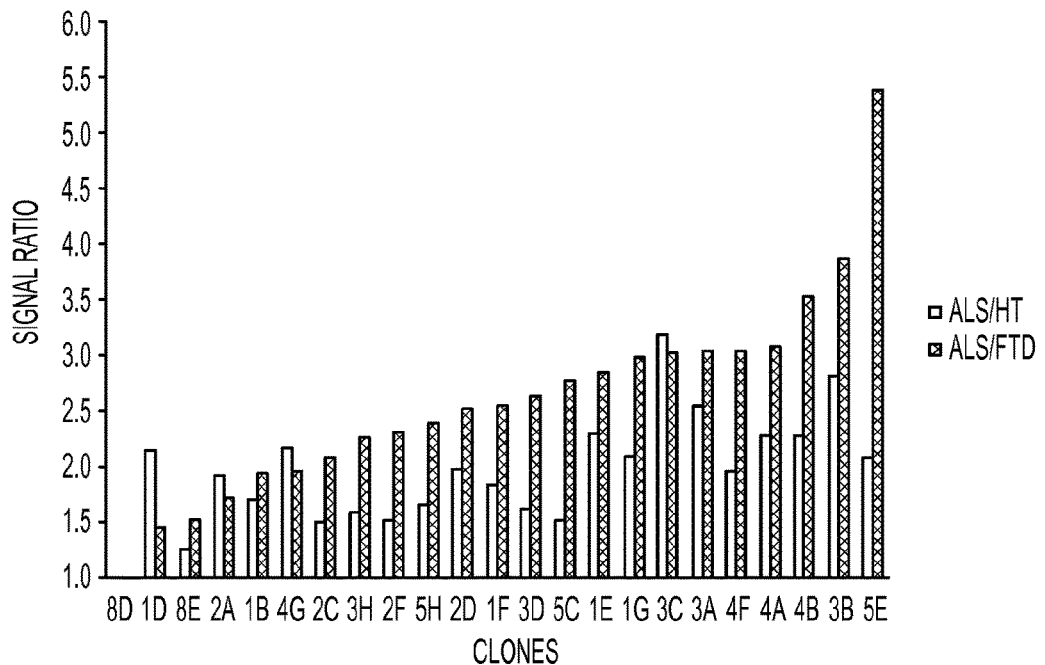
FIG. 7. Indirect phage ELISAs using ALS TDP-43 clones and human brain tissue homogenates.

In the present characterization process, phage particles and scFvs were produced from each clone and tested in indirect ELISAs for specificity to ALS. Brain tissue from ALS, FTD and healthy human patients were immobilized on high binding ELISA plates and probed with either the phage particle or scFv. Results indicated that 18 of 23 clones displayed a preference for ALS versus FTD or healthy tissue utilizing the phage particles (FIG. 7), and four of 23 clones displayed a preference for FTD versus ALS. The data is presented as a ratio of ALS to healthy tissue and ALS to FTD. The following clones displayed a preference for ALS: 8E, 1B, 2C, 3H, 2F, 5H, 2D, 1F, 3D, 5C, 1E, 1G, 3A, 4F, 4A, 4B, 3B, and 5E.

Figure 8:
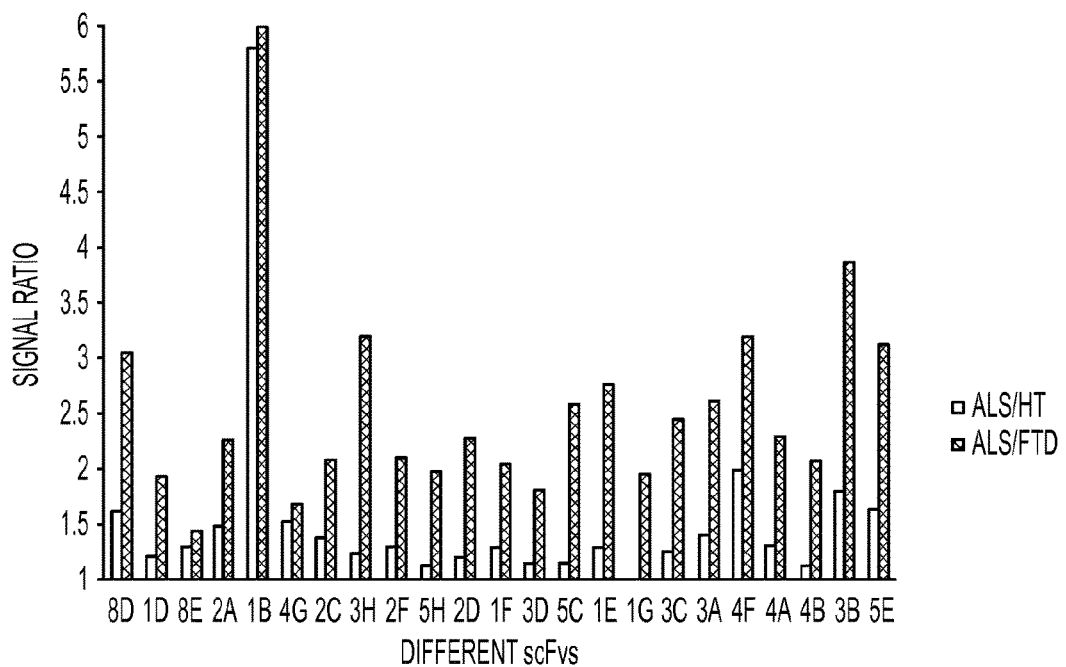
FIG. 8. Indirect scFv ELISAs using ALS TDP-43 clones and human brain tissue homogenates.
Figure 9:
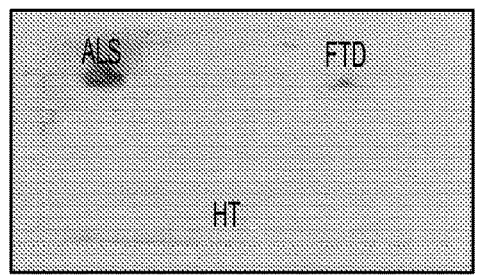
FIG. 9. Dot blot analysis of human brain tissue homogenates using ALS TDP-43 clone 2A.

FIG. 8 provides the results observed with scFvs. Application of another immunological assay, dot blots, additionally supported a preference for ALS samples as demonstrated using clone 2A (FIG. 9). Both the ELISA and dot blot results indicated the preference of clones for ALS human brain tissue.

Figure 10:
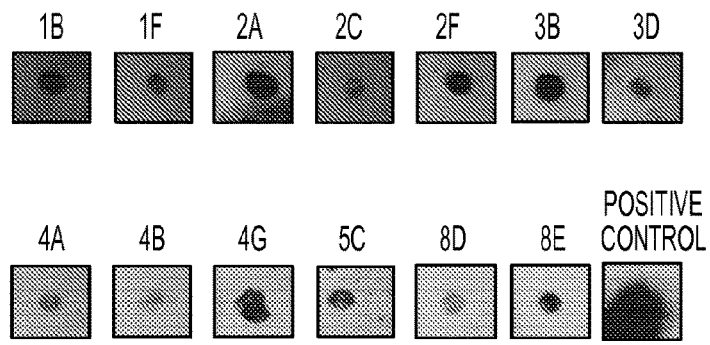
FIG. 10. Dot blot analysis of ALS TDP-43 scFv production.
Figure 11:
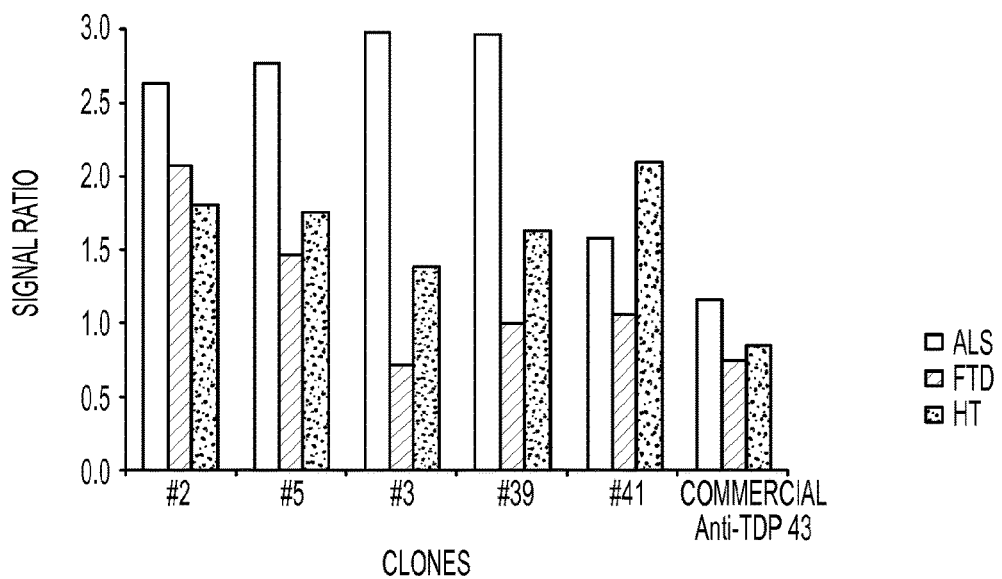
FIG. 11. Potential TDP-43 monomeric phages.

Production of phage particles for the different clones was visualized using AFM. To demonstrate scFv production, dot blot analysis was conducted of the un-concentrated supernatant. Some of the dot blots revealing scFv secretion into the supernatant are exhibited in FIG. 10. This is important since the basis of the phage capture ELISA system is the immobilization of these scFvs on the well to capture the targets of interest. The bound targets were then visualized using a monomer scFv (binds all forms of the target) attached to a phage particle. In an additional series of biopanning experiments, multiple potential monomer phages were isolated. The phage library that was negatively panned against bovine serum albumin and aggregated alpha-synuclein was positively panned against healthy IP TDP-43, ALS IP TDP-43 and FTD IP TDP-43 proteins. After each positive panning step, the bound phages were glycine-eluted and utilized in the next round of positive panning. This ensured that the remaining phages after all the positive panning steps were reactive with multiple forms of TDP-43. ELISA analysis demonstrating reactivity of these monomer phages (clones #2, #5, #3, #39 and #41) with all forms of TDP, i.e., TDP from ALS, FTD and healthy human brain tissue (FIG. 11). The following are the DNA sequences of the TDP-43 monomer clones:

```
#2
                                      (SEQ ID NO: 24)
5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCAAATATTTATAATGATGGTACTAGTACAGATTACG

CAGACTCCGTGAAGGGCAGGTTCACCATCTCCAGAGACAATTCCAAGA

ACACGCTGTATCTGCAAATGAACAGCCTGAGAGCCGAGGACACGGCCG

TATATTACTGTGCGAAATCTTCTAGTGCTTTTGACTACTGGGGCCAGG

GAACCCTGGTCACCGTCTCGAGCGGTGGAGGCGGTTCAGGCGGAGGTG

GCANCGGCGGNGGCGGGTCGACGGACATCCAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATACTGCATCCTCTTTGCAAAGTG

GGGTCCCATCAAGGTTCAGTGGCAGTGGATCTGGGACAGATTTCACTC

TCACCATCAGCAGTCTGCAACCTGAAGATTTTGCAACTTACTACTGTC

AACAGTATGATAGTACTCCTACTACGTTCGGCCAAGGGACCAAGGTGG

AAATCAAACGGGCGGCCGC-3'

#5
                                      (SEQ ID NO: 25)
5'-CCATGGCCGAGGTGCAGCTGTTGGAGTCTGGGGGAGGCTTGGTAC

GGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCAGATATTGCTAATACTGGTGATGCTACAGGTTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAAACTGGTGCTGCTTTTGACTACTGGGGCCAGG

GAACCCTGGTCACCGTCTCGAGCGGTGGAGGCGGTTCAGGCGGAGGTG

GCAGCGGCGGTGGCGGGTCGACGGACATCCAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATGCTGCATCCACTTTGCAAAGTG

GGGTCCCGTCAAGGTTCAGTGGCAGTGGATCTGGGACAGATTTCACTC

TCACCATCAGCAGTCTGCAACCTGAAGATTTTGCAACTTACTACTGTC

AACAGAGTTCTAGTGATCCTGCTACGTTCGGCCAAGGGACCAAGGTGG

AAATCAAACGGGCGGCCGC-3'

#3
                                      (SEQ ID NO: 26)
5'-CCATGGCCCAGGTGTAGCTGGTGCAGTCTGGGGGAGGCTCGGTCC

AGCCGGGGGGGTCCCTGAGACTCTCCTGTGTAGACTCTGGATTCACCT

TCAATAGCTCTGGCATGCACTGGGTCCGCCAGGCTCCAGGCAAGGGGC

TGGAGTGGGTGGCGTTTATACGCCATGATGGAAGTAAGAAATACTATG

CAGACTCCGTGAAGGGCCGATTCACCATCTCCAGAGACAGTGCCAAGA

ACACTCTGTATCTGCAAATGGACAGCCTGAGAGCCGAGGACACGGCCG
```

TATATTACTGTGCGAAAGACATGGGAGCGACTGACTACTGGGGCCAGG

GAACCCTGGTCACCGTCTCCTCAGGTGGAGGCGGTTCAGGCGGAGGTG

GCTCTGGCGGTGGCGGATCGTCTGAGCTGACTCAGGACCCTGCTGTGT

CTGTGGCCTTGGGACAGACAGTCAGAATCACATGCCAAGGAGACAGCC

TCAAAAGCTACTATGCAAGTTGGTACCAGCAGAAGCCAGGACAGGCCC

CTGCACTTGTCATCTATGGTAAAAACAACCGGCCCTCAGGGATCCCAG

ACCGATTCTCTGGCTCCAGCTCAGGAAACACAGCTTCCTTGACCATCA

CTGGGACTCTGGCGGAAGATGAGGCTGACTATTACTGTAACTCCCGGG

ACAGCAGTGGTAACCGTGTGCTATTCGGCGGAGGGACCNAGCTGACCG

TCCTANGTGCGGCCGC-3'

39
(SEQ ID NO: 27)
5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCAAGTATTACTTCTTCTGGTGATTCTACATCTTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAATATAGTAGTGATTTTGACTACTGGGGCCAGG

GAACCCTGGTCACCGTCTCGAGCGGTGGAGGCGGTTCAGGCGGAGGTG

GCAGCGGCGGTGGCGGGTCGACGGACATCCAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATTCTGCATCCGCTTTGCAAAGTG

GGGTCCCAACAAGGTTCAGTGGCAGTGGATCTGGGACAGATTTCACTC

TCACCATCAGCAGTCTGCAACCTGAAGATTTTGCAACTTACTACTGTC

AACAGGCTAATACTACTCCTACTACGTTCNGNCCAAGGGNCCNAGGTG

GAAATCAAACGGGCNGGCCGCACATCATCATCACCATCACGGGGCNNC

AGAANAAAAACTCATCTCANAANANNNTCTGAATGGGGCCGNATAGAC

TGNTGAAAGTNGTTTAGCAAANNTNNTACNGAAAATTCATTTACTANG

TCTGGAAAGACGANNAANTTTNNATCGTNACNCTNNCTNNNNNNNTGN

CNGNNNNNGCTACNNNNNNNNNNNNNNNACNGNGA-3'

41
(SEQ ID NO: 28)
5'-CCATGGCCGAGGTGCAGCTGTTGGAGTCTGGGGGAGGCTTGGTAC

AGCCTGGGGGGTCCCTGAGACTCTCCTGTGCAGCCTCTGGATTCACCT

TTAGCAGCTATGCCATGAGCTGGGTCCGCCAGGCTCCAGGGAAGGGGC

TGGAGTGGGTCTCATCTATTTAGCCTACTGGTAGGCGGACATCGTACG

CAGACTCCGTGAAGGGCCGGTTCACCATCTCCAGAGACAATTCCAAGA

ACACGCTGTATCTGCAAATGAACAGCCTGAGAGCCGAGGACACGGCCG

TATATTACTGTGCGAAAAGTCGTACGCCGTTTGACTACTGGGGCCAGG

GAACCCTGGTCACCGTCTCGAGCGGTGGAGGCGGTTCAGGCGGAGGTG

GCAGCGGCGGTGGCGGGTCGACGGACATCCAGATGACCCAGTCTCCAT

CCTCCCTGTCTGCATCTGTAGGAGACAGAGTCACCATCACTTGCCGGG

CAAGTCAGAGCATTAGCAGCTATTTAAATTGGTATCAGCAGAAACCAG

GGAAAGCCCCTAAGCTCCTGATCTATTCTGCATCCATCTTGCAAAGTG

GGGTCCCATCAAGGTTCAGTGGCAGTGGATCTGGGACAGATTTCACTC

TCACCATCAGCAGTCTGCAACCTGAAGATTTTGCAACTTACTACTGTC

NACAGANTACGCCTGCTCCTGGGACGTTCGGCCAAGGGACCAAGGTGG

AAATCAAACGGGCGGNCGCACATCATCATCACCATCACGGGNNNGCAG

AANAAAAACTCATCTCNNNNNNNNATCTGAATGGGGCNNCNTANACTGN

TGAAAGTGTTAGCNAANNTNNNNNNGAAAANTNNNTTNCTAACNNCTN

GAANA-3'

Figure 12A:
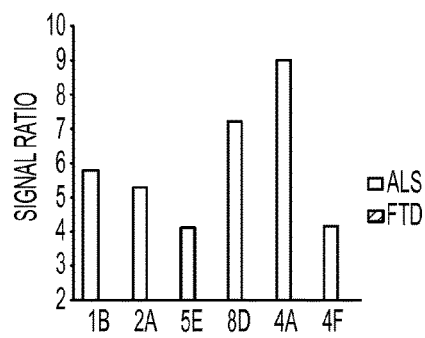
FIGS. 12A-C. A. ALS TDP-43 phage capture ELISA with human brain tissue (Monomer phage #3 used for detection). B. ALS TDP-43 phage capture ELISA with human brain tissue (monomer phage #5 used for detection). C. ALS TDP-43 phage capture ELISA with human brain tissue (commercial anti-TDP43 antibody used for detection).
Figure 12B:
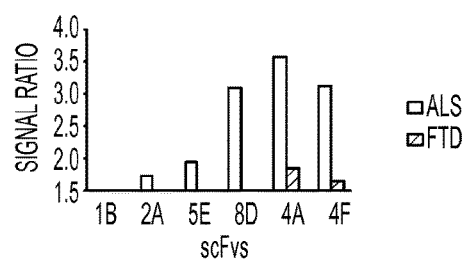

For three out of the five clones (#5, #3 and #39), the binding pattern across the three different brain tissue samples is similar to the results utilizing the commercial TDP-43 antibody. Application of the entire phage capture ELISA process using scFvs from six of the clones and the potential monomer phages with ALS, FTD and healthy human brain tissue produced greater signal ratios with ALS versus FTD for both monomer phages #3 and #5 (FIGS. 12A and B). The monomer phage was tagged with a signal moiety, and then utilized to determine the presence of any of the captured variants.

Figure 12C:
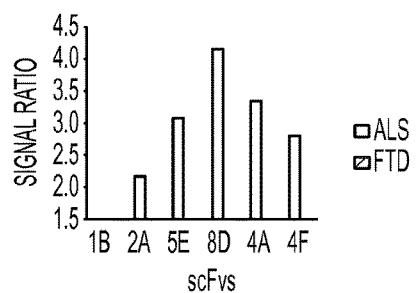
Figure 13A:
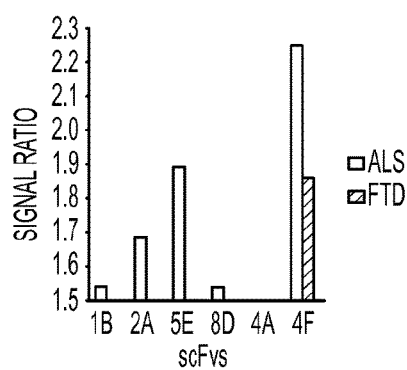
FIGS. 13A-C. A. ALS TDP-43 phage capture ELISA with IP TDP-43 (monomer phage #3 used for detection). B. ALS TDP-43 phage capture ELISA with IP TDP-43 (monomer phage #5 used for detection). C. ALS TEP-43 phage capture ELISA with IP TDP-43 (commercial anti-TDP 43 antibody used for detection).
Figure 13B:
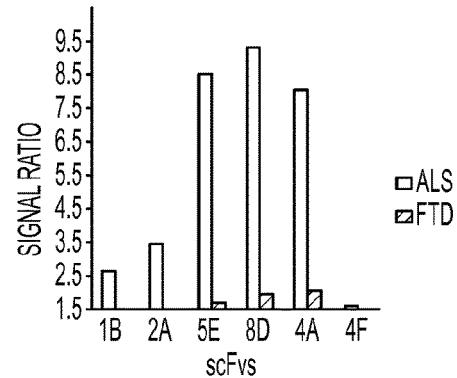
Figure 13C:
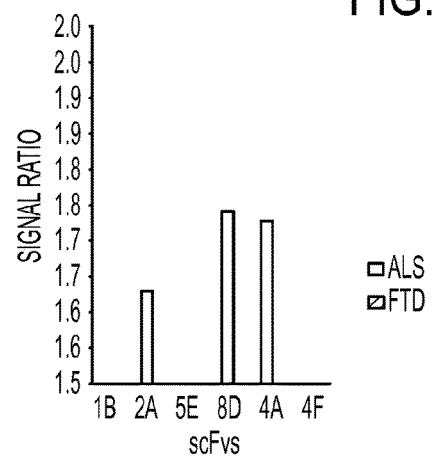

To ascertain whether the target bound to the capture scFvs is a TDP-43 protein, a commercial TDP-43 antibody was utilized instead of the monomer phage for detection. Elevated signals were detected for most clones with ALS tissue compared to FTD (FIG. 12C). Carrying out similar experiments as in FIGS. 12A, B and C but with TDP-43 proteins that were immunoprecipitated (IP) from ALS, FTD and healthy human brain tissue again showed a preference for ALS IP TDP-43 compared to FTD IP TDP-43 for both monomer phages #3 and #5 (FIGS. 13A and B) and the commercial TDP-43 antibody (FIG. 13C). The signals with monomer phage #5 were considerably greater than phage #3 and therefore monomer phage #5 seemed like a better choice.

Figure 14:
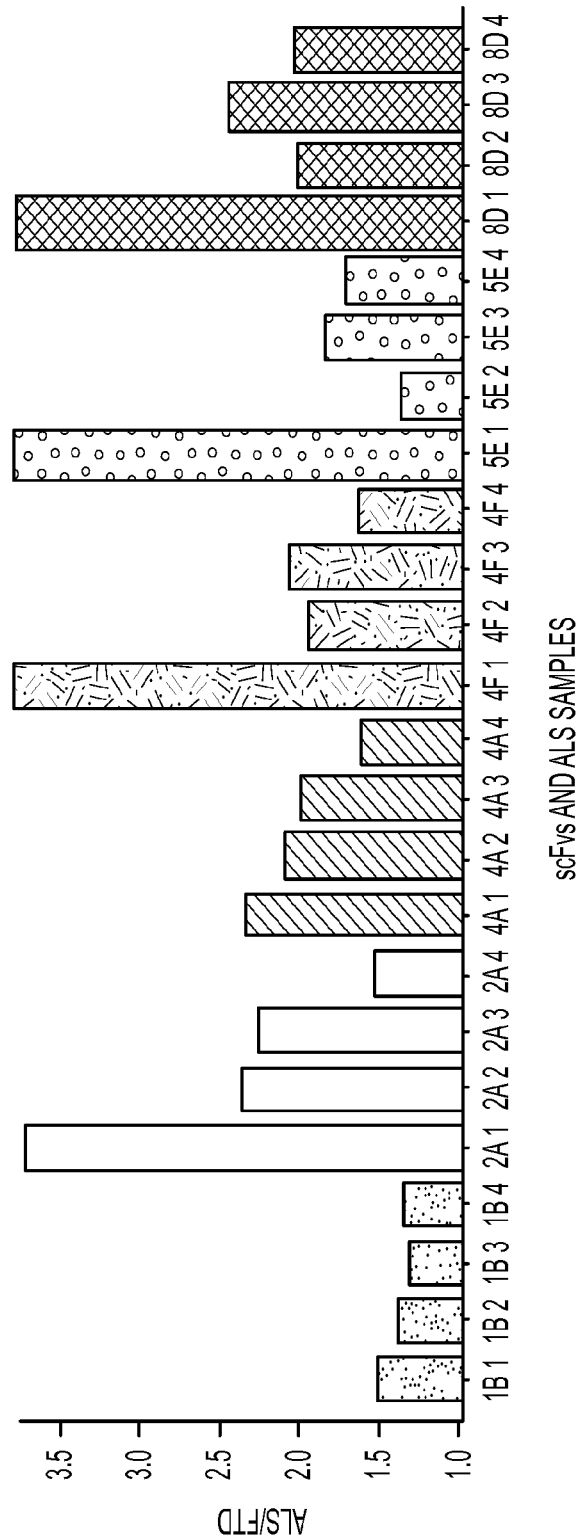
FIG. 14. scFvs from ALS TDP-43 clones in phage capture ELISA with 4 different ALS, FTD and healthy human brain tissue samples.
Figure 15A:
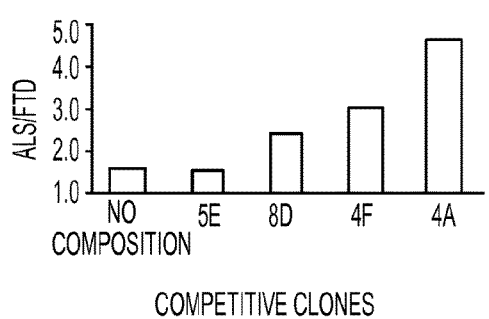
FIGS. 15A-C. A. Competition ELISA with ALS Capture scFv 2A. B. Competition ELISA with ALS Capture scFv 5E. C. Competition ELISA with ALS Capture scFv 8D.
Figure 15B:
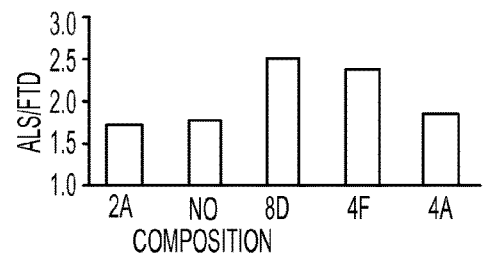
Figure 15C:
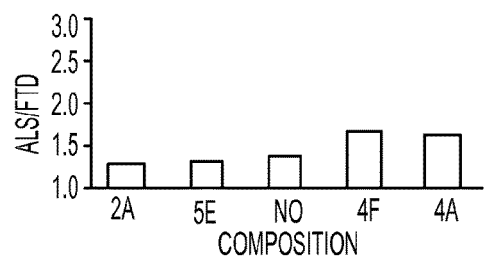

In previous ELISAs the inventors used either pooled or one brain sample from each of the three groups. To determine which clones would display reactivity with multiple samples from each group six clones were tested with four ALS, FTD and healthy human brain tissue individually. All six clones exhibited greater reactivity with all four ALS samples compared to FTD in this phage capture ELISA (FIG. 14). The pattern and level of reactivity varied across the clones suggesting that clones were reactive with different conformations of TDP-43. In a preliminary competition phage capture ELISA experiment, the wells were coated with the different scFvs and then incubated with ALS, FTD or healthy human brain tissue as usual. However, prior to this step each of the different brain tissue were incubated in solution with the different scFvs. The scFvs recognize and bind their targets. When the brain tissue is then added to the ELISA wells with the already bound capture scFv if the capture scFv recognizes the same target as the scFv with which the tissue was previously incubated with, there is no signal during detection since binding was prevented. The results of three of the clones are shown in FIGS. 15A, B and C. The bar labeled no competition means that the tissue added to this well was not incubated with any scFv and therefore represent the baseline binding for that particular scFv. The binding of these three scFvs were not inhibited by their four competitive clones, suggesting reactivity with different TDP-43 epitopes.

Figure 16A:
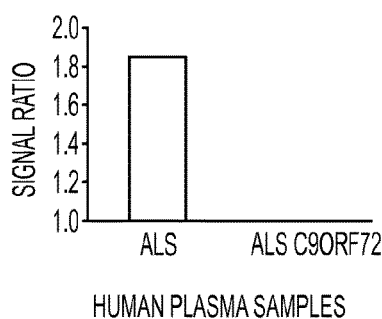
FIGS. 16A-C. Indirect phage ELISA with human plasma samples using ALS TDP-43 clone 5H. B. indirect phage ELISA with human plasma samples using ALS TDP-43 clone 8D. C. Indirect phage ELISA with human plasma samples using ALS TDP-43 clone 8E.
Figure 16B:
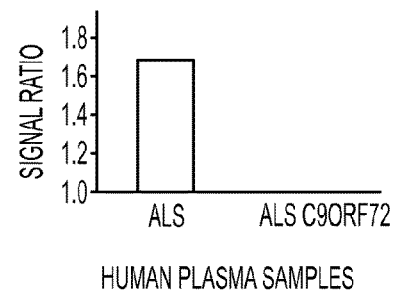
Figure 16C:
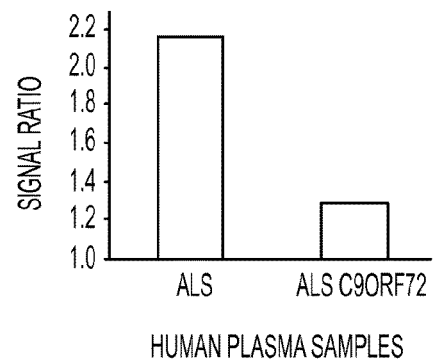

Since these 23 clones were initially isolated for binding to ALS TDP-43 an indirect phage ELISA was carried out using pooled ALS plasma samples. The binding to ALS plasma relative to the controls for some of the clones are illustrated in FIGS. 16 A, B and C. ALS C9ORF72 is a genetic mutation thought to be related to familial ALS. Overall, elevated binding to ALS compared to ALS COORF72 was observed with the three clones.

Example 6

Single Chain Variable Fragments Isolated Utilizing FTD TDP-43

Clones were isolated that preferentially bound TDP-43 present in FTD compared to ALS brain tissue. Out of the 100 clones isolated after the positive panning against FTD IP TDP-43, approximately 70% of the clones had a complete sequence without any stop codons or frameshift mutations.

Figure 17:
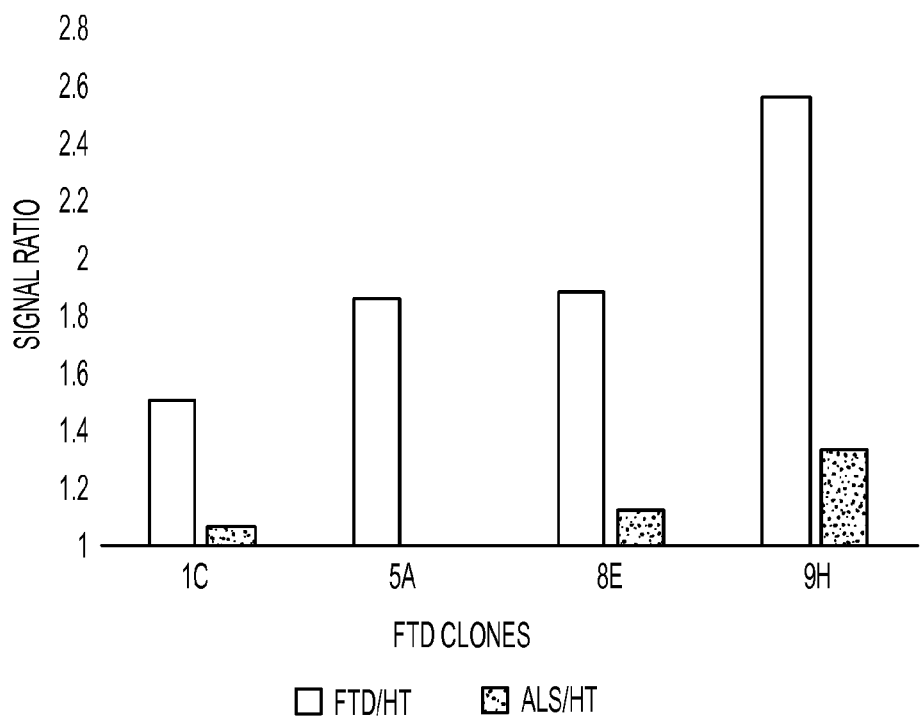
FIG. 17. Phage Capture ELISA with FTD and ALS tissue.

Clones that were able to differentiate FTD over ALS and healthy tissue were further transformed into competent HB cells to generate scFvs. Sequence was verified and supernatant (NOT concentrated) produced to test these clones in a sandwich ELISA. Most of the clones showed high binding to FTD over healthy tissue and ALS confirming that the negative panning worked (FIG. 17).

Figure 18:
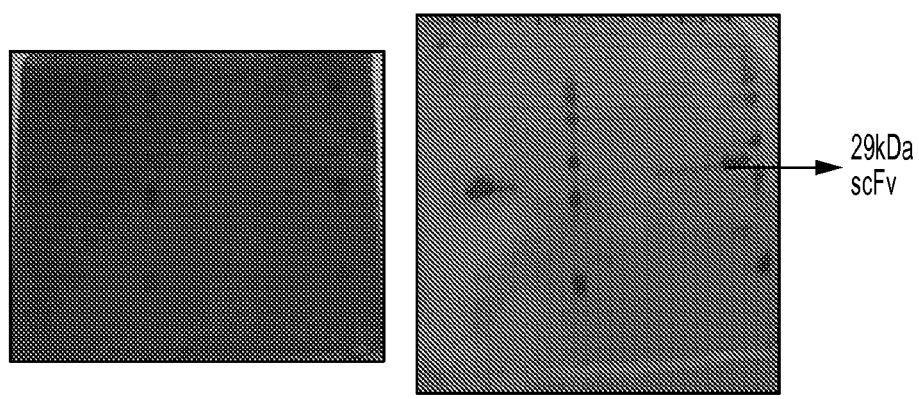
FIG. 18. scFv Production of FTD TDP-43 Clones.

The scFv was also purified using a protein A column in a FPLC machine. SDS-PAGE gel and Western blot analyses verified that the scFv produced was of the correct molecular weight of ~29 kDa (FIG. 18).

REFERENCES

1. Barkhordarian, H., et al., *Isolating recombinant antibodies against specific protein morphologies using atomic force microscopy and phage display technologies.* Protein Eng Des Sel, 2006. 19: p. 497-502.
2. Emadi, S., et al., *Isolation of a human single chain antibody fragment against oligomeric alphasynuclein that inhibits aggregation and prevents alpha-synuclein-induced toxicity.* J Mol Biol, 2007. 368: p. 1132-44.
3. Emadi, S., et al., *Detecting morphologically distinct oligomeric forms of alpha-synuclein.* J Biol Chem, 2009. 284: p. 11048-58.
4. Emadi, S., et al., *Inhibiting Aggregation of alpha-Synuclein with Human Single Chain Antibody Fragments.* Biochemistry, 2004. 43: p. 2871-2878.
5. Yuan, B. and M. R. Sierks, *Intracellular targeting and clearance of oligomeric alpha-synuclein alleviates toxicity in mammalian cells.* Neurosci Lett, 2009. 459: p. 16-8.
6. Zameer, A., et al., *Anti-oligomeric Abeta single-chain variable domain antibody blocks Abeta-induced toxicity against human neuroblastoma cells.* J Mol Biol, 2008. 384: p. 917-28.
7. Zameer, A., et al., *Single Chain Fv Antibodies against the 25-35 Abeta Fragment Inhibit Aggregation and Toxicity of Abeta42.* Biochemistry, 2006. 45: p. 11532-9.
8. Mackenzie, I. R., R. Rademakers, and M. Neumann, *TDP-43 and FUS in amyotrophic lateral sclerosis and frontotemporal dementia.* Lancet Neurol. 9: p. 995-1007.
9. Johnson, B. S., et al., *TDP-43 is intrinsically aggregation-prone, and amyotrophic lateral sclerosis-linked mutations accelerate aggregation and increase toxicity.* J Biol Chem, 2009. 284: p. 20329-39.
10. Flood, D. G., G. J. Marek, and M. Williams, *Developing predictive CSF biomarkers—A challenge critical to success in Alzheimer's disease and neuropsychiatric translational medicine.* Biochem Pharmacol. 81: p. 1422-34.
11. Georganopoulou, D. G., et al., *Nanoparticle-based detection in cerebral spinal fluid of a soluble pathogenic biomarker for Alzheimer's disease.* Proc Natl Acad Sci USA, 2005. 102: p. 2273-6.
12. El-Agnaf, O. M., et al., *Detection of oligomeric forms of alpha-synuclein protein in human plasma as a potential biomarker for Parkinson's disease.* Faseb J, 2006. 20: p. 419-25.
13. Meraz-Rios, M. A., et al., *Tau oligomers and aggregation in Alzheimer's disease.* J Neurochem. 112: p. 1353-67.
14. Hu, W. T., J. Q. Trojanowski, and L. M. Shaw, *Biomarkers in frontotemporal lobar degenerations-Progress and challenges.* Prog Neurobiol.
15. Buratti, E. and F. E. Baralle, *Multiple roles of TDP-43 in gene expression, splicing regulation, and human disease.* Front Biosci, 2008. 13: p. 867-78.
16. Buratti, E., et al., *Nuclear factor TDP-43 binds to the polymorphic TG repeats in CFTR intron 8 and causes skipping of exon 9: a functional link with disease penetrance.* Am J Hum Genet, 2004. 74: p. 1322-5.
17. Wilson, A. C., et al., *TDP-43 in aging and Alzheimer's disease—a review.* Int J Clin Exp Pathol. 4: p. 147-55.
18. Uryu, K., et al., *Concomitant TAR-DNA-binding protein 43 pathology is present in Alzheimer disease and corticobasal degeneration but not in other tauopathies.* J Neuropathol Exp Neurol, 2008. 67: p. 555-64.
19. Dickson, D. W., *TDP-43 immunoreactivity in neurodegenerative disorders: disease versus mechanism specificity.* Acta Neuropathol, 2008. 115: p. 147-9.
20. Amador-Ortiz, C., et al., *TDP-43 immunoreactivity in hippocampal sclerosis and Alzheimer's disease.* Ann Neurol, 2007. 61: p. 435-45.
21. Herman, A. M., et al., *beta Amyloid triggers ALS-associated TDP-43 pathology in AD models.* Brain Res. 1386: p. 191-9.
22. Liu, R., et al., *Single chain variable fragments against beta-amyloid (Abeta) can inhibit Abeta aggregation and prevent abeta-induced neurotoxicity.* Biochemistry, 2004. 43: p. 6959-67.
23. Kasturirangan, S., et al., *Nanobody specific for oligomeric beta-amyloid stabilizes non-toxic form.* Neurobiol Aging, 2010. In press: p.
24. Walsh, D. M., et al., *Naturally secreted oligomers of amyloid beta protein potently inhibit hippocampal long-term potentiation in vivo.* Nature, 2002. 416: p. 535-9.
25. Walsh, D. M. and D. J. Selkoe, *Abeta Oligomers—a decade of discovery.* J Neurochem, 2007.
26. Shlyakhtenko, L. S., et al., *Single-molecule selection and recovery of structure-specific antibodies using atomic force microscopy.* Nanomedicine, 2007. 3: p. 192-7.
27. Graber, D. J., W. F. Hickey, and B. T. Harris, *Progressive changes in microglia and macrophages in spinal cord and peripheral nerve in the transgenic rat model of amyotrophic lateral sclerosis.* J Neuroinflammation. 7: p. 8.
28. Graber, D. J., et al., *Synthetic triterpenoid CDDO derivatives modulate cytoprotective or immunological properties in astrocytes, neurons, and microglia.* J Neuroimmune Pharmacol. 6: p. 107-20.

29. Stommel, E. W., et al., *Tumor necrosis factor-alpha induces changes in mitochondrial cellular distribution in motor neurons.* Neuroscience, 2007. 146: p. 1013-9.
30. Ullian, E. M., et al., *Schwann cells and astrocytes induce synapse formation by spinal motor neurons in culture.* Mol Cell Neurosci, 2004. 25: p. 241-51.
31. Farmer, J., et al., *Coexisting adult polyglucosan body disease with frontotemporal lobar degeneration with transactivation response DNA-binding protein-43 (TDP-43)-positive neuronal inclusions.* Neurocase, 2011. In press: p.
32. Hu, W. T., et al., *Novel CSF biomarkers for frontotemporal lobar degenerations.* Neurology. 75: p. 2079-86.
33. Noto, Y., et al., *Elevated CSF TDP-43 levels in amyotrophic lateral sclerosis: specificity, sensitivity, and a possible prognostic value.* Amyotroph Lateral Scler. 12: p. 140-3.
34. Mackenzie, I. R., et al., *Nomenclature and nosology for neuropathologic subtypes of frontotemporal lobar degeneration: an update.* Acta Neuropathol. 119: p. 1-4.
35. Swarup, V., et al., *Pathological hallmarks of amyotrophic lateral sclerosis/frontotemporal lobar degeneration in transgenic mice produced with TDP-43 genomic fragments.* Brain. 134: p. 2610-26.
36. Zhou, C., et al., *A human single-chain Fv intrabody blocks aberrant cellular effects of overexpressed alpha-synuclein.* Mol Ther, 2004. 10: p. 1023-31.
37. Wang, M. S., et al., *Characterizing Antibody Specificity to Different Protein Morphologies by AFM.* Langmuir, 2008.
38. Kasturirangan, S., et al., *Isolation and Characterization of a Nanobody that Selectively Binds Brain Derived Oligomeric Beta-Amyloid* (Submitted).
39. Marcus, W. D., et al., *Characterization of an antibody scFv that recognizes fibrillar insulin and betaamyloid using atomic force microscopy.* Nanomedicine, 2008. 4: p. 1-7.
40. Liu, R., et al., *Residues 17-20 and 30-35 of beta-amyloid play critical roles in aggregation.* J Neurosci Res, 2004. 75: p. 162-71.
41. Liu, R., et al., *Proteolytic antibody light chains alter beta-amyloid aggregation and prevent cytotoxicity.* Biochemistry, 2004. 43: p. 9999-10007.
42. Marcus, W. D., et al., *Isolation of an scFv targeting BRG1 using phage display with characterization by AFM.* Biochem Biophys Res Commun, 2006. 342: p. 1123-9.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An antibody fragment comprising an amino acid sequence encoded by a nucleic acid, wherein the nucleic acid has at least 96% identity to SEQ ID NO:1.

2. The antibody fragment of claim 1, wherein the nucleic acid has at least 97% identity to SEQ ID NO: 1.

3. The antibody fragment of claim 1, wherein the nucleic acid has at least 98% identity to SEQ ID NO:1.

4. The antibody fragment of claim 1, wherein the nucleic acid has at least 99% identity to SEQ ID NO:1.

5. The antibody fragment of claim 1, wherein the nucleic acid has 100% identity to SEQ ID NO:1.

6. A binding molecule that binds to TAR DNA binding protein 43 (TDP-43) associated with Amyotrophic Lateral Sclerosis (ALS) and does not bind TDP-43 from healthy human brain tissue or TDP-43 associated with Frontotemporal Degeneration (FTP), wherein the binding molecule comprises an amino acid sequence encoded by a nucleic acid, wherein the nucleic acid has at least 96% identity to SEQ ID NO:1.

7. The binding molecule of claim 6, wherein the nucleic acid has at least 97% identity to SEQ ID NO:1.

8. The binding molecule of claim 6, wherein the nucleic acid has at least 98% identity to SEQ ID NO:1.

9. The binding molecule of claim 6, wherein the nucleic acid has at least 99% identity to SEQ ID NO:1.

10. The binding molecule of claim 6, wherein the nucleic acid has 100% identity to SEQ ID NO:1.

11. A method of binding TDP-43 associated with ALS comprising contacting a composition that comprises TDP-43 associated with ALS with an antibody fragment or binding molecule of any one of claim 1 or 6.

12. The method of claim 11, wherein the TDP-43 associated with ALS is in a cell.

13. The method of claim 11, wherein the TDP-43 associated with ALS is in brain tissue.

14. An imaging composition specific for TDP-43 associated with ALS comprising an antibody fragment or a binding molecule of any one of claim 1 or 6 conjugated to an imaging agent.

* * * * *

SEQUENCE LISTING

```
<160> NUMBER OF SEQ ID NOS: 29

<210> SEQ ID NO 1
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
ccatggccga ggtgcagctg ttggagtctg ggggaggctt ggtacagcct gggggtccc       60 cgagactctc ctgtgcagcc tctggattca cctttagcag ctatgccatg agctgggtcc     120
gccaggctcc agggaagggg ctggagtggg tctcaactat ttctgcttct ggtacttata    180
caaattacgc agactccgtg aagggccggt tcaccatctc cagagacaat tccaagaaca    240
```

```
cgctgtatct gcaaatgaac agcctgagag ccgaggacac ggccgtatat tactgtgcga    300
aaacttcttc ttattttgac tactggggcc agggaaccct ggtcaccgtc tcgagcggtg    360
gaggcggttc aggcggaggt ggcagcggcg gtggcgggtc gacggacatc cagatgaccc    420
agtctccatc ctccctgtct gcatctgtag gagacagagt caccatcact gccgggcaa    480 gtcagagcat tagcagctat ttaaattggt atcagcagaa accagggaaa gcccctaagc    540
tcctgatcta tgctgcatcc aatttgcaaa gtggggtccc atcaaggttc agtggcagtg    600
gatctgggac agatttcact ctcaccatca gcagtctgca acctgaagat tttgcaactt    660
actactgtca acaggataat tatgctcctt atacgttcgg ccaagggacc aaggtggaaa    720
tcaaacgggc ggccgc                                                    736
```

<210> SEQ ID NO 2
<211> LENGTH: 514
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
ccatggccga ggtgcagctg ttggagtctg ggggaggctt ggtacagcct ggggggtccc     60
tgagactctc ctgtgcagcc tctggattca cctttagcag ctatgccatg agctgggtcc    120
gccaggctcc agggaagggg ctggagtggg tctcaactat tgccatgct ggtcagtcga    180 cggacatcca gatgacccag tctccatcct ccctgtctgc atctgtagga gacagagtca    240
ccatcacttg ccgggcaagt cagagcatta gcagctattt aaattggtat cagcagaaac    300
cagggaaagc ccctaagctc ctgatctata tggcatcccg tttgcaaagt ggggtcccat    360
caaggttcag tggcagtgga tctgggacag atttcactct caccatcagc agtctgcaac    420
ctgaagattt tgcaacttac tactgtcaac agcagcgtac gaagcctcct acgttcggcc    480
aagggaccaa ggtggaaatc aaacgggcgg ccgc                               514
```

<210> SEQ ID NO 3
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
ccatggccga ggtgcagctg ttggagtctg ggggaggctt ggtacagcct ggggggtccc     60
tgagactctc ctgtgcagcc tctggattca cctttagcag ctatgccatg agctgggtcc    120
gccaggctcc agggaagggg ctggagtggg tctcaactat tgcttctgct ggtactgata    180
cagcttacgc agactccgtg aagggccggt tcaccatctc cagagacaat tccaagaaca    240
cgctgtatct gcaaatgaac agcctgagag ccgaggacac ggccgtatat tactgtgcga    300
aagatactac tgcttttgac tactggggcc agggaaccct ggtcaccgtc tcgagcggtg    360
gaggcggttc aggcggaggt ggcagcggcg gtggcgggtc gacggacatc aagatgaccc    420
agtctccatc ctccctgtct gcatctgtag gagacagagt caccatcact gccgggcaa    480 gtcagagcat tagcagctat ttaaattggt atcagcagaa accagggaaa gcccctaagc    540
tcctgatcta tgatgcatcc actttgcaaa gtggggtccc atcaaggttc agtggcagtg    600
gatctgggac agatttcact ctcaccatca gcagtctgca acctgaagat tttgcaactt    660
```

```
actactgtca acagtctact tatgctcctg ctacgttcgg ccaagggacc aaggtggaaa    720
tcaaacgggc ggccgc                                                   736

<210> SEQ ID NO 4
<211> LENGTH: 436
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
ccatggccga ggtgtttgac tactggggcc agggaaccct ggtcaccgtc tcgagcggtg     60
gaggcggttc aggcggaggt ggcagcggcg gtggcgggtc gacggacatc cagatgaccc    120
agtctccatc ctccctgtct gcatctgtag gagacagagt caccatcact tgccgggcaa    180
gtcagagcat tagcagctat ttaaattggt atcagcagaa accagggaaa gcccctaagc    240
tcctgatcta ttctgcatcc aatttgcaaa gtggggtccc atcaaggttc agtggcagtg    300
gatctgggac agatttcact ctcaccatca gcagtctgca acctgaagat tttgcaactt    360
actactgtca acagagttat tctagtcctt ctacgttcgg ccaagggacc aaggtggaaa    420
tcaaacgggc ggccgc                                                   436

<210> SEQ ID NO 5
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
ccatggccga ggtgcagctg ttggagtctg ggggaggctt ggtacagcct ggggggtccc     60
tgagactctc ctgtgcagcc tctggattca cctttagcag ctatgccatg agctgggtcc    120
gccaggctcc agggaagggg ctggagtggg tctcatctat taataatgct ggtatgatac    180
aaattacgca gactccgtga agggcaggtt caccatctcc agagacaatt ccaagaacac    240
gctgtatctg caaatgaaca gcctgagagc cgaggacacg gccgtatatt actgtgcgaa    300
aaataatgct tattttgact actggggcca gggaaccctg gtcaccgtct cgagcggtgg    360
aggcggttca ggcggaggtg gcagcggcgg tggcgggtcg acggacatcc agatgaccca    420
gtctccatcc tccctgtctg catctgtagg agacagagtc accatcactt gccgggcaag    480
tcagagcatt agcagctatt taaattggta tcagcagaaa ccagggaaag cccctaagct    540
cctgatctat tctgcatcca atttgcaaag tggggtccca tcaaggttca gtggcagtgg    600
atctgggaca gatttcactc tcaccatcag cagtctgcaa cctgaagatt ttgcaactta    660
ctactgtcaa cagtatgatt ctgctcctgg tacgttcggc caagggacca aggtggaaat    720
caaacgggcg gccgc                                                    735

<210> SEQ ID NO 6
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
```

```
ccatggccga ggtgcagctg ttggagtctg ggggaggctt ggtacagcct ggggggtccc    60
tgagactctc ctgtgcagcc tctggattca cctttagcag ctatgccatg agctgggtcc   120
gccaggctcc agggaagggg ctggagtggg tctcaactat taataatagt ggtacttcta   180
caaattacgc agactccgtg aagggccggt tcaccatctc cagagacaat tccaagaaca   240
cgctgtatct gcaaatgaac agcctgagag ccgaggacac ggccgtatat tactgtgcga   300
aaagtactaa ttattttgac tactgggggcc agggaaccct ggtcaccgtc tcgagcggtg   360
gaggcggttc aggcggaggt ggcagcggcg gtggcgggtc gacggacatc cagatgaccc   420
agtctccatc ctccctgtct gcatctgtag gagacagagt caccatcact tgccgggcaa   480
gtcagagcat tagcagctat ttaaattggt atcagcagaa accagggaaa gcccctaagc   540
tcctgatcta tgctgcatcc agtttgcaaa gtggggtccc atcaaggttc agtggcagtg   600
gatctgggac agatttcact ctcaccatca gcagtctgca acctgaagat tttgcaactt   660
actactgtca acagaatgct gctgatccta ctacgttcgg ccaagggacc aaggtggaaa   720
tcaaacgggc ggccgc                                                   736

<210> SEQ ID NO 7
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
ccatggccga ggtgcagctg ttggagtctg ggggaggctt ggtacagcct ggggggtccc    60
tgagactctc ctgtgcagcc tctggattca cctttagcag ctatgccatg agctgggtcc   120
gccaggctcc agggaagggg ctggagtggg tctcaggtat ttctagttct ggtaatacta   180
caacttacgc agactccgtg aagggccggt tcaccatctc cagagacaat tccaagaaca   240
cgctgtatct gcaaatgaac agcctgagag ccgaggacac ggccgtatat tactgtgcga   300
aagatggtgc tacttttgac tactgggggcc agggaaccct ggtcaccgtc tcgagcggtg   360
gaggcggttc aggcggaggt ggcagcggcg gtggcgggtc gacggacatc cagatgaccc   420
agtctccatc ctccctgtct gcatctgtag gagacagagt caccatcact tgccgggcaa   480
gtcagagcat tagcagctat ttaaattggt atcagcagaa accagggaaa gcccctaagc   540
tcctgatcta ttctgcatcc tctttgcaaa gtggggtccc atcaaggttc agtggcagtg   600
gatctgggac agatttcact ctcaccatca gcagtctgca acctgaagat tttgcaactt   660
actactgtca acagtatgat ggttctcctg atacgttcgg ccaagggacc aaggtggaaa   720
tcaaacgggc ggccgc                                                   736

<210> SEQ ID NO 8
<211> LENGTH: 436
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
ccatggccga ggtgtttgac tactggggcc agggaaccct ggtcaccgtc tcgagcggtg    60
gaggcggttc aggcggaggt ggcagcggcg gtggcgggtc gacggacatc cagatgaccc   120
```

| | |
|---|---|
| agtctccatc ctccctgtct gcatctgtag agacagagt caccatcact tgccgggcaa | 180 |
| gtcagagcat tagcagctat ttaaattggt atcagcagaa accagggaaa gcccctaagc | 240 |
| tcctgatcta ttctgcatcc actttgcaaa gtggggtccc atcaaggttc agtggcagtg | 300 |
| gatctgggac agatttcact ctcaccatca gcagtctgca acctgaagat tttgcaactt | 360 |
| actactgtca acagggtgat actaatccta gtacgttcgg ccaagggacc aaggtggaaa | 420 |
| tcaaacgggc ggccgc | 436 |

<210> SEQ ID NO 9
<211> LENGTH: 736
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

| | |
|---|---|
| ccatggccga ggtgcagctg ttggagtctg ggggaggctt ggtacagcct ggggggtccc | 60 |
| tgagactctc ctgtgcagcc tctggattca cctttagcag ctatgccatg agctgggttc | 120 |
| gccaggctcc agggaagggg ctggagtggg tctcaagtat tgctagttct ggtgatgata | 180 |
| caaattacgc agactccgtg aagggccggt tcaccatctc cagagacaat tccaagaaca | 240 |
| cgctgtatct gcaaatgaac agcctgagag ccgaggacac ggccgtatat tactgtgcga | 300 |
| aaactgctag tagttttgac tactggggcc agggaaccct ggtcaccgtc tcgagcggtg | 360 |
| gaggcggttc aggcggaggt ggcagcggcg gtggcgggtc gacggacatc cagatgaccc | 420 |
| agtctccatc ctccctgtct gcatctgtag agacagagt caccatcact tgccgggcaa | 480 |
| gtcagagcat tagcagctat ttaaattggt atcagcagaa accagggaaa gcccctaagc | 540 |
| tcctgatcta ttctgcatcc tctttgcaaa gtggggtccc atcaaggttc agtggcagtg | 600 |
| gatctgggac agatttcact ctcaccatca gcagtctgca acctgaagat tttgcaactt | 660 |
| actactgtca acagactaat ggtaatccta atacgttcgg ccaagggacc aaggtggaaa | 720 |
| tcaaacgggc ggccgc | 736 |

<210> SEQ ID NO 10
<211> LENGTH: 736
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

| | |
|---|---|
| ccatggccga ggtgcagctg ttggagtctg ggggaggctt ggtacagcct ggggggtccc | 60 |
| tgagactctc ctgtgcagcc tctggattca cctttagcag ctatgccatg agctgggtcc | 120 |
| gccaggctcc agggaagggg ctggagtggg tctcagctat ttctaatgat ggtaataata | 180 |
| cagattacgc agactccgtg aagggcaggt tcaccatctc cagagacaat tccaagaaca | 240 |
| cgctgtatct gcaaatgaac agcctgagag ccgaggacac ggccgtatat tactgtgcga | 300 |
| aaactgattc tacttttgac tactggggcc agggaaccct ggtcaccgtc tcgagcggtg | 360 |
| gaggcggttc aggcggaggt ggcagcggcg gtggcgggtc gacggacatc cagatgaccc | 420 |
| agtctccatc ctccctgtct gcatctgtag agacagagt caccatcact tgccgggcaa | 480 |
| gtcagagcat tagcagctat ttaaattggt atcagcagaa accagggaaa gcccctaagc | 540 |
| tcctgatcta ttctgcatcc aatttgcaaa gtggggtccc atcaaggttc agtggcagtg | 600 |

```
gatctgggac agatttcact ctcaccatca gcagtctgca acctgaagat tttgcaactt    660
actactgtca acagagtgct gatagtccta ctacgtttgg ccaagggacc aaggtggaaa    720
tcaaacgggc ggccgc                                                    736

<210> SEQ ID NO 11
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
ccatggccga ggtgcagctg ttggagtctg ggggaggctt ggtacagcct ggggggtccc     60
tgagactctc ctgtgcagcc tctggattca cctttagcag ctatgccatg agctgggtcc    120
gccaggctcc agggaagggg ctggagtggg tctcagatat tggtggtgat ggttataata    180
catcttacgc agactccgtg aagggccggt tcaccatctc cagagacaac tccaagaaca    240
cgctgtatct gcaaatgaac agcctgagag ccgaggacac ggccgtatat tactgtgcga    300
aaagttatac tgcttttgac tactggggcc agggaaccct ggtcaccgtc tcgagcggtg    360
gaggcggttc aggcggaggt ggcagcggcg gtggcgggtc gacggacatc cagatgaccc    420
agtctccatc ctccctgtct gcatctgtag gagacagagt caccatcact tgccgggcaa    480
gtcagagcat tagcagctat ttaaattggt atcagcagaa accagggaaa gcccctaagc    540
tcctgatcta ttctgcatcc ggtttgcaaa gtggggtccc atcaaggttc agtggcagtg    600
gatctgggac agatttcact ctcaccatca gcagtctgca acctgaagat tttgcaactt    660
actactgtca acaggatact aatggtcctt ctacgttcgg ccaagggacc aaggtggaaa    720
tcaaacgggc ggccgc                                                    736

<210> SEQ ID NO 12
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
ccatggccga ggtgcagctg ttggagtctg ggggaggctt ggtacagcct ggggggtccc     60
tgagactctc ctgtgcagcc tctggattca cctttagcag ctatgccatg agctgggtcc    120
gccaggctcc agggaagggg ctggagtggg tctcaagtat ttattctgat ggtggtgcta    180
catcttacgc agactccgtg aagggccggt tcaccatctc cagagacaat tccaagaaca    240
cgctgtatct gcaaatgaac agcctgagag ccgaggacac ggccgtatat tactgtgcga    300
aagctactgc tacttttgac tactggggcc agggaaccct ggtcaccgtc tcgagcggtg    360
gaggcggttc aggcggaggt ggcagcggcg gtggcgggtc gacggacatc cagatgaccc    420
agtctccatc ctccctgtct gcatctgtag gagacagagt caccatcact tgccgggcaa    480
gtcagagcat tagcagctat ttaaattggt atcagcagaa accagggaaa gcccctaagc    540
tcctgatcta ttctgcatcc gctttgcaaa gtggggtccc atcaaggttc agtggcagtg    600
gatctgggac agatttcact ctcaccatca gcagtctgca acctgaagat tttgcaactt    660
actactgtca acagtcttct actagtccta gtacgttcgg ccaagggacc aaggtggaaa    720
```

```
tcaaacgggc ggccgc                                                     736
```

<210> SEQ ID NO 13
<211> LENGTH: 436
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
ccatggccga ggtgtttgac tactggggcc agggaaccct ggtcaccgtc tcgagcggtg     60
gaggcggttc aggcggaggt ggcagcggcg gtggcgggtc gacggacatc cagatgaccc    120
agtctccatc ctccctgtct gcatctgtag gagacagagt caccatcact tgccgggcaa    180
gtcagagcat tagcagctat ttaaattggt atcagcagaa accagggaaa gcccctaagc    240
tcctgatcta tactgcatcc tctttgcaaa gtggggtccc atcaaggttc agtggcagtg    300
gatctgggac agatttcact ctcaccatca gcagtctgca acctgaagat tttgcaactt    360
actactgtca acagagtgct aatgctccta atacgttcgg ccaagggacc aaggtggaaa    420
tcaaacgggc ggccgc                                                    436
```

<210> SEQ ID NO 14
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
ccatggccga ggtgcagctg ttggagtctg ggggaggctt ggtacagcct ggggggtccc     60
tgagactctc ctgtgcagcc tctggattca cctttagcag ctatgccatg agctgggtcc    120
gccaggctcc agggaagggg ctggagtggg tctcaaatat tgctggtaat ggttcttata    180
catattacgc agactccgtg aagggccggt tcaccatctc cagagacaat tccaagaaca    240
cgctgtatct gcaaatgaac agcctgagag ccgaggacac ggccgtatat tactgtgcga    300
aagatgatgc tgcttttgac tactggggcc agggaaccct ggtcaccgtc tcgagcggtg    360
gaggcggttc aggcggaggt ggcagcggcg gtggcgggtc gacggacatc cagatgaccc    420
agtctccatc ctccctgtct gcatctgtag gagacagagt caccatcact tgccgggcaa    480
gtcagagcat tagcagctat ttaaattggt atcagcagaa accagggaaa gcccctaagc    540
tcctgatcta ttctgcatcc tatttgcaaa gtggggtccc atcaaggttc agtggcagtg    600
gatctgggac agatttcact ctcaccatca gcagtctgca acctgaagat tttgcaactt    660
actactgtca acagagtgct actactccta atacgttcgg ccaagggacc aaggtggaaa    720
tcaaacgggc ggccgc                                                    736
```

<210> SEQ ID NO 15
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
ccatggccga ggtgcagctg ttggagtctg ggggaggctt ggtacagcct ggggggtccc     60
```

```
tgagactctc ctgtgcagcc tctggattca cctttagcag ctatgccatg agctgggtcc      120
gccaggctcc agggaagggg ctagagtggg tctcaactat taatactgct ggtaatggta      180
caaattacgc agactccgtg aagggccggt tcaccatctc cagagacaat tccaagaaca      240
cgctgtatct gcaaatgaac agcctgagag ccgaggacac ggccgtatat tactgtgcga      300
aaggtactgc tgcttttgac tactggggcc agggaaccct ggtcaccgtc tcgagcggtg      360
gaggcggttc aggcggaggt ggcagcggcg gtggcgggtc gacggacatc cagatgaccc      420
agtctccatc ctccctgtct gcatctgtag gagacagagt caccatcact tgccgggcaa      480
gtcagagcat tagcagctat ttaaattggt atcagcagaa accagggaaa gcccctaagc      540
tcctggtcta ttctgcatcc gctttgcaaa gtggggtccc atcaaggttc agtggcagtg      600
gatctgggac agatttcact ctcaccatca gcagtctgca acctgaagat tttgcaactt      660
actactgtca acaggctggt gatagtcctg ctacgttcgg ccaagggacc aaggtggaaa      720
tcaaacgggc ggccgc                                                     736

<210> SEQ ID NO 16
<211> LENGTH: 436
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
ccatggccga ggtgtttgac tactgggggcc agggaaccct ggtcaccgtc tcgagcggtg       60
gaggcggttc aggcggaggt ggcagcggcg gtggcgggtc gacggacatc cagatgaccc      120
agtctccatc ctccctgtct gcatctgtag gagacagagt caccatcact tgccgggcaa      180
gtcagagcat tagcagctat ttaaattggt atcagcagaa accagggaaa gcccctaagc      240
tcctgatcta ttatgcatcc actttgcaaa gtggggtccc atcaaggttc agtggcagtg      300
gatctgggac agatttcact ctcaccatca gcagtctgca acctgaagat tttgcaactt      360
actactgtca acagaattat aattctcctt atacgttcgg ccaagggacc aaggtggaaa      420
tcaaacgggc ggccgc                                                     436

<210> SEQ ID NO 17
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
ccatggccga ggtgcagctg ttggagtctg ggggaggctt ggtacagcct ggggggtccc       60
tgagactctc ctgtgcagcc tctggattca cctttagcag ctatgccatg agctgggtcc      120
gccaggctcc agggaagggg ctggagtggg tctcagatat tgatggtgct ggtagtgata      180
caggttacgc agactccgtg aagggccggt tcaccatctc cagagacaat tccaagaaca      240
cgctgtatct gcaaatgaac agcctgagag ccgaggacac ggccgtatat tactgtgcga      300
aatctactag tactttgac tactggggcc agggaaccct ggtcaccgtc tcgagcggtg      360
gaggcggttc aggcggaggt ggcagcggcg gtggcgggtc gacggacatc cagatgaccc      420
agtctccatc ctccctgtct gcatctgtag gagacagagt caccatcact tgccgggcaa      480
gtcagagcat tagcagctat ttaaattggt atcagcagaa accagggaaa gcccctaagc      540
```

```
tcctgatcta tggtgcatcc aatttgcaaa gtggggtccc atcaaggttc agtggcagtg      600
gatctgggac agatttcact ctcaccatca gcagtctgca acctgaagat tttgcaactt      660
actactgtca acagtctact actaatcctg ctacgttcgg ccaagggacc aaggtggaaa      720
tcaaacgggc ggccgc                                                     736
```

<210> SEQ ID NO 18
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
ccatggccga ggtgcagctg ttggagtctg ggggaggctt ggtacagcct ggggggtccc       60
tgagactctc ctgtgcagcc tctggattca cctttagcag ctatgccatg agctgggtcc      120
gccaggctcc agggaagggg ctggagtggg tctcatatat taatggtgat ggtgatagta      180
caacttacgc agactccgtg aagggccggt tcaccatctc cagagacaat tccaagaaca      240
cgctgtatct gcaaatgaac agcctgagag ccgaggacac ggccgtatat tactgtgcga      300
aatctaatac tgcttttgac tactggggcc agggaaccct ggtcaccgtc tcgagcggtg      360
gaggcggttc aggcggaggt ggcagcggcg gtggcgggtc gacggacatc cagatgaccc      420
agtctccatc ctccctgtct gcatctgtag gagacagagt caccatcact tgccgggcaa      480
gtcagagcat tagcagctat ttaaattggt atcagcagaa accagggaaa gcccctaagc      540
tcctgatcta ttatgcatcc actttgcaaa gtggggtccc atcaaggttc agtggcagtg      600
gatctgggac agatttcact ctcaccatca gcagtctgca acctgaagat tttgcaactt      660
actactgtca acagtcttct gctactcctg ctacgttcgg ccaagggacc aaggtggaaa      720
tcaaacgggc ggccgc                                                     736
```

<210> SEQ ID NO 19
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
ccatggccga ggtgcagctg ttggagtctg ggggaggctt ggtacagcct ggggggtccc       60
tgagactctc ctgtgcagcc tctggattca cctttagcag ctatgccatg agctgggtcc      120
gccaggctcc agggaagggg ctggagtggg tctcagctat tggtgcttct ggtaatgcta      180
cagcttacgc agactccgtg aagggccggt tcaccatctc cagagacaat tccaagaaca      240
cgctgtatct gcaaatgaac agcctgagag ccgaggacac ggccgtatat tactgtgcga      300
aatctactac tgattttgac tactggggcc agggaaccct ggtcaccgtc tcgagcggtg      360
gaggcggttc aggcggaggt ggcagcggcg gtggcgggtc gacggacatc cagatgaccc      420
agtctccatc ctccctgtct gcatctgtag gagacagagt caccatcact tgccgggcaa      480
gtcagagcat tagcagctat ttaaattggt atcagcagaa accagggaaa gcccctaagc      540
tcctgatcta taatgcatcc ggtttgcaaa gtggggtccc atcaaggttc agtggcagtg      600
gatctgggac agatttcact ctcaccatca gcagtctgca acctgaagat tttgcaactt      660
```

```
actactgtca acaggcagct aattatccta ctacgttcgg ccaagggacc aaggtggaaa    720
tcaaacgggc ggccgc                                                    736

<210> SEQ ID NO 20
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
ccatggccga ggtgcagctg ttggagtctg ggggaggctt ggtacagcct ggggggtccc     60
tgagactctc ctgtgcagcc tctggattca cctttagcag ctatgccatg agctgggtcc    120
gccaggctcc agggaagggg ctggagtggg tctcagctat tgcttctgat ggtactaata    180
catcttacgc agactccgtg aagggccggt tcaccatctc cagagacaat tccaagaaca    240
cgctgtatct gcaaatgaac agcctgagag ccgaggacac ggccgtatat tactgtgcga    300
aaactgatgg tgattttgac tattggggcc agggaaccct ggtcaccgtc tcgagcggtg    360
gaggcggttc aggcggaggt ggcagcgcg gtggcgggtc gacggccatc cagatgaccc    420
agtctccatc ctccctgtct gcatctgtag gagacagagt caccatcact tgccgggcaa    480
gtcagagcat tagcagctat ttaaattggt atcagcagaa accagggaaa gcccctaagc    540
tcctgatcta tactgcatcc tatttgcaaa gtggggtccc atcaaggttc agtggcagtg    600
gatctgggac agatttcact ctcaccatca gcagtctgca acctgaagat tttgcaactt    660
actactgtca acagactgct gctagtccta atacgttcgg ccaagggacc aaggtggaaa    720
tcaaacgggc ggccgc                                                    736

<210> SEQ ID NO 21
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
ccatggccga ggtgcagctg ttggagtctg ggggaggctt ggtacagcct ggggggtccc     60
tgagactctc ctgtgcagcc tctggattca cctttagcag ctatgccatg agctgggtcc    120
gccaggctcc agggaagggg ctggagtggg tctcaactat tgctgctggt ggtgataata    180
caacttacgc agactccgtg aagggccggt tcaccatctc cagagacaat tccaagaaca    240
cgctgtatct gcaaatgaac agcctgagag ccgaggacac ggccgtatat tactgtgcga    300
aagattctta tactttgac tactggggcc agggaaccct ggtcaccgtc tcgagcggtg    360
gaggcggttc aggcggaggt ggcagcgcg gtggcgggtc gacggacatc cagatgaccc    420
agtctccatc ctccctgtct gcatctgtag gagacagagt caccatcact tgccgggcaa    480
gtcagagcat tagcagctat ttaaattggt atcagcagaa accagggaaa gcacctaagc    540
tcctgatcta ttctgcatcc actttgcaaa gtggggtccc atcaaggttc agtggcagtg    600
gatctgggac agatttcact ctcaccatca gcagtctgca acctgaagat tttgcaactt    660
actactgtca acagagtact actactcctg ctacgttcgg ccaagggacc aaggtggaaa    720
tcaaacgggc ggccgc                                                    736
```

<210> SEQ ID NO 22
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
ccatggccga ggtgcagctg ttggagtctg ggggaggctt ggtacagcct ggggggtccc      60
tgagactctc ctgtgcagcc tctggattca cctttagcag ctatgccatg agctgggtcc     120
gccaggctcc agggaaggga ctggagtggg tctcatctat ttcttctact ggttctgata     180
caacttacgc agactccgtg aagggccggt tcaccatctc cagagacaat tccaagaaca     240
cgctgtatct gcaaatgaac agcctgagag ccgaggacac ggccgtatat tactgtgcga     300
aagctggttc ttcttttgac tactggggcc agggaaccct ggtcaccgtc tcgagcggtg     360
gaggcggttc aggcggaggt ggcagcggcg gtggcgggtc gacggacatc cagatgaccc     420
agtctccatc ctccctgtct gcatctgtag gagacagagt caccatcact tgccgggcaa     480
gtcagagcat tagcagctat ttaaattggt atcagcagaa accagggaaa gcccctaagc     540
tcctgatcta tgctgcatcc aatttgcaaa gtggggtccc atcaaggttc agtggcagtg     600
gatctgggac agatttcact ctcaccatca gcagtctgca acctgaagat tttgcaactt     660
actactgtca acagagttct tattctcctt ctacgttcgg ccaagggacc aaggtggaaa     720
tcaaacgggc ggccgc                                                     736

<210> SEQ ID NO 23
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (57)..(57)
<223> OTHER INFORMATION: a, c, t, g, unknown or other
<220> FEATURE:
<221> NAME/KEY: modified_base
<222> LOCATION: (641)..(641)
<223> OTHER INFORMATION: a, c, t, g, unknown or other
<220> FEATURE:
<221> NAME/KEY: modified_base
<222> LOCATION: (643)..(645)
<223> OTHER INFORMATION: a, c, t, g, unknown or other
<220> FEATURE:
<221> NAME/KEY: modified_base
<222> LOCATION: (709)..(709)
<223> OTHER INFORMATION: a, c, t, g, unknown or other

<400> SEQUENCE: 23
ccatggccga ggtgcagctg ttggagtctg ggggaggctt ggtacagcct gggggggnccc     60 tgagactctc ctgtgcagcc tctggattca cctttagcag ctatgccatg agctgggtcc    120
gccaggctcc agggaagggg ctggagtggg tctcaagtat tgctagttct ggtactagta    180
catcttacgc agactccgtg aagggccggt tcaccatctc cagagacaat tccaagaaca    240
cgctgtatct gcaaatgaac agcctgagag ccgaggacac ggccgtatat tactgtgcga    300
aagctactaa ttcttttgac tattggggcc agggaaccct ggtcaccgtc tcgagcggtg    360
gaggcggttc aggcggaggt ggcagcggcg gtggcgggtc gacggacatc cagatgaccc    420
agtctccatc ctccctgtct gcatctgtag gagacagagt caccatcact tgccgggcaa    480

```
gtcagagcat tagcagctat ttaaattggt atcagcagaa accagggaaa gccccctaagc    540 tcctgatcta taatgcatcc actttgcaaa gtggggtccc atcaaggttc agtggcagtg    600
gatctgggac agatttcact ctcaccatca gcagtctgca ncnnnaagat tttgcaactt    660
actactgtca acagactgat gcttctcctt gtacgttcgg ccaaggganc aaggtggaaa    720
tcaaacgggc ggccgc                                                    736
```

<210> SEQ ID NO 24
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (385)..(385)
<223> OTHER INFORMATION: a, c, t, g, unknown or other
<220> FEATURE:
<221> NAME/KEY: modified_base
<222> LOCATION: (392)..(392)
<223> OTHER INFORMATION: a, c, t, g, unknown or other

<400> SEQUENCE: 24

```
ccatggccga ggtgcagctg ttggagtctg ggggaggctt ggtacagcct ggggggtccc     60
tgagactctc ctgtgcagcc tctggattca cctttagcag ctatgccatg agctgggtcc    120
gccaggctcc agggaagggg ctggagtggg tctcaaatat ttataatgat ggtactagta    180
cagattacgc agactccgtg aagggcaggt tcaccatctc cagagacaat tccaagaaca    240
cgctgtatct gcaaatgaac agcctgagag ccgaggacac ggccgtatat tactgtgcga    300
aatcttctag tgcttttgac tactgggggcc agggaaccct ggtcaccgtc tcgagcggtg    360
gaggcggttc aggcggaggt ggcancggcg gnggcgggtc gacggacatc cagatgaccc    420
agtctccatc ctccctgtct gcatctgtag gagacagagt caccatcact tgccgggcaa    480
gtcagagcat tagcagctat ttaaattggt atcagcagaa accagggaaa gccccctaagc   540 tcctgatcta tactgcatcc tctttgcaaa gtggggtccc atcaaggttc agtggcagtg    600
gatctgggac agatttcact ctcaccatca gcagtctgca acctgaagat tttgcaactt    660
actactgtca acagtatgat agtactccta ctacgttcgg ccaagggacc aaggtggaaa    720
tcaaacgggc ggccgc                                                    736
```

<210> SEQ ID NO 25
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
ccatggccga ggtgcagctg ttggagtctg ggggaggctt ggtacggcct ggggggtccc     60
tgagactctc ctgtgcagcc tctggattca cctttagcag ctatgccatg agctgggtcc    120
gccaggctcc agggaagggg ctggagtggg tctcagatat tgctaatact ggtgatgcta    180
caggttacgc agactccgtg aagggccggt tcaccatctc cagagacaat tccaagaaca    240
cgctgtatct gcaaatgaac agcctgagag ccgaggacac ggccgtatat tactgtgcga    300
aaactgtgtc tgcttttgac tactgggggcc agggaaccct ggtcaccgtc tcgagcggtg    360
gaggcggttc aggcggaggt ggcagcggcg gtggcgggtc gacggacatc cagatgaccc    420
```

```
agtctccatc ctccctgtct gcatctgtag gagacagagt caccatcact tgccgggcaa      480
gtcagagcat tagcagctat ttaaattggt atcagcagaa accagggaaa gcccctaagc      540
tcctgatcta tgctgcatcc actttgcaaa gtggggtccc gtcaaggttc agtggcagtg      600
gatctgggac agatttcact ctcaccatca gcagtctgca acctgaagat tttgcaactt      660
actactgtca acagagttct agtgatcctg ctacgttcgg ccaagggacc aaggtggaaa      720
tcaaacgggc ggccgc                                                      736

<210> SEQ ID NO 26
<211> LENGTH: 733
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (708)..(708)
<223> OTHER INFORMATION: a, c, t, g, unknown or other
<220> FEATURE:
<221> NAME/KEY: modified_base
<222> LOCATION: (723)..(723)
<223> OTHER INFORMATION: a, c, t, g, unknown or other

<400> SEQUENCE: 26
ccatggccca ggtgtagctg gtgcagtctg ggggaggctc ggtccagccg gggggtccc       60 tgagactctc ctgtgtagac tctggattca ccttcaatag ctctggcatg cactgggtcc     120
gccaggctcc aggcaagggg ctggagtggg tggcgtttat acgccatgat ggaagtaaga     180
aatactatgc agactccgtg aagggccgat tcaccatctc cagagacagt gccaagaaca     240
ctctgtatct gcaaatggac agcctgagag ccgaggacac ggccgtatat tactgtgcga     300
aagacatggg agcgactgac tactggggcc agggaaccct ggtcaccgtc tcctcaggtg     360
gaggcggttc aggcggaggt ggctctggcg gtggcggatc gtctgagctg actcaggacc     420
ctgctgtgtc tgtggccttg ggacagacag tcagaatcac atgccaagga gacagcctca     480
aaagctacta tgcaagttgg taccagcaga agccaggaca ggcccctgca cttgtcatct     540
atggtaaaaa caaccggccc tcagggatcc cagaccgatt ctctggctcc agctcaggaa     600
acacagcttc cttgaccatc actgggactc tggcggaaga tgaggctgac tattactgta     660
actcccggga cagcagtggt aaccgtgtgc tattcggcgg agggaccnag ctgaccgtcc     720
tangtgcggc cgc                                                         733

<210> SEQ ID NO 27
<211> LENGTH: 942
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (699)..(699)
<223> OTHER INFORMATION: a, c, t, g, unknown or other
<220> FEATURE:
<221> NAME/KEY: modified_base
<222> LOCATION: (701)..(701)
<223> OTHER INFORMATION: a, c, t, g, unknown or other
<220> FEATURE:
<221> NAME/KEY: modified_base
<222> LOCATION: (709)..(709)
<223> OTHER INFORMATION: a, c, t, g, unknown or other
<220> FEATURE:
```

```
<221> NAME/KEY: modified_base
<222> LOCATION: (712)..(712)
<223> OTHER INFORMATION: a, c, t, g, unknown or other
<220> FEATURE:
<221> NAME/KEY: modified_base
<222> LOCATION: (732)..(732)
<223> OTHER INFORMATION: a, c, t, g, unknown or other
<220> FEATURE:
<221> NAME/KEY: modified_base
<222> LOCATION: (763)..(764)
<223> OTHER INFORMATION: a, c, t, g, unknown or other
<220> FEATURE:
<221> NAME/KEY: modified_base
<222> LOCATION: (770)..(770)
<223> OTHER INFORMATION: a, c, t, g, unknown or other
<220> FEATURE:
<221> NAME/KEY: modified_base
<222> LOCATION: (785)..(785)
<223> OTHER INFORMATION: a, c, t, g, unknown or other
<220> FEATURE:
<221> NAME/KEY: modified_base
<222> LOCATION: (788)..(788)
<223> OTHER INFORMATION: a, c, t, g, unknown or other
<220> FEATURE:
<221> NAME/KEY: modified_base
<222> LOCATION: (790)..(792)
<223> OTHER INFORMATION: a, c, t, g, unknown or other
<220> FEATURE:
<221> NAME/KEY: modified_base
<222> LOCATION: (807)..(807)
<223> OTHER INFORMATION: a, c, t, g, unknown or other
<220> FEATURE:
<221> NAME/KEY: modified_base
<222> LOCATION: (816)..(816)
<223> OTHER INFORMATION: a, c, t, g, unknown or other
<220> FEATURE:
<221> NAME/KEY: modified_base
<222> LOCATION: (824)..(824)
<223> OTHER INFORMATION: a, c, t, g, unknown or other
<220> FEATURE:
<221> NAME/KEY: modified_base
<222> LOCATION: (835)..(836)
<223> OTHER INFORMATION: a, c, t, g, unknown or other
<220> FEATURE:
<221> NAME/KEY: modified_base
<222> LOCATION: (838)..(839)
<223> OTHER INFORMATION: a, c, t, g, unknown or other
<220> FEATURE:
<221> NAME/KEY: modified_base
<222> LOCATION: (843)..(843)
<223> OTHER INFORMATION: a, c, t, g, unknown or other
<220> FEATURE:
<221> NAME/KEY: modified_base
<222> LOCATION: (860)..(860)
<223> OTHER INFORMATION: a, c, t, g, unknown or other
<220> FEATURE:
<221> NAME/KEY: modified_base
<222> LOCATION: (875)..(876)
<223> OTHER INFORMATION: a, c, t, g, unknown or other
<220> FEATURE:
<221> NAME/KEY: modified_base
<222> LOCATION: (879)..(879)
<223> OTHER INFORMATION: a, c, t, g, unknown or other
<220> FEATURE:
<221> NAME/KEY: modified_base
<222> LOCATION: (883)..(884)
<223> OTHER INFORMATION: a, c, t, g, unknown or other
<220> FEATURE:
<221> NAME/KEY: modified_base
<222> LOCATION: (890)..(890)
<223> OTHER INFORMATION: a, c, t, g, unknown or other
<220> FEATURE:
<221> NAME/KEY: modified_base
<222> LOCATION: (893)..(893)
<223> OTHER INFORMATION: a, c, t, g, unknown or other
<220> FEATURE:
<221> NAME/KEY: modified_base
<222> LOCATION: (896)..(897)
<223> OTHER INFORMATION: a, c, t, g, unknown or other
```

<220> FEATURE:
<221> NAME/KEY: modified_base
<222> LOCATION: (900)..(906)
<223> OTHER INFORMATION: a, c, t, g, unknown or other
<220> FEATURE:
<221> NAME/KEY: modified_base
<222> LOCATION: (909)..(909)
<223> OTHER INFORMATION: a, c, t, g, unknown or other
<220> FEATURE:
<221> NAME/KEY: modified_base
<222> LOCATION: (911)..(911)
<223> OTHER INFORMATION: a, c, t, g, unknown or other
<220> FEATURE:
<221> NAME/KEY: modified_base
<222> LOCATION: (913)..(917)
<223> OTHER INFORMATION: a, c, t, g, unknown or other
<220> FEATURE:
<221> NAME/KEY: modified_base
<222> LOCATION: (923)..(935)
<223> OTHER INFORMATION: a, c, t, g, unknown or other
<220> FEATURE:
<221> NAME/KEY: modified_base
<222> LOCATION: (938)..(938)
<223> OTHER INFORMATION: a, c, t, g, unknown or other
<220> FEATURE:
<221> NAME/KEY: modified_base
<222> LOCATION: (940)..(940)
<223> OTHER INFORMATION: a, c, t, g, unknown or other

<400> SEQUENCE: 27

```
ccatggccga ggtgcagctg ttggagtctg ggggaggctt ggtacagcct ggggggtccc      60
tgagactctc ctgtgcagcc tctggattca cctttagcag ctatgccatg agctgggtcc     120
gccaggctcc agggaagggg ctggagtggg tctcaagtat tacttcttct ggtgattcta     180
catcttacgc agactccgtg aagggccggt tcaccatctc cagagacaat tccaagaaca     240
cgctgtatct gcaaatgaac agcctgagag ccgaggacac ggccgtatat tactgtgcga     300
aatatagtag tgattttgac tactggggcc agggaaccct ggtcaccgtc tcgagcggtg     360
gaggcggttc aggcggaggt ggcagcggcg gtggcgggtc gacggacatc cagatgaccc     420
agtctccatc ctccctgtct gcatctgtag gagacagagt caccatcact tgccgggcaa     480
gtcagagcat tagcagctat ttaaattggt atcagcagaa accagggaaa gcccctaagc     540
tcctgatcta ttctgcatcc gctttgcaaa gtggggtccc aacaaggttc agtggcagtg     600
gatctgggac agatttcact ctcaccatca gcagtctgca acctgaagat tttgcaactt     660
actactgtca acaggctaat actactccta ctacgttcng nccaagggnc naggtggaa     720
atcaaacggg cnggccgcac atcatcatca ccatcacggg gcnncagaan aaaaactcat     780
ctcanaanan nntctgaatg gggccgnata gactgntgaa agtngtttag caaanntnnt     840
acngaaaatt catttactan gtctggaaag acganaaant ttnnatcgtn acnctnnctn     900
nnnnnntgnc ngnnnnngct acnnnnnnnn nnnnacngn ga                        942
```

<210> SEQ ID NO 28
<211> LENGTH: 866
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (670)..(670)
<223> OTHER INFORMATION: a, c, t, g, unknown or other
<220> FEATURE:
<221> NAME/KEY: modified_base
<222> LOCATION: (676)..(676)
<223> OTHER INFORMATION: a, c, t, g, unknown or other

```
<220> FEATURE:
<221> NAME/KEY: modified_base
<222> LOCATION: (733)..(733)
<223> OTHER INFORMATION: a, c, t, g, unknown or other
<220> FEATURE:
<221> NAME/KEY: modified_base
<222> LOCATION: (759)..(761)
<223> OTHER INFORMATION: a, c, t, g, unknown or other
<220> FEATURE:
<221> NAME/KEY: modified_base
<222> LOCATION: (768)..(768)
<223> OTHER INFORMATION: a, c, t, g, unknown or other
<220> FEATURE:
<221> NAME/KEY: modified_base
<222> LOCATION: (782)..(788)
<223> OTHER INFORMATION: a, c, t, g, unknown or other
<220> FEATURE:
<221> NAME/KEY: modified_base
<222> LOCATION: (802)..(803)
<223> OTHER INFORMATION: a, c, t, g, unknown or other
<220> FEATURE:
<221> NAME/KEY: modified_base
<222> LOCATION: (805)..(805)
<223> OTHER INFORMATION: a, c, t, g, unknown or other
<220> FEATURE:
<221> NAME/KEY: modified_base
<222> LOCATION: (808)..(808)
<223> OTHER INFORMATION: a, c, t, g, unknown or other
<220> FEATURE:
<221> NAME/KEY: modified_base
<222> LOCATION: (813)..(813)
<223> OTHER INFORMATION: a, c, t, g, unknown or other
<220> FEATURE:
<221> NAME/KEY: modified_base
<222> LOCATION: (827)..(827)
<223> OTHER INFORMATION: a, c, t, g, unknown or other
<220> FEATURE:
<221> NAME/KEY: modified_base
<222> LOCATION: (830)..(831)
<223> OTHER INFORMATION: a, c, t, g, unknown or other
<220> FEATURE:
<221> NAME/KEY: modified_base
<222> LOCATION: (833)..(838)
<223> OTHER INFORMATION: a, c, t, g, unknown or other
<220> FEATURE:
<221> NAME/KEY: modified_base
<222> LOCATION: (844)..(844)
<223> OTHER INFORMATION: a, c, t, g, unknown or other
<220> FEATURE:
<221> NAME/KEY: modified_base
<222> LOCATION: (846)..(848)
<223> OTHER INFORMATION: a, c, t, g, unknown or other
<220> FEATURE:
<221> NAME/KEY: modified_base
<222> LOCATION: (851)..(851)
<223> OTHER INFORMATION: a, c, t, g, unknown or other
<220> FEATURE:
<221> NAME/KEY: modified_base
<222> LOCATION: (857)..(858)
<223> OTHER INFORMATION: a, c, t, g, unknown or other
<220> FEATURE:
<221> NAME/KEY: modified_base
<222> LOCATION: (861)..(861)
<223> OTHER INFORMATION: a, c, t, g, unknown or other
<220> FEATURE:
<221> NAME/KEY: modified_base
<222> LOCATION: (865)..(865)
<223> OTHER INFORMATION: a, c, t, g, unknown or other

<400> SEQUENCE: 28
ccatggccga ggtgcagctg ttggagtctg ggggaggctt ggtacagcct ggggggtccc      60
tgagactctc ctgtgcagcc tctggattca cctttagcag ctatgccatg agctgggtcc     120
gccaggctcc agggaagggg ctggagtggg tctcatctat ttagcctact ggtaggcgga     180
catcgtacgc agactccgtg aagggccggt tcaccatctc cagagacaat tccaagaaca     240
```

```
cgctgtatct gcaaatgaac agcctgagag ccgaggacac ggccgtatat tactgtgcga      300
aaagtcgtac gccgtttgac tactggggcc agggaaccct ggtcaccgtc tcgagcggtg      360
gaggcggttc aggcggaggt ggcagcggcg gtggcgggtc gacggacatc cagatgaccc      420
agtctccatc ctccctgtct gcatctgtag gagacagagt caccatcact tgccgggcaa      480
gtcagagcat tagcagctat ttaaaattgg atcagcagaa accagggaaa gcccctaagc      540
tcctgatcta ttctgcatcc atcttgcaaa gtggggtccc atcaaggttc agtggcagtg      600
gatctgggac agatttcact ctcaccatca gcagtctgca acctgaagat tttgcaactt      660
actactgtcn acagantacg cctgctcctg gacgttcgg ccaagggacc aaggtggaaa      720
tcaaacgggc ggncgcacat catcatcacc atcacgggnn ngcagaanaa aaactcatct      780
cnnnnnnnat ctgaatgggg cnncntanac tgntgaaagt gttagcnaan ntnnnnnnga      840
aaantnnntt nctaacnnct ngaana                                            866

<210> SEQ ID NO 29
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(100)
<223> OTHER INFORMATION: This region may encompass 3 to 100 "Gly"
      residues, wherein some positions may be absent
<220> FEATURE:
<221> NAME/KEY: misc_feature
<222> LOCATION: (102)..(201)
<223> OTHER INFORMATION: This region may encompass 3 to 100 "Gly"
      residues, wherein some positions may be absent

<400> SEQUENCE: 29

Gly Gly Gly Gly Gly Gly Gly Gly Gly Gly Gly Gly Gly Gly Gly Gly
 1               5                  10                  15

Gly Gly Gly Gly Gly Gly Gly Gly Gly Gly Gly Gly Gly Gly Gly Gly
             20                  25                  30

Gly Gly Gly Gly Gly Gly Gly Gly Gly Gly Gly Gly Gly Gly Gly Gly
         35                  40                  45

Gly Gly Gly Gly Gly Gly Gly Gly Gly Gly Gly Gly Gly Gly Gly Gly
     50                  55                  60

Gly Gly Gly Gly Gly Gly Gly Gly Gly Gly Gly Gly Gly Gly Gly Gly
 65                  70                  75                  80

Gly Gly Gly Gly Gly Gly Gly Gly Gly Gly Gly Gly Gly Gly Gly Gly
                 85                  90                  95

Gly Gly Gly Gly Pro Gly Gly Gly Gly Gly Gly Gly Gly Gly Gly Gly
            100                 105                 110

Gly Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly Gly
145                 150                 155                 160
```

-continued

```
Gly Gly Gly Gly Gly Gly Gly Gly Gly Gly Gly Gly Gly Gly Gly
                165                 170                 175
Gly Gly Gly Gly Gly Gly Gly Gly Gly Gly Gly Gly Gly Gly Gly
            180                 185                 190
Gly Gly Gly Gly Gly Gly Gly Gly Gly
        195                 200
```